US012807732B2

(12) United States Patent
Padler-Karavani et al.

(10) Patent No.: US 12,807,732 B2
(45) Date of Patent: Nov. 24, 2026

(54) HUMANIZED ANTIBODIES AND FRAGMENTS THEREOF BINDING TO CARBOHYDRATE ANTIGENS AND USES THEREOF

(71) Applicant: RAMOT AT TEL-AVIV UNIVERSITY LTD., Tel Aviv (IL)

(72) Inventors: Vered Padler-Karavani, Tel Aviv (IL); Ron Amon, Tel Aviv (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 721 days.

(21) Appl. No.: 18/254,255

(22) PCT Filed: Nov. 23, 2021

(86) PCT No.: PCT/IL2021/051390
§ 371 (c)(1),
(2) Date: May 24, 2023

(87) PCT Pub. No.: WO2022/113066
PCT Pub. Date: Jun. 2, 2022

(65) Prior Publication Data

US 2024/0043561 A1 Feb. 8, 2024

Related U.S. Application Data

(60) Provisional application No. 63/117,493, filed on Nov. 24, 2020.

(51) Int. Cl.
*C07K 16/30* (2006.01)
*A61K 40/10* (2025.01)
*A61K 40/31* (2025.01)

(52) U.S. Cl.
CPC .......... *C07K 16/3076* (2013.01); *A61K 40/10* (2025.01); *A61K 40/31* (2025.01); *A61K 2239/13* (2023.05); *A61K 2239/21* (2023.05); *C07K 2317/24* (2013.01); *C07K 2317/565* (2013.01); *C07K 2317/567* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,471,057 | A | 9/1984 | Koprowski |
| 7,465,787 | B2 | 12/2008 | Wittrup |
| 10,036,747 | B2 | 7/2018 | Pancer |
| 2020/0308223 | A1 | 10/2020 | Chang |

FOREIGN PATENT DOCUMENTS

| | | | | |
|---|---|---|---|---|
| EP | 0404097 A2 | 12/1990 | | |
| EP | 3328894 B1 | 11/2018 | | |
| EP | 3265490 B1 | 5/2019 | | |
| EP | 3423496 B1 | 7/2019 | | |
| KR | 20190092285 A | 8/2019 | | |
| WO | 9311161 A1 | 6/1993 | | |
| WO | WO-0127159 A2 * | 4/2001 | .......... | C07K 16/303 |
| WO | 2012079000 A1 | 6/2012 | | |
| WO | 2013040557 A2 | 3/2013 | | |
| WO | 2013074916 A1 | 5/2013 | | |
| WO | 2015053871 A2 | 4/2015 | | |
| WO | 2016057890 A1 | 4/2016 | | |
| WO | 2016077526 A1 | 5/2016 | | |
| WO | 2017025038 A1 | 2/2017 | | |
| WO | 2018160909 A1 | 9/2018 | | |
| WO | 2020081988 A1 | 4/2020 | | |
| WO | 2021105988 A1 | 6/2021 | | |
| WO | 2021105989 A1 | 6/2021 | | |
| WO | 2022153298 A1 | 7/2022 | | |

OTHER PUBLICATIONS

Partyka et al., (2012) Diverse monoclonal antibodies against the CA 19-9 antigen show variation in binding specificity with consequences for clinical interpretation. Author Manuscript. Proteomics 12(13): 2212-2220.
Sawada et al., (2011) Human monoclonal antibodies to sialyl-Lewis (CA19.9) with potent CDC, ADCC, and antitumor activity. Clin Cancer Res 17(5): 1024-1032.
Ahmadzadeh et al., (2014) Antibody humanization methods for development of therapeutic applications. Monoclon Antib Immunodiagn Immunother 33(2): 67-73.
Amon et al., (2014) Glycans in immune recognition and response. Carbohydr Res 389: 115-122.
Amon et al., (2018) A combined computational-experimental approach to define the structural origin of antibody recognition of sialyl-Tn, a tumor-associated carbohydrate antigen. Sci Rep 8(1): 10786.
Amon et al., (2020) Directed Evolution of Therapeutic Antibodies Targeting Glycosylation in Cancer. Cancers (Basel) 12(10): 2824. With Supplementary Materials.
Angelini et al., (2015) Protein Engineering and Selection Using Yeast Surface Display. Methods Mol Biol 1319: 3-36.
Ankri and Cohen (2014) Out of the bitter came forth sweet: Activating CD28-dependent co-stimulation via PD-1 ligands. Oncoimmunology 3(1): e27399.

(Continued)

*Primary Examiner* — Samira J Jean-Louis
*Assistant Examiner* — Maureen Varina Driscoll
(74) *Attorney, Agent, or Firm* — Ballard Spahr LLP

(57) ABSTRACT

The present invention discloses humanized monoclonal antibodies that specifically bind to SLeA carbohydrate antigen with high specificity and selectivity, functional fragments of the humanized monoclonal antibodies such as scFv, and chimeric antigen receptors comprising the humanized monoclonal antibodies or the fragment thereof such as scFv. The invention further provides cells and compositions comprising the antibodies, fragments thereof or CARs as well as their use in diagnostics and treatment of cancer.

21 Claims, 11 Drawing Sheets

Specification includes a Sequence Listing.

(56) References Cited

OTHER PUBLICATIONS

Ashkani and Naidoo (2016) Glycosyltransferase Gene Expression Profiles Classify Cancer Types and Propose Prognostic Subtypes. Sci Rep 6: 26451.
Ballehaninna and Chamberlain (2011) Serum CA 19-9 as a Biomarker for Pancreatic Cancer-A Comprehensive Review. Indian J Surg Oncol 2(2): 88-100.
Ballehaninna and Chamberlain (2012) The clinical utility of serum CA 19-9 in the diagnosis, prognosis and management of pancreatic adenocarcinoma: An evidence based appraisal. J Gastrointest Oncol 3(2): 105-119.
Bashir et al., (2019) Presentation Mode of Glycans Affect Recognition of Human Serum anti-Neu5Gc IgG Antibodies. Bioconjug Chem. Author manuscript; available in PMC Jan. 16, 2020. Published in final edited form as: Bioconjug Chem. Jan. 16, 2019; 30(1): 161-168.
Bauer et al., (2011) CA19-9 for the prediction of efficacy of chemotherapy in patients with advanced pancreas cancer: A pooled analysis of six prospective trials. J Clin Oncol 29(15_suppl): 4071.
Benatuil et al., (2010) An improved yeast transformation method for the generation of very large human antibody libraries. Protein Eng Des Sel 23(4): 155-159.
Bird et al., (1988) Single-chain antigen-binding proteins. Science 242(4877): 423-426.
Boder et al., (2012) Engineering antibodies by yeast display. Arch Biochem Biophys 526(2): 99-106.
Boligan et al., (2015) Cancer intelligence acquired (CIA): tumor glycosylation and sialylation codes dismantling antitumor defense. Cell Mol Life Sci 72(7): 1231-1248.
Borentain et al., (2016) Inhibition of E-selectin expression on the surface of endothelial cells inhibits hepatocellular carcinoma growth by preventing tumor angiogenesis. Cancer Chemother Pharmacol 77(4): 847-856.
Boyiadzis et al., (2018) Chimeric antigen receptor (CAR) T therapies for the treatment of hematologic malignancies: clinical perspective and significance. J Immunother Cancer 6(1): 137.
Brooks et al., (2008) Altered glycosylation of proteins in cancer: what is the potential for new anti-tumour strategies. Anticancer Agents Med Chem 8(1): 2-21.
Brudno et al., (2020) Safety and feasibility of anti-CD19 CAR T cells with fully human binding domains in patients with B-cell lymphoma. Nat Med. Author manuscript; available in PMC Jan. 4, 2021. Published in final edited form as: Nat Med. Feb. 2020; 26(2): 270-280.
Carr et al., (2000) A mouse IgG1 monoclonal antibody specific for N-glycolyl GM3 ganglioside recognized breast and melanoma tumors. Hybridoma 19(3): 241-247.
Chao et al., (2006) Isolating and engineering human antibodies using yeast surface display. Nat Protoc 1(2): 755-768.
Cherf and Cochran (2015) Applications of Yeast Surface Display for Protein Engineering. Methods Mol Biol. Author manuscript; available in PMC Jan. 1, 2016. Published in final edited form as: Methods Mol Biol. 2015; 1319: 155-175.
Chiavenna et al., (2017) State of the art in anti-cancer mAbs. J Biomed Sci 24(1): 15.
Chojnacki et al., (2017) Programmatic access to bioinformatics tools from EMBL-EBI update: 2017. Nucleic Acids Res 45(W1): W550-W553.
Cohen and Varki (2010) The sialome—far more than the sum of its parts. OMICS 14(4): 455-464.
Colby et al., (2004) Engineering antibody affinity by yeast surface display. Methods Enzymol 388: 348-358.
DeSelm et al., (2018) Low-Dose Radiation Conditioning Enables CAR T Cells to Mitigate Antigen Escape. Mol Ther 26 (11): 2542-2552.
Dingjan et al., (2015) Structural biology of antibody recognition of carbohydrate epitopes and potential uses for targeted cancer immunotherapies. Mol Immunol 67(2 Pt A): 75-88.
Doerner et al., (2014) Therapeutic antibody engineering by high efficiency cell screening. FEBS Lett 588(2): 278-287.
Dube and Bertozzi (2005) Glycans in cancer and inflammation—potential for therapeutics and diagnostics. Nat Rev Drug Discov 4(6): 477-488.
Elinav et al., (2009) Amelioration of colitis by genetically engineered murine regulatory T cells redirected by antigen-specific chimeric receptor. Gastroenterology 136(5): 1721-1731.
Eshhar et al., (1993) Specific activation and targeting of cytotoxic lymphocytes through chimeric single chains consisting of antibody-binding domains and the gamma or zeta subunits of the immunoglobulin and T-cell receptors. Proc Natl Acad Sci U S A 90(2): 720-724.
Feldhaus and Siegel (2004) Yeast display of antibody fragments: a discovery and characterization platform. J Immunol Methods 290(1-2): 69-80.
Fesnak et al., (2016) Engineered T cells: the promise and challenges of cancer immunotherapy. Nat Rev Cancer. Author manuscript; available in PMC Aug. 23, 2017. Published in final edited form as: Nat Rev Cancer. Aug. 23, 2016; 16 (9): 566-581.
Friedmann-Morvinski et al., (2005) Redirected primary T cells harboring a chimeric receptor require costimulation for their antigen-specific activation. Blood 105(8): 3087-3093.
Fuster and Esko (2005) The sweet and sour of cancer: glycans as novel therapeutic targets. Nat Rev Cancer 5(7): 526-542.
Gauthier and Yakoub-Agha (2017) Chimeric antigen-receptor T-cell therapy for hematological malignancies and solid tumors: Clinical data to date, current limitations and perspectives. Curr Res Transl Med 65(3): 93-102.
Gietz and Schiestl (2007) Frozen competent yeast cells that can be transformed with high efficiency using the LiAc/SS carrier DNA/PEG method. Nat Protoc 2(1): 1-4.
Giudicelli et al., (2006) IMGT/LIGM-DB, the IMGT comprehensive database of immunoglobulin and T cell receptor nucleotide sequences. Nucleic Acids Res 34(Database issue): D781-D784.
Golijanin et al., (1995) Detection of bladder tumors by immunostaining of the Lewis X antigen in cells from voided urine. Urology 46(2): 173-177.
Gross et al., (1989) Expression of immunoglobulin-T-cell receptor chimeric molecules as functional receptors with antibody-type specificity. Proc Natl Acad Sci U S A 86(24): 10024-10028.
Guo and Wang (2009) Recent development in carbohydrate-based cancer vaccines. Curr Opin Chem Biol. Author manuscript; available in PMC Dec. 1, 2010. Published in final edited form as: Curr Opin Chem Biol. Dec. 2009; 13(5-6): 608-617.
Haji-Ghassemi et al., (2015) Antibody recognition of carbohydrate epitopes. Glycobiology 25(9): 920-952.
Hanes et al., (1998) Ribosome display efficiently selects and evolves high-affinity antibodies in vitro from immune libraries. Proc Natl Acad Sci U S A 95(24): 14130-14135.
Hanisch et al., (1992) Sialyl Lewis(x) antigen as defined by monoclonal antibody AM-3 is a marker of dysplasia in the colonic adenoma-carcinoma sequence. Cancer Res 52(11): 3138-3144.
Hedlund et al., (2008) alpha 2-6-Linked sialic acids on N-glycans modulate carcinoma differentiation in vivo. Cancer Res 68(2): 388-394.
Heimburg-Molinaro et al., (2011) Cancer vaccines and carbohydrate epitopes. Vaccine. Author manuscript; available in PMC Nov. 8, 2012. Published in final edited form as: Vaccine. Nov. 8, 2011; 29(48): 8802-8826.
Holliger et al., (1993) "Diabodies": small bivalent and bispecific antibody fragments. Proc Natl Acad Sci U S A 90(14): 6444-6448.
Hong et al., (2013) Sugar-binding proteins from fish: selection of high affinity "lambodies" that recognize biomedically relevant glycans. ACS Chem Biol. Author manuscript; available in PMC Jan. 1, 20148. Published in final edited form as: ACS Chem Biol. Jan. 18, 2013; 8(1): 152-160.
Hoogenboom (2005) Selecting and screening recombinant antibody libraries. Nat Biotechnol 23(9): 1105-1116.
Schoonbroodt et al., (2008) Engineering antibody heavy chain CDR3 to create a phage display Fab library rich in antibodies that bind charged carbohydrates. J Immunol 181(9): 6213-6221.
Scott et al., (2012) Monoclonal antibodies in cancer therapy. Cancer Immun 12: 14.

(56) References Cited

OTHER PUBLICATIONS

Sheahan et al., (2018) Targeted therapies in the management of locally advanced and metastatic pancreatic cancer: a systematic review. Oncotarget 9(30): 21613-21627.
Sheehan and Marasco (2015) Phage and Yeast Display. Microbiol Spectr 3(1): AID-0028-2014.
Sliwkowski and Mellman (2013) Antibody therapeutics in cancer. Science 341(6151): 1192-1198.
Sormanni et al., (2018) Third generation antibody discovery methods: in silico rational design. Chem Soc Rev 47(24): 9137-9157.
Steentoft et al., (2018) Glycan-directed CAR-T cells. Glycobiology 28(9): 656-669.
Sterner et al., (2016) Perspectives on Anti-Glycan Antibodies Gleaned from Development of a Community Resource Database. ACS Chem Biol 11(7): 1773-1783.
Stowell et al., (2015) Protein glycosylation in cancer. Annu Rev Pathol. Author manuscript; available in PMC Jan. 1, 2016. Published in final edited form as: Annu Rev Pathol. 2015; 10: 473-510.
Takada et al., (1993) Contribution of carbohydrate antigens sialyl Lewis A and sialyl Lewis X to adhesion of human cancer cells to vascular endothelium. Cancer Res 53(2): 354-361.
Tang et al., (2015) Glycan motif profiling reveals plasma sialyl-lewis x elevations in pancreatic cancers that are negative for sialyl-lewis A. Mol Cell Proteomics 14(5): 1323-1333.
Tangvoranuntakul et al., (2003) Human uptake and incorporation of an immunogenic nonhuman dietary sialic acid. Proc Natl Acad Sci U S A 100(21): 12045-12050.
Turtle (2014) Chimeric antigen receptor modified T cell therapy for B cell malignancies. Int J Hematol 99(2): 132-140.
Ugorski and Laskowska (2002) Sialyl Lewis(a): a tumor-associated carbohydrate antigen involved in adhesion and metastatic potential of cancer cells. Acta Biochim Pol 49(2): 303-311.
Waldmann (2019) Human Monoclonal Antibodies: The Benefits of Humanization. In: Steinitz, M. (eds) Human Monoclonal Antibodies. Methods in Molecular Biology, vol. 1904. Humana Press, New York, NY. https://doi.org/10.1007/978-1-4939-8958-4_1. pp. 1-10.
Ward et al., (1989) Binding activities of a repertoire of single immunoglobulin variable domains secreted from *Escherichia coli*. Nature 341(6242): 544-546.
Werther et al., (1996) Sialosyl-Tn antigen as a marker of gastric cancer progression: an international study. Int J Cancer 69(3): 193-199.
Wrammert et al., (2008) Rapid cloning of high-affinity human monoclonal antibodies against influenza virus. Nature 453(7195): 667-671.
Mn and Huang (2012) Recent Development in Carbohydrate Based Anti-cancer Vaccines. J Carbohydr Chem. Author manuscript; available in PMC Feb. 28, 2013. Published in final edited form as: J Carbohydr Chem 31(3): 143-186.
Zanetta et al., (1991) Malignant transformation in hepatocytes is associated with the general increase of glycoprotein ligands specifically binding to the endogenous lectin CSL. Carbohydr Res 213: 117-126.
Zhang et al., (2007) Isolation and characterization of phage-displayed single chain antibodies recognizing nonreducing terminal mannose residues. 2. Expression, purification, and characterization of recombinant single chain antibodies. Biochemistry 46(1): 263-270.
Zhang et al., (2018) Challenges in diagnosis of pancreatic cancer. World J Gastroenterol 24(19): 2047-2060.
Zhao et al., (2009) A herceptin-based chimeric antigen receptor with modified signaling domains leads to enhanced survival of transduced T lymphocytes and antitumor activity. J Immunol 183(9): 5563-5574.
Zhao et al., (2015) Alteration of Electrostatic Surface Potential Enhances Affinity and Tumor Killing Properties of Anti-ganglioside GD2 Monoclonal Antibody hu3F8. J Biol Chem 290(21): 13017-13027.
Zhou et al., (2011) Immunologic mapping of glycomes: implications for cancer diagnosis and therapy. Front Biosci (Schol Ed) 3(4): 1520-1532.
Huang and Liu (2014) Diagnostic value of serum carbohydrate antigen 19-9 in pancreatic cancer: a meta-analysis. Tumour Biol 35(8): 7459-7465.
Hughes et al., (2005) Transfer of a TCR gene derived from a patient with a marked antitumor response conveys highly active T-cell effector functions. Hum Gene Ther. Author manuscript; available in PMC Jun. 12, 2006. Published in final edited form as: Hum Gene Ther. Apr. 2005; 16(4): 457-472.
Humphrey et al., (1996) VMD: visual molecular dynamics. J Mol Graph 14(1): 33-38.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-5883.
Keyel and Reynolds (2018) Spotlight on dinutuximab in the treatment of high-risk neuroblastoma: development and place in therapy. Biologics 13: 1-12.
Kiessling and Grim (2013) Glycopolymer probes of signal transduction. Chem Soc Rev 42(10): 4476-4491.
Kim and Varki (1997) Perspectives on the significance of altered glycosylation of glycoproteins in cancer. Glycoconj J 14(5): 569-576.
Kirwan et al., (2015) Glycosylation-Based Serum Biomarkers for Cancer Diagnostics and Prognostics. Biomed Res Int 2015: 490531.
Kjeldsen et al., (1988) Preparation and characterization of monoclonal antibodies directed to the tumor-associated O-linked sialosyl-2-6 alpha-N-acetylgalactosaminyl (sialosyl-Tn) epitope. Cancer Res 48(8): 2214-2220.
Kletter et al., (2015) Exploring the specificities of glycan-binding proteins using glycan array data and the GlycoSearch software. Methods Mol Biol. Author manuscript; available in PMC Jul. 22, 2015. Published in final edited form as: Methods Mol Biol. 2015; 1273: 203-214.
Kochenderfer and Rosenberg (2013) Treating B-cell cancer with T cells expressing anti-CD19 chimeric antigen receptors. Nat Rev Clin Oncol. Author manuscript; available in PMC Jan. 7, 2019. Published in final edited form as: Nat Rev Clin Oncol. May 2013; 10(5): 267-276.
Koprowski et al., (1979) Colorectal carcinoma antigens detected by hybridoma antibodies. Somatic Cell Genet 5(6): 957-971.
Krug et al., (2007) Targeting Lewis Y (Le(y)) in small cell lung cancer with a humanized monoclonal antibody, hu3S 193: a pilot trial testing two dose levels. J Thorac Oncol 2(10): 947-952.
Lahoud et al., (2021) Tumour markers and their utility in imaging of abdominal and pelvic malignancies. Clin Radiol 76 (2): 99-107.
Langereis et al., (2015) Complexity and Diversity of the Mammalian Sialome Revealed by Nidovirus Virolectins. Cell Rep 11(12): 1966-1978.
La'ulu and Roberts (2007) Performance characteristics of five automated CA 19-9 assays. Am J Clin Pathol 127(3): 436-440.
Lei et al., (2016) Immunocompromised and immunocompetent mouse models for head and neck squamous cell carcinoma. Onco Targets Ther 9: 545-555.
Leviatan Ben-Arye et al., (2017) Profiling Anti-Neu5Gc IgG in Human Sera with a Sialoglycan Microarray Assay. J Vis Exp (125): 56094.
Louis et al., (2011) Antitumor activity and long-term fate of chimeric antigen receptor-positive T cells in patients with neuroblastoma. Blood 118(23): 6050-6056.
Loureiro et al., (2018) Development of a novel target module redirecting UniCAR T cells to Sialyl Tn-expressing tumor cells. Blood Cancer J 8(9): 81.
Mahoney and Jorgensen (2000) A five-site model for liquid water and the reproduction of the density anomaly by rigid, nonpolarizable potential functions. The Journal of Chemical Physics 112: 8910-8922.
Maier et al., (2015) ff14SB: Improving the Accuracy of Protein Side Chain and Backbone Parameters from ff99SB. J Chem Theory Comput 11(8): 3696-3713.

(56) References Cited

OTHER PUBLICATIONS

Maliar et al., (2012) Redirected T cells that target pancreatic adenocarcinoma antigens eliminate tumors and metastases in mice. Gastroenterology 143(5): 1375-1384.e5.
Manimala et al., (2007) High-throughput carbohydrate microarray profiling of 27 antibodies demonstrates widespread specificity problems. Glycobiology 17(8): 17C-23C.
Marcatili et al., (2008) PIGS: automatic prediction of antibody structures. Bioinformatics 24(17): 1953-1954.
Mare and Trinchera (2004) Suppression of beta 1,3galactosyltransferase beta 3Gal-T5 in cancer cells reduces sialyl-Lewis a and enhances poly N-acetyllactosamines and sialyl-Lewis x on O-glycans. Eur J Biochem 271(1): 186-194.
Mata-Fink et al., (2013) Rapid conformational epitope mapping of anti-gp120 antibodies with a designed mutant panel displayed on yeast. J Mol Biol. Author manuscript; available in PMC Sep. 27, 2013. Published in final edited form as: J Mol Biol. Jan. 23, 2013; 425(2): 444-456.
Mellman et al., (2011) Cancer immunotherapy comes of age. Nature 480(7378): 480-489.
Muqbil et al., (2018) Nuclear Export Inhibition for Pancreatic Cancer Therapy. Cancers (Basel) 10(5): 138.
Muthana and Gildersleeve (2014) Glycan microarrays: powerful tools for biomarker discovery. Cancer Biomark 14(1): 29-41.
Padler-Karavani (2014) Aiming at the sweet side of cancer: aberrant glycosylation as possible target for personalized-medicine. Cancer Lett 352(1): 102-112.
Padler-Karavani et al., (2011) Human xeno-autoantibodies against a non-human sialic acid serve as novel serum biomarkers and immunotherapeutics in cancer. Cancer Res 71(9): 3352-3363.
Padler-Karavani et al., (2012) Cross-comparison of protein recognition of sialic acid diversity on two novel sialoglycan microarrays. J Biol Chem 287(27): 22593-22608.
Passerini et al., (2012) The pitfalls of CA19-9: routine testing and comparison of two automated immunoassays in a reference oncology center. Am J Clin Pathol 138(2): 281-287.
Paul and Padler-Karavani (2018) Evolution of sialic acids: Implications in xenotransplant biology. Xenotransplantation 25(6): e12424.
Pepper et al., (2008) A decade of yeast surface display technology: where are we now? Comb Chem High Throughput Screen. Author manuscript; available in PMC May 13, 2009. Published in final edited form as: Comb Chem High Throughput Screen. Feb. 2008; 11(2): 127-134.
Petters et al., (2015) Selection and Characterization of Single Chain Antibody Fragments Specific for Hsp90 as a Potential Cancer Targeting Molecule. Int J Mol Sci 16(8): 19920-19935.
Pettersen et al., (2004) UCSF Chimera—a visualization system for exploratory research and analysis. J Comput Chem 25(13): 1605-1612.
Pinho and Reis (2015) Glycosylation in cancer: mechanisms and clinical implications. Nat Rev Cancer 15(9): 540-555.
Pinthus et al., (2004) Adoptive immunotherapy of prostate cancer bone lesions using redirected effector lymphocytes. J Clin Invest 114(12): 1774-1781.
Ploessl et al., (2016) Dinutuximab: An Anti-GD2 Monoclonal Antibody for High-Risk Neuroblastoma. Ann Pharmacother 50(5): 416-422.
Posey et al., (2016) Engineered CAR T Cells Targeting the Cancer-Associated Tn-Glycoform of the Membrane Mucin MUC1 Control Adenocarcinoma. Immunity 44(6): 1444-1454.
Poty et al., (2019) Leveraging Bioorthogonal Click Chemistry to Improve 225Ac-Radioimmunotherapy of Pancreatic Ductal Adenocarcinoma. Clin Cancer Res 25(2): 868-880.
Pyeon et al., (2015) Abnormally high level of CA-19-9 in a benign ovarian cyst. Obstet Gynecol Sci 58(6): 530-532.
Roe and Cheatham (2013) PTRAJ and CPPTRAJ: Software for Processing and Analysis of Molecular Dynamics Trajectory Data. J Chem Theory Comput 9(7): 3084-3095.
Sadelain et al., (2009) The promise and potential pitfalls of chimeric antigen receptors. Curr Opin Immunol. Author manuscript; available in PMC Aug. 8, 2017. Published in final edited form as: Curr Opin Immunol. Apr. 2009; 21(2): 215-223.
Sadelain et al., (2013) The basic principles of chimeric antigen receptor design. Cancer Discov 3(4): 388-398.
Sadelain et al., (2017) Therapeutic T cell engineering. Nature 545(7655): 423-431.
Safdari et al., (2013) Antibody humanization methods—a review and update. Biotechnol Genet Eng Rev 29: 175-186.
Sanders and Kerr (1999) Lewis blood group and CEA related antigens; coexpressed cell-cell adhesion molecules with roles in the biological progression and dissemination of tumours. Mol Pathol 52(4): 174-178.

* cited by examiner

VH MSA

VL MSA

AcSLe^a

AcSLeX

LeA

LeY

Le^x

Ac-alpha-2-3GalNAc

9-O-AcSLeA

GcSLeA

9-O-GcSLeA

AcSLe[a]

HUMANIZED ANTIBODIES AND FRAGMENTS THEREOF BINDING TO CARBOHYDRATE ANTIGENS AND USES THEREOF

FIELD OF THE INVENTION

The present invention relates to humanized monoclonal antibodies, fragments thereof and CARs comprising same that specifically bind to SLeA carbohydrate antigen, as well as to cells comprising said antibodies or CARs, compositions comprising same and uses thereof.

BACKGROUND OF THE INVENTION

Aberrant glycosylation is one of the hallmarks of cancer resulting in expression of tumor-associated carbohydrate antigens (TACA) that are overexpressed in many types of cancer such as breast, colorectal, ovary, lung, bladder, etc. As a potential cancer cell marker, these glycans constitute an important target for the development of antibodies as therapeutic and diagnostic tools. Currently, there are almost no clinically used anti-glycan antibodies for cancer treatment, and most therapeutic antibodies are against proteins. Anti-carbohydrate antibodies presumably have low affinity compared to those targeting proteins, and some are of low specificity. Both affinity and specificity are two crucial elements in antibody recognition and are important for clinical applications.

Sialyl Lewis A (SLeA), also known as carbohydrate antigen 19-9 (CA19-9), is yet another TACA known to be expressed in pancreatic, colorectal, stomach, liver and gall bladder cancers (Ugorski et al., Acta Biochim Pol. 2002; 49: 303-311). Antibody against SLeA was developed already in 1979 by Koprowski et al. named 1116NS19.9 (Koprowski et al., Somatic Cell Genet. 1979; 5: 957-971). Decades later, this antibody is used in many kits to determine SLeA levels in cancer patients. However, it cannot be used for clinical cancer treatment due to its low affinity.

There are several methods that allow development and improvement of antibodies with high affinity and specificity. These methods include various display systems using phage, ribosome or yeast. Yet, previous attempts to improve affinity of anti-ganglioside antibodies had only limited success (Zhao et al., 2015, The journal of biological chemistry, 290 (21), pp. 13017-13027). Yeast surface display (YSD) is one of the most successful systems for selection of antibodies targeting an antigen of interest. This system takes advantage of the agglutinin mating proteins (Aga1p and Aga2p) that are normally expressed on the yeast cell surface. These agglutinin proteins are expressed at $10^4$-$10^5$ copies per cell, with Aga1p anchored to the yeast cell wall and Aga2p covalently attached to Aga1p through disulfide bonds. In YSD, an antibody fragment is fused to the Aga2p allowing its cell surface presentation in accordance with the expression of Aga1p/Aga2p proteins. Most commonly, single chain Fv (scFv) or Fab antibody fragments are used in YSD. To allow validation of cell surface expression, the antibody fragment carry N-terminal and C-terminal tags. Amon et al., (Cancers 2020, 12(10), 2824) designed yeast surface display to generate and select for therapeutic antibodies against the TACA SLea (CA19-9) in colon and pancreatic cancers.

Antibody humanization involves techniques as framework-homology-based humanization, germline humanization, complementary determining regions (CDR)-homology-based humanization and specificity determining residues grafting (Safdari et al., 2013; Ahmadzadeh et al., 2014; Waldmann, 2019). Nevertheless, selection of mutations that would preserve the original antibody affinity and specificity but with reduced immunogenicity is not at all trivial.

There is an urgent need for therapeutic agents that could aim SLeA with high affinity and specificity and moreover adapted to administration to humans in view of the prevalence of SLeA in many cancer types. Such agents may be used for the treatment of a wide range of cancer types. Yet, despite the facts that anti-SLeA antibody is known for many years, and that the techniques for antibody improvement are abundant, an antibody of high affinity against SLeA has not been developed thus far.

SUMMARY OF THE INVENTION

The present invention is based on the unexpected observation that humanized monoclonal antibodies binding to Sialyl Lewis A (SLeA) glycan not only showed decreased immunogenicity but also improved affinity to the antigen. Amino acid substitutions of framework residues were performed after a thorough examination of the sites and were based not only on similarity to human sequences but also on structural considerations. Humanization of the already mutated analog of native antibody was especially tricky as it required preserving some of the amino acids in the framework that improve the affinity of the analog. Possessing lower immunogenicity, the humanized monoclonal antibodies of the present invention as well as their fragments, conjugates and chimeric antigen receptor (CAR) molecules comprising same avoid, thus, the risk of adverse immune response towards them and therefore safe for in-vivo use in humans.

According to one aspect, the present invention provides a humanized monoclonal antibody (mAb) or a fragment or conjugate thereof that specifically binds to Sialyl Lewis A glycan (SLeA), wherein the humanized mAb or the fragment comprises an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 comprise the amino acid sequence of SEQ ID NOs: 5, the VH-CDR2 comprises an amino acid sequence selected from SEQ ID NOs: 6 and 11, the VH-CDR3 comprises the amino acid sequence of SEQ ID NO: 7, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively. According to some embodiments, the humanized mAb or the fragment, comprises a VH comprising amino acid sequence selected from SEQ ID NO: 12 and 14, and a VL comprising amino acid sequence selected from SEQ ID NO: 13 and 15. According to other embodiments, the VH comprises the amino acid sequence of SEQ ID NO: 12 and the VL comprises the amino acid sequence of SEQ ID NO: 13. According to other embodiments, the VH comprises the amino acid sequence of SEQ ID NO: 14 and the VL comprises the amino acid sequence of SEQ ID NO: 15. According to some embodiments, the fragment is a single-chain variable fragment (scFv). The list of all sequences is provided in the sequence table.

According to another aspect, the present invention provides a humanized monoclonal antibody (mAb) or a functional fragment thereof that specifically binds to Sialyl Lewis A glycan (SLeA), comprising an antigen-binding domain comprising a heavy-chain variable domain (VH) and a light-chain variable domain (VL), wherein the VH comprises amino acid sequence selected from SEQ ID NO: 1 or and 34 in which 10 or more amino acid residues in the framework regions are substituted and the VL comprises amino acid sequence SEQ ID NO: 2 in which 10 or more amino acid residues in the framework regions are substituted. According to some embodiments, the from 10 to 20 amino acid residues in the VH framework regions from 10 to 20 amino acid residues in the VL framework regions are substituted. According to some embodiments, the VH domain comprises an amino acid sequence selected from SEQ ID NO: 1 or and 34 in which 10 or more amino acids at positions selected from positions 3, 5, 18, 19, 40, 42, 72, 79, 80, 81, 89, 90, 94, 95, 110, 114, and 115 are substituted, and the VL domain comprises amino acid sequence SEQ ID NO: 36 in which 10 or more amino acids at positions selected from positions 3, 11, 12, 15, 17, 22, 43, 46, 69, 71, 72, 73, 79, 80, 83, 84, 85, and 104 are substituted. According to some embodiments, the VH domain comprises from 14 to 18 substitutions of the amino acid residues in the framework regions and the VL comprises from 15 to 18 substitutions of the amino acid residues in the framework regions.

According to any one of the above aspects and embodiments, the humanized mAb or the fragment thereof binds SLeA glycan with an equilibrium dissociation constant ($K_D$) from about 0.1 to about 30 nM. According to other embodiments, the selectivity of said antibody or fragment to SLeA glycan is at least 90%. According to some embodiments, the fragment of the humanized antibody of the present invention is a single-chain variable fragment (scFv). According to some embodiments, the scFv comprises VH and VL domains wherein the (i) VH comprises amino acid sequence SEQ ID NO: 12 and the VL comprises amino acid sequence SEQ ID NO: 13 or (ii) the VH comprises amino acid sequence SEQ ID NO: 14 and the VL comprises amino acid sequence SEQ ID NO: 15. According to some embodiments, the scFv comprises an amino acid sequence selected from SEQ ID NO: 22 and 23.

According to one aspect, the present intention provides a conjugate of the humanized mAb or fragment thereof. According to some embodiments, the conjugate comprises an anti-cancer moiety. According to other embodiments, the conjugate comprises a tag or a label.

According to another aspect, the present invention provides a chimeric antigen receptor (CAR) comprising the humanized mAb or the fragment of the present invention. According to some embodiments, the CAR comprises the fragment of the present invention. According to other embodiments, the CAR comprises a VH comprising amino acid sequence SEQ ID NO: 12 and the VL comprising amino acid sequence SEQ ID NO: 13 or the VH comprising amino acid sequence SEQ ID NO: 14 and the VL comprising amino acid sequence SEQ ID NO: 15. According to some embodiments, the fragment is a single chain variable fragment (scFv). According to some embodiments, the present invention provides a CAR comprising the scFv having an amino acid sequence selected from SEQ ID NO: 22 and 23.

According to some embodiments, the CAR comprises a transmembrane domain, a costimulatory domain and an activation domain. According to some embodiments, the transmembrane domain is the transmembrane domain of a receptor selected from CD28 and CD8, or an analog thereof having at least 85% amino acid identity to the original sequence, and/or the costimulatory domain is selected from a costimulatory domain of a protein selected from CD28, 4-1BB, OX40, iCOS, CD27, CD80, and CD70, an analog thereof having at least 85% amino acid identity to the original sequence and any combination thereof, and/or the activation domain is selected from FcRγ and CD3-ζ activation domains.

According to some embodiments, the CAR comprises an scFv sequence comprising the binding site of the humanized monoclonal antibody that binds SLeA a TM domain and a costimulatory domain of CD28, and an activation domain selected from FcRγ and CD3-ζ activation domains. According to specific embodiments, the CAR comprises a scFv comprising amino acid sequence selected from SEQ ID NO: 22 and 23, a TM domain selected from a TM domain of a receptor selected from CD28 and CD8, a costimulatory domain selected from CD28, 4-1BB, OX40, iCOS, CD27, CD80, CD70, an analog thereof and any combination thereof, and an activation domain selected from FcRγ and CD3-ζ activation domain.

According to another aspect, the present invention provides a nucleic acid molecule encoding at least one chain of the humanized monoclonal antibody or fragment thereof or the CAR of the present invention. According to some embodiments, the nucleic acid molecule encodes an amino acid sequence selected from SEQ ID NO: 12, 13, 14, 15, 22, 23, a combination of SEQ ID NO: 12 and SEQ ID NO 13 or 15, and a combination of SEQ ID NO: 14 and SEQ ID NO: 13 or 15. According to other embodiments, nucleic acid molecule comprises a nucleic acid sequence selected from SEQ ID NO: 16, 17, 18, 19, a combination of SEQ ID NO: 16 and SEQ ID NO 17 or 19, and a combination of SEQ ID NO: 18 and SEQ ID NO: 17 or 19, and a conservative variant thereof.

According to another aspect, the present invention provides a nucleic acid construct comprising the nucleic acid of the present invention, operably linked to a promoter.

According to another aspect, the present invention provides a vector comprising the nucleic acid molecule or the nucleic acid construct of the present invention.

According to yet another aspect, the present invention provides a cell comprising the humanized monoclonal antibody or the antibody fragment, the CAR, the nucleic acid molecule, the nucleic acid construct, or the vector of the present invention. According to some embodiments, the cell is a mammalian cell. According to some embodiments, the cell is a lymphocyte. According to some embodiments, the cell is a T-cells. According to some embodiments, the cell is a T-cell comprising the CAR of the present invention. According to some embodiments, the cells are T-cells comprising the nucleic acid molecule of the present invention and expressing or capable of expressing the CAR of the present invention.

According to some embodiments, a lymphocyte engineered to express the CAR of the present invention is provided. According to some embodiments, a T cell engineered to express the CAR described herein is provided. According to additional embodiments, an NK cell engineered to express the CAR described herein is provided.

According to some embodiment, the cell is capable of producing the humanized monoclonal antibody or the antibody fragment of the present invention. According to some aspects, the present invention provides a composition comprising the humanized monoclonal antibodies or antibody fragments of the present invention, the conjugate of the present invention, the CAR or the cells of the present invention and a carrier. According to some embodiments, the composition is a pharmaceutical composition and the carrier is a pharmaceutically acceptable carrier. According to some embodiments, the present invention provides a pharmaceutical composition comprising the CAR of the present invention, and a pharmaceutically acceptable carrier. According to some embodiments, the present invention provides a pharmaceutical composition comprising a plurality of cells of the present invention, and a pharmaceutically acceptable carrier. According to some embodiments, the cells are T-cells. According to some embodiments, the T-cells comprise the CAR of the present invention.

According to some embodiments, the pharmaceutical composition of the present invention is for use in treating cancer. According to some embodiments, the pharmaceutical composition comprising a plurality of T-cells comprising the CAR of the present invention is for use in treating cancer. According to some embodiments, the cancer is selected from breast, lung, ovarian, pancreatic, colon, stomach, oropharyngeal cancer, squamous cell carcinoma, head and neck and gallbladder cancer. According to some particular embodiments, the cancer is selected from lung adenocarcinoma, pancreatic adenocarcinoma, colon adenocarcinoma, Her-2 negative breast carcinoma and pharynx squamous cell carcinoma.

According to yet another aspect, the present invention provides a method for treating cancer in a subject in need thereof comprising administering to said subject a therapeutically effective amount of the monoclonal antibodies or fragments thereof, the conjugate of the present invention, the CAR, the cells or the pharmaceutical composition of the present invention.

BRIEF DESCRIPTION OF DRAWINGS

(FIG. 9B—SLeX; FIG. 9C—LeA; FIG. 9D—LeY; FIG. 9E—LeX; FIG. 9F—Ac-alpha-2-3GalNAc; FIG. 9G—9-O-AcSLeA; FIG. 9H—GcSLeA and FIG. 9I—9-O-GcSLeA.

DETAILED DESCRIPTION OF THE INVENTION

Figure 1A:
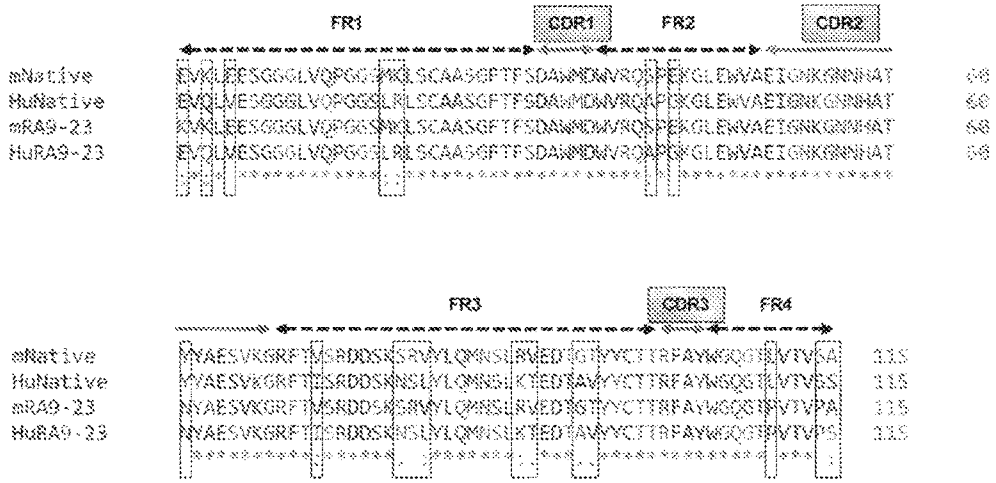
FIG. 1A-1B shows a multiple sequence alignment (MSA) of amino acid sequences of the mouse-derived Native 1116NS19.9 antibody (mNative) and the YSD clone mRA9-23 antibody and their corresponding humanized versions HuNative and HuRA9-23, respectively, showing the VH (FIG. 1A) and VL (FIG. 1B) amino acid sequences.

The present invention provides humanized antibodies and fragments thereof that bind specifically to Sialyl Lewis A glycan (SLeA) and have enhanced affinity to said glycan in comparison to the original antibody on one hand and reduced immunogenicity on the other hand. Specifically, it was shown that humanized version of a mouse-derived Native 1116NS19.9 antibody (mNative) denoted and HuNative and humanized version of a RA9-23 (mutant of 1116NS19.9 antibody) denoted as HuRA9-23 demonstrated a significantly lower immunogenicity than the original antibodies (about 3.5 and 4 times lower immunogenicity, respectively). In addition, the humanized antibodies and scFv thereof have higher affinity than the initial antibodies to SLeA glycan. According to one aspect, the present invention provides a humanized monoclonal antibody (mAb) or a fragment thereof that specifically binds to Sialyl Lewis A glycan (SLeA), wherein the mAb of the fragment comprises an antigen-binding domain comprising a heavy-chain variable domain (VH) and a light-chain variable domain (VL), wherein the VH comprises amino acid sequence SEQ ID NO: 1 in which 10 or amino acid residues in the framework regions are substituted and the VL comprises amino acid sequence SEQ ID NO: 2 in which 10 or more amino acid residues in the framework regions are substituted. According to some embodiments, the present invention provides a humanized monoclonal antibody (mAb) that specifically binds to Sialyl Lewis A glycan (SLeA) or a functional fragment of the antibody, comprising an antigen binding domain comprising a heavy-chain variable domain (VH) and a light-chain variable domain (VL), wherein the VH comprises amino acid sequence SEQ ID NO: 1 in which from 10 to 26 amino acid residues in the framework regions are substituted and the VL comprises amino acid sequence SEQ ID NO: 2 in which from 10 to 26 amino acid residues in the framework regions are substituted. According to some embodiments, VH comprises three CDRs, wherein the VH-CDRs 1, 2 and 3 comprise amino acid sequences SEQ ID NOs: 5, 6 and 7, respectively. According to other embodiments, the VL comprises three CDRs, wherein the VL-CDRs 1, 2 and 3 comprise amino acid sequences SEQ ID NOs: 8, 9 and 10, respectively. According to yet another embodiment, the VH-CDRs 1, 2 and 3 comprise amino acid sequences SEQ ID NOs: 36, 37 and 7, respectively. According to some embodiments, the VH-CDR2 comprises one non-conservative substitution at position 61 of SEQ ID NO: 1. According to some embodiments, the substitution in the VH CDR2 is at position 61 of SEQ ID NO: 1 for Asn. According to other embodiments, the substitution in the VH CDR2 is at position 61 of SEQ ID NO: 1 for Gln. According to some embodiments, the humanized mAb or the fragment comprises a VH comprising amino acid sequence SEQ ID NO: 34 in which 10 or amino acid residues in the framework regions are substituted. According to some embodiments, the present invention provides a humanized monoclonal antibody (mAb) or a functional fragment thereof that specifically binds to Sialyl Lewis A glycan (SLeA), comprising an antigen binding domain comprising a heavy-chain variable domain (VH) and a light-chain variable domain (VL), wherein the VH comprises amino acid sequence SEQ ID NO: 34 in which from 10 to 26 amino acid residues in the framework regions are substituted and the VL comprises amino acid sequence SEQ ID NO: 2 in which from 10 to 26 amino acid residues in the framework regions are substituted. According to some embodiments, the VH comprises amino acid sequence SEQ ID NO: 34 in which from 11 to 24, from 12 to 22, from 13 to 20, from 14 to 18 or from 15 to 18 of amino acid residues in the framework regions are substituted. According to some embodiments, the VH comprises amino acid sequence SEQ ID NO: 34 in which from 11 to 24, from 12 to 22, from 13 to 20, from 14 to 18 or from 15 to 18 of amino acid residues in the framework regions are substituted. According to some embodiments, the VL comprises amino acid sequence SEQ ID NO: 2 in which from 11 to 24, from 12 to 22, from 13 to 20 or from 14 to 18 of amino acid residues in the framework regions are substituted. According to some embodiments, the VH comprises amino acid sequence SEQ ID NO: 1 or 34 in which from 11 to 24, from 12 to 22, from 13 to 20, from 14 to 18 or from 15 to 18 of amino acid residues in the framework regions are substituted and the VL comprises amino acid sequence SEQ ID NO: 2 in which from 11 to 24, from 12 to 22, from 13 to 20 or from 14 to 18 of amino acid residues in the framework regions are substituted. According to some embodiments, substitutions in the framework regions of VH domain are at 10 positions or more of positions 3, 5, 18, 19, 40, 42, 72, 79, 80, 81, 89, 90, 94, 95, 110, 114, 115 of SEQ ID NO: 1 or 34. According to some embodiments, substitutions in the framework regions of VH domain are at 11, 12, 13, 14, 15, 16 or 17 positions of positions 3, 5, 18, 19, 40, 42, 72, 79, 80, 81, 89, 90, 94, 95, 110, 114, 115 of SEQ ID NO: 1 or 34.

According to other embodiments, substitutions in the framework regions of VL domain are at 10 positions or more of positions 3, 11, 12, 15, 17, 22, 43, 46, 69, 71, 72, 73, 79, 80, 83, 84, 85, and 104 of SEQ ID NO: 2. According to some embodiments, substitutions in the framework regions of VH domain are at 11, 12, 13, 14, 15, 16, 17 or 18 positions of positions 33, 11, 12, 15, 17, 22, 43, 46, 69, 71, 72, 73, 79, 80, 83, 84, 85, and 104 of SEQ ID NO: 2.

According to some embodiments, substitutions in the framework regions of VH domain are at 14, 15, 16 or 17 positions of positions 3, 5, 18, 19, 40, 42, 72, 79, 80, 81, 89, 90, 94, 95, 110, 114, and 115 of SEQ ID NO: 1 or 34 and substitutions in the framework regions of VL domain are at 14, 15, 16, 17 or 18 positions of positions 33, 11, 12, 15, 17, 22, 43, 46, 69, 71, 72, 73, 79, 80, 83, 84, 85, and 104 of SEQ ID NO: 2. According to some embodiments, the present invention provides a humanized mAb or a fragment thereof that specifically binds to SLeA, comprising an antigen binding domain comprising a VH and a VL, wherein the VH comprises an amino acid sequence selected from SEQ ID NO: 1 or 34 in which 10 or more of amino acid residues at positions selected from 3, 5, 18, 19, 40, 42, 72, 79, 80, 81, 89, 90, 94, 95, 110, 114, and 115 are substituted and the VL comprises amino acid sequence SEQ ID NO: 2 in which 10 or more of amino acid residues at positions selected from 3, 11, 12, 15, 17, 22, 43, 46, 69, 71, 72, 73, 79, 80, 83, 84, 85, and 104. According to some embodiments, from 14 to 17 amino acids are substituted in amino acid sequence selected from SEQ ID NO: 1 or 34. According to some embodiments, from 14 to 18 amino acids are substituted in the amino acid sequence SEQ ID NO: 2. According to some embodiments, all amino acid at positions 3, 5, 18, 19, 40, 42, 72, 79, 80, 81, 89, 90, 94, 95, 110, 114, and 115 of amino acid sequence selected from SEQ ID NO: 1 or 34 and all amino acid residues at positions selected from 3, 11, 12, 15, 17, 22, 43, 46, 69, 71, 72, 73, 79, 80, 83, 84, 85, and 104 of amino acid sequence SEQ ID NO: 2 are substituted.

According to some embodiment, the present invention provides a humanized monoclonal antibody (mAb) or a functional fragment thereof that specifically binds to Sialyl Lewis A glycan (SLeA), comprising an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively.

According to some embodiments, the VH of the humanized mAb or the fragment comprises amino acid sequence SEQ ID NO: 12. According to other embodiments, the VH of the humanized mAb or the fragment comprises amino acid sequence SEQ ID NO: 14. According to one embodiments, the VL of the humanized mAb or the fragment comprises amino acid sequence SEQ ID NO: 13. According to another embodiments, the VL of the humanized mAb or the fragment comprises amino acid sequence SEQ ID NO:15. According to some embodiments, the VH comprises amino acid sequence selected from SEQ ID NO: 12 and the VL comprises amino acid sequence selected from SEQ ID NO: 13 and 15. According to other embodiments, the VH comprises amino acid sequence selected from SEQ ID NO: 14 and the VL comprises amino acid sequence selected from SEQ ID NO: 13 and 15. According to one embodiment, the VH comprises amino acid sequence SEQ ID NO: 12 and the VL comprises amino acid sequence SEQ ID NO: 13. According to yet another embodiment, the VH comprises amino acid sequence SEQ ID NO: 14 and the VL comprises amino acid sequence SEQ ID NO: 15. According to one embodiment, the VH comprises amino acid sequence SEQ ID NO: 12 and the VL comprises amino acid sequence SEQ ID NO: 15. According to yet another embodiment, the VH comprises amino acid sequence SEQ ID NO: 14 and the VL comprises amino acid sequence SEQ ID NO: 13.

The terms “antibody”, “antibodies” and “Ab” are used here interchangeably in the broadest sense and include monoclonal antibodies (including full length or intact monoclonal antibodies), polyclonal antibodies, multivalent antibodies, multi-specific antibodies (e.g., bi-specific antibodies), and antibody fragment long enough to exhibit the desired biological activity.

Antibodies, or immunoglobulins, comprise two heavy chains linked together by disulfide bonds and two light chains, each light chain being linked to a respective heavy chain by disulfide bonds in a “Y” shaped configuration. Proteolytic digestion of an antibody yields Fv (Fragment variable) and Fc (Fragment crystalline) domains. The term “antigen binding portion”, “antigen binding region”, “antigen binding site” and “antigen binding domain” are used herein interchangeably and refer to one or more fragments of an antibody that retain the ability to specifically bind to an antigen. The antigen binding domains, Fab, include regions where the polypeptide sequence varies. The term $F(ab')_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains of the light and heavy chains have the same general structure and each domain comprises four framework regions, whose sequences are relatively conserved, joined by three hyper-variable domains known as complementarity determining regions (CDRs). These domains contribute to the specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa (κ) or lambda (λ)) found in all antibody classes. The term “paratope” refers to the antigen binding site of an antibody or fragment thereof.

The terms “monoclonal antibody” and “mAb” are used herein interchangeably and refer to an antibody obtained from a population of substantially homogeneous antibodies, i.e., the individual antibodies comprising the population are identical except for possible naturally occurring mutations that may be present in minor amounts.

Monoclonal antibodies (mAbs) are highly specific, being directed against a single antigen. Furthermore, in contrast to polyclonal antibody preparations that typically include different antibodies directed against different determinants (epitopes), each monoclonal antibody is directed against a single determinant on the antigen. The modifier “monoclonal” is not to be construed as requiring production of the antibody by any particular method. mAbs may be obtained by methods known to those skilled in the art. For example, the monoclonal antibodies to be used in accordance with the present invention may be made by the Hybridoma method or may also be isolated from phage antibody libraries.

The term “humanized antibodies” refers to antibodies from non-human species (e.g. murine antibodies) which amino acid sequences have been modified to increase their similarity to antibody variants produced naturally in humans. The process of “humanization” is usually applied to monoclonal antibodies developed for administration to humans, and performed when the process of developing a specific antibody involves generation in a non-human immune system (such as in mice). The protein sequences of antibodies produced in this way are distinct from antibodies occurring naturally in humans, and are therefore immunogenic when administered to human patients. Humanized antibodies are considered distinct from chimeric antibodies, which have protein sequences similar to human antibodies, but carry large stretches of non-human protein. In the present invention, during humanization framework regions of mouse antibody specific to SLeA glycan and its analog having improved affinity to the SLeA were mutated. This was done using rational consideration of each and every site using structural modelling and experimental information. Moreover, considering that the analog of mouse antibody already had some modifications in comparison to native antibodies, these modifications were kept in order to preserve activity.

The terms “fragment”, “functional fragment” and “antibody fragment” are used herein interchangeably and refer to only a portion of an intact antibody, generally including an antigen-binding site of the intact antibody and thus retaining the ability to bind antigen. The term refers to the antibody as well as to the analog or variant of said antibody. The antibody fragment according to the teaching of the present invention is a function fragment, i.e. preserves the function of the intact antibody. Examples of antibody fragment encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v)

the Fv fragment having the VL and VH domains of a single arm of an antibody; (vi) the dAb fragment (Ward et al., Nature 1989, 341, 544-546) which consists of a VH domain; (vii) isolated CDR regions; (viii) $F(ab')_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions. According to some embodiments, the functional fragment is a scFv.

The terms "light chain variable region", "VL" and "VL" are used herein interchangeably and refer to a light chain variable region of an antibody capable of binding to SLeA glycan. The terms "heavy chain variable region", "VH" and "VH" are used herein interchangeably and refer to a heavy chain variable region of an antibody capable of binding to SLeA glycan.

As used herein, the term "CDR" refers to the complementarity determining region within antibody variable sequences. There are three CDRs in each one of the variable regions of the heavy chain and the light chain, which are designated CDR1, CDR2 and CDR3 (or specifically VH CDR1, VH CDR2, VH CDR3, VL CDR1, VL CDR2, and VL CDR3), for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. Still other CDR boundary definitions may not strictly follow one of the known systems, but will nonetheless overlap with the Kabat CDRs, although they may be shortened or lengthened in light of prediction or experimental findings that particular residues or groups of residues or even entire CDRs do not significantly impact antigen binding. Determination of CDR sequences from antibody heavy and light chain variable regions can be made according to any method known in the art, including but not limited to the methods known as KABAT, Chothia and IMGT. The selected set of CDRs may include sequences identified by more than one method, namely, some CDR sequences may be determined using KABAT and some using IMGT. According to one embodiment, the CDRs are defined using KABAT method.

As used herein, the terms "framework", "framework region" or "framework sequence" refer to the remaining sequences of a variable region minus the CDRs. Because the exact definition of a CDR sequence can be determined by different systems, the meaning of a framework sequence is subject to correspondingly different interpretations. The six CDRs also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represent two or more of the four sub-regions constituting a framework region.

According to some embodiments, the antibody fragment is a single chain variable fragment (scFv) being a composite polypeptide having antigen binding capabilities and comprising amino acid sequences homologous or analogous to the variable regions of an immunoglobulin light and heavy chain i.e. linked $V_H$-$V_L$, $V_L$-$V_H$ or single chain Fv (scFv).

According to some embodiments, the terms "antibody" or "antibodies" collectively refer to intact antibodies, i.e. humanized monoclonal antibodies (mAbs) and analogs thereof, as well as proteolytic fragments thereof, such as the Fab or $F(ab')_2$ fragments and scFv.

The terms "binds specifically" or "specific for" with respect to an antigen-binding domain of an antibody or of a fragment thereof refers to an antigen-binding domain which recognizes and binds to a specific antigen, but does not substantially recognize or bind other molecules, e.g. in a sample or in vivo. The term encompasses that the antigen-binding domain binds to its antigen with high affinity and binds other antigens with low affinity. An antigen-binding domain that binds specifically to an antigen from one species may bind also to that antigen from another species. This cross-species reactivity is not contrary to the definition of that antigen-binding domain as specific.

Figure 10A:
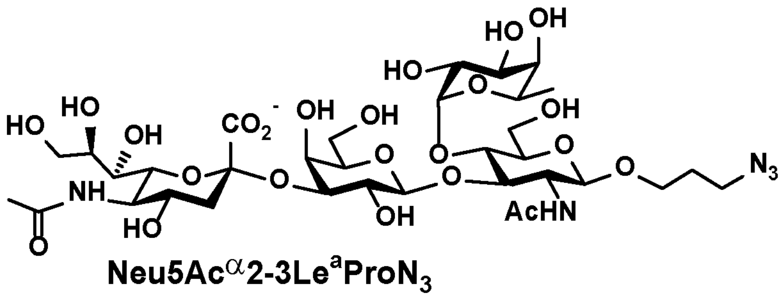
FIG. 10A-10B show the structure (FIG. 10A) and the schematic representation (FIG. 10B) of Sialyl Lewis A glycan.
Figure 10B:
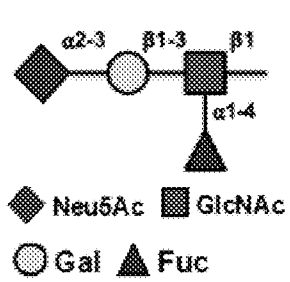

The terms "Sialyl Lewis A glycan", "SLe$^a$", SLe$^A$" and "SLeA" are used herein interchangeably and refer to Siaα2-3Galβ1-3[Fucα-4]GlcNAc tetrasaccharide carbohydrate also known as antigen 19-9 (CA19-9), and having the structure as presented in FIG. 10A and schematically presented in FIG. 10B. This tetrasaccharide can be conjugated to different underlying structures such as carbohydrate(s), protein, lipid, synthetic linker(s) or scaffold(s).

The term "non-conservative substitutions" as used herein shall mean the substitution of one amino acid by another which has different properties (i.e, charge, polarity, hydrophobicity, structure). Examples of the non-conservative substitution include substitution of a hydrophobic residue such as isoleucine, valine, leucine, alanine, phenylalanine, tyrosine, tryptophan or methionine for a polar or charged amino acid residue such as lysine, arginine, glutamine, asparagine, aspartate, glutamate, histidine serine, threonine, or cysteine. Likewise, the present disclosure contemplates the substitution of a charged amino acid such as lysine, arginine, histidine, aspartate and glutamate for an uncharged residue including, but not limited to serine, threonine, asparagine, glutamine, or glycine. In certain embodiments, non-conservative substitutions include substitution of an uncharged, hydrophobic amino acid such as leucine with a charged amino acid, such as aspartic acid, lysine, arginine, or glutamate.

According to any one of the above embodiments, the functional fragment is a scFv. Thus, according to some embodiments, the present invention provides a single chain variable fragment comprising an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively. According to some embodiments, the present invention provides an scFv wherein the VH comprises amino acid sequence selected from SEQ ID NO: 12 and 14, and the VL comprises amino acid sequence selected from SEQ ID NO: 13 and 15. According to one embodiment, the VH of the scFv comprises amino acid sequence SEQ ID NO: 12 and the VL comprises amino acid sequence SEQ ID NO: 13. According to yet another embodiment the VH of the scFv comprises amino acid sequence SEQ ID NO: 14 and the VL comprises amino acid sequence SEQ ID NO: 15. According to some embodiments, the VH and the VL domains of the scFv of the present invention are linked by a spacer to form a single chain variable fragment (scFv). The terms "linker" or "spacer" relate to any peptide capable of connecting two domains of the scFv or two distinguishable sections of the scFv such as variable domains with its length depending on the kinds of variable domains to be connected. According to some embodiments, the linker comprises an amino acid sequence comprising from 1 to 10 repetitions of amino acid sequence SEQ ID NO: 35. According to some embodiment, the linker comprises 2, 3, or 4 repetitions of amino acid sequence SEQ ID NO: 35. According to one embodiment, the linker comprises amino acid sequence SEQ ID NO: 20. According to any one of the above embodiments, the VL and VH domains in the scFv may be placed in any order, such as N'-VH-VL-C' or N'-VL-VH-C'. The VH and VL domains may be linked by a linker. According to one embodiment, the scFv comprises amino acid sequence selected from SEQ ID NO: 22. According to another embodiment, the scFv comprises amino acid sequence selected from SEQ ID NO: 23.

According to any one of the aspects and embodiments of the invention, when referring to antibody or fragment thereof, the terms "comprising the amino acid sequence set forth in SEQ ID NO: X", "comprising SEQ ID NO: X" and "having SEQ ID NO: X" are used herein interchangeably. The terms "consisting of the amino acid sequence set forth in SEQ ID NO: X", "consisting of SEQ ID NO: X" and "of SEQ ID NO: X" are used herein interchangeably.

The same rule holds for nucleic acid sequence. Thus, the terms "nucleic acid comprising the nucleic acid sequence set forth in SEQ ID NO: X", "nucleic acid comprising SEQ ID NO: X" and "nucleic acid having SEQ ID NO: X" are used herein interchangeably.

The terms "nucleic acid consisting of the nucleic acid sequence set forth in SEQ ID NO: X", "nucleic acid consisting of SEQ ID NO: X" and "nucleic acid of SEQ ID NO: X" are used herein interchangeably.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" also encompasses the meaning of "consisting of" and "consisting essentially of", and may be substituted by these terms. Thus, according to any aspect or embodiment of the present invention, the statement such as VH or VL comprising amino acid sequence X has also the meaning that the VH or VL consists of amino acid sequence X.

Thus, according to some embodiments, the present invention provides a humanized mAb or an antibody fragment, comprising a VH domain consisting of amino acid sequence SEQ ID NO: 12 or 14. According to another embodiment, the VL domain of the humanized mAb or the fragment of the present invention consists of amino acid sequence SEQ ID NO: 13 or 15. According to yet another embodiment, the present invention provides a humanized monoclonal antibody comprising VH domain consisting of amino acid sequence SEQ ID NO: 12 and a VL domain consisting of amino acid sequence SEQ ID NO: 13. According to one embodiment, the present invention provides a humanized monoclonal antibody comprising VH domain consisting of amino acid sequence SEQ ID NO: 14 and a VL domain consisting of amino acid sequence SEQ ID NO: 15. According to a further embodiment, the present invention provides a functional fragment of a humanized antibody comprising a VH domain consisting of amino acid sequence SEQ ID NO: 12 and a VL domain consisting of amino acid sequence SEQ ID NO: 14. According to a further embodiment, the present invention provides a functional fragment of a humanized antibody comprising a VH domain consisting of amino acid sequence SEQ ID NO: 13 and a VL domain consisting of amino acid sequence SEQ ID NO: 15. According to one embodiment, the functional fragment is an scFv. According to one embodiment, the scFv consists of the amino acid SEQ ID NO: 22. According to another embodiment, the scFv consists of the amino acid SEQ ID NO: 23.

According to any one of the above embodiments, the mAb or the fragment further comprises one or more conservative substitution in the framework(s) of the VH domain and/or VL domain, i.e. being a conservative analog of the humanized mAb or of the functional fragment of the present invention, wherein the substitution is not at any one of positions 3, 5, 18, 19, 40, 42, 72, 79, 80, 81, 89, 90, 94, 95, 110, 114, and 115 of SEQ ID NO: 1, 34, 12 or 14 and wherein the substitution is not at any one of positions 3, 11, 12, 15, 17, 22, 43, 46, 69, 71, 72, 73, 79, 80, 83, 84, 85, and 104 of SEQ ID NO: 2, 13 or 15. The amino acid sequence of such VH analog has at least 90% sequence identity to SEQ ID NO: 1, 34, 12 or 14 and the VL domain of such analog has at least 90% sequence identity to SEQ ID NO: 2, 13 or 15. According to some embodiments, the VH domain of the analog has at least 91%, at least 92%, at least 93%, at least 94%, at least 95%, at least 96%, at least 97%, at least 98%, at least 99% sequence identity to SEQ ID NO: 1, 34, 12 or 14. According to other embodiments, the VL domain of the analog has at least 91%, at least 92%, at least 93%, at least 94%, at least 95%, at least 96%, at least 97%, at least 98%, at least 99% sequence identity to SEQ ID NO: 2, 13 or 15.

The terms "analog" and "functional analog" refer to polypeptide, peptide or protein which differs by one or more amino acid alterations (e.g., substitutions, additions or deletions of amino acid residues) from the original sequence, having at least 85% sequence identity to the original sequence and still maintains the properties and the functionality of the parent polypeptide, peptide or protein. According to one embodiment, the analog has about 85% to about 99%, about 87% to about 98% or about 90% to about 95%, or about 95% to 99% sequence identity to the original peptide.

The term "conservative substitution" as used herein denotes the replacement of an amino acid residue by another, without altering the overall conformation and biological activity of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, according to one table known in the art, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W).

According to any one of the above embodiments, the humanized mAb or the fragment of the present invention binds SLeA glycan with an equilibrium dissociation constant ($K_D$) of about 0.01 to 100 nM. According to one embodiment, the mAb or the fragment of the present invention binds SLeA glycan with an equilibrium dissociation constant ($K_D$) of about 0.05 to 80 nM, about 0.075 to 60 nM. According to one embodiment, the mAb or the fragment of the present invention binds SLeA glycan with an equilibrium dissociation constant ($K_D$) of about 0.1 to 30 nM. According to some embodiment, the mAb or the fragment of the present invention binds SLeA glycan with an equilibrium dissociation constant ($K_D$) of about 0.1 to 20 nM. According to one embodiment, the mAb or the fragment of the present invention binds SLeA glycan with an equilibrium dissociation constant ($K_D$) of about 0.1 to 10 nM. According to some embodiments, the scFv of the present invention has $K_D$ of from 1 to 25 nM. According to some embodiments, the mAb of the present invention has $K_D$ of from 0.01 to 5 nM. According to some embodiments, the mAb of the present invention has $K_D$ of from 0.01 to 30 nM. According to some embodiments, the mAb of the present invention has $K_D$ of from 0.05 to 30 nM.

The term "$K_D$", as used herein, is intended to refer to the dissociation constant of a particular antibody-antigen interaction. $K_D$ is calculated by $k_a/k_d$. The term "$k_{on}$" or "$k_a$", as used herein, is intended to refer to the on rate constant for association of an antibody to the antigen to form the antibody/antigen complex. The term "$k_{off}$" or "$k_d$", as used herein, is intended to refer to the off rate constant for dissociation of an antibody from the antibody/antigen complex.

According to some embodiments, the inhibitions constant (Ki) of the humanized mAb of the present invention or of the fragment thereof is from 30 to 500 nM, from 40 to 300 nM, from 50 to 200 nM or from 50 to 150 nM.

According to any one of the above embodiments, the selectivity (i.e. selectivity in cross reaction) of the humanized mAb or the fragment of the present invention to SLeA glycan is at least 90%. As used herein, the term "selectivity" for an antibody refers to an antibody that binds to a certain carbohydrate antigen but not to closely structurally related carbohydrates. The selectivity is identified as known in the art, e.g. as described in the Examples. According to another embodiment, the selectivity in cross reaction is at least 95% or at least 98%. According to one embodiment, the closely structurally related carbohydrate is SLeX. According to one embodiment, the selectivity in cross reaction to SLeA glycan versus SLeX glycan is at least 97% or at least 98%.

According to some embodiments, the humanized mAbs or fragments thereof have lower recognition by pooled human IgG antibodies than the original monoclonal antibodies. Interestingly, as shown in the Examples mRA9-23 mutant has lower immunogenicity (about 35% reduction) than the native mouse antibody as defined in the present invention (mNative). Humanization of mNative and mRA9-23 antibodies and scFvs thereof significantly reduced immunogenicity. As shown in the Examples, HuNative has about 74% lower immunogenicity compared to mNative, and HuRA9-23 has about 78% lower immunogenicity compared with mRA9-23 (FIG. 8). In other words, immunogenicity of humanized RA9-23 antibody or scFv thereof is about 4 limes lower than that of mRA9-23, and humanized native antibody of the present invention or scFv thereof is about 3.5 limes lower that of the native antibody.

According to some embodiments, the humanized antibody or fragment there of the present invention has from 40 to 90% lower immunogenicity as compared to mNative, as tested according to the teaching of the present invention. Immunogenicity of humanized antibody clones can be evaluated by analysis of scFv recognition by pooled human IgG obtained from thousands of human donors (IVIg; Gamma Gard). For this purpose, IVIg was first pre-cleared from anti-yeast reactivity by serial incubations with yeast cells, then binding to scFv-expressing yeast cells was examined by FACS. Expression of scFv on yeast can be examined by mouse-anti-c-Myc and pooled human IgG binding detected with anti-human IgG, and double positive labeling of scFv-expressing yeast cells was examined. The ratio of positive/negative IVIg labeling indicate that that IVIg had reduced binding to scFv. According to some embodiments, the humanized antibody or fragment there of the present invention has from 40 to 90% lower immunogenicity as compared to mNative. According to some embodiments, the humanized antibody or fragment there of the present invention has from 60 to 90% lower immunogenicity as compared to mNative. According to some embodiments, the humanized antibody or fragment there of the present invention has from 70 to 90% lower immunogenicity as compared to mNative. According to some embodiments, the humanized antibody or fragment there comprising amino acid sequence SEQ ID NO: 12 and 13, or SEQ ID NO: 22 has from 70 to 90% lower immunogenicity than mNative. According to some embodiments, the humanized antibody or fragment there comprising amino acid sequence SEQ ID NO: 15 and 14, or SEQ ID NO: 23 has from 70 to 90% lower immunogenicity than mNative. According to some embodiments, the humanized antibody or fragment there comprising amino acid sequence SEQ ID NO: 15 and 14, or SEQ ID NO: 23 has from 70 to 90% lower immunogenicity than RA9-23.

According to some embodiments, the humanized mAb or the fragment of the present invention binds SLeA glycan with an equilibrium dissociation constant ($K_D$) of about 0.01 to 30 nM and lower immunogenicity (e.g. recognition by pooled human IgG antibodies) than the original monoclonal antibodies, e.g. from 50 to 90% lowered binding of from 60 to 80% lower binding. All the values related to $K_D$ and immunogenicity as defined above apply herein as well.

According to some embodiments, the humanized mAb or the fragment of the present invention binds SLeA glycan with an equilibrium dissociation constant ($K_D$) of about 0.01 to 100 nM and has selectivity to SLeA glycan in cross reaction versus SLeX glycan of at least 97% or at least 98%.

According to any one of the above embodiments, the heavy chain of the humanized mAb or the fragment of the present invention has a structure selected from the of IgG, IgA, IgD, IgE or IgM class (type). According to one embodiment, the mAb has an IgG structure. According to one embodiment, the heavy chain constant region is selected from the group consisting of: human IgG1, human IgG2, human, IgG3, human IgG4, mouse IgG1, mouse IgG2a, mouse IgG2b, mouse IgG3. According to other embodiments, the light chain constant region is selected from kappa and lambda.

According to some embodiments, the present invention provides a conjugate of the humanized mAb or of the fragment of the present invention. The term "conjugate" as used herein refers to the association of an antibody or a fragment thereof with another moiety. According to some embodiments, the moiety is a tag or label and the conjugate comprises a label. The terms "tag" or "label" refer to a moiety which is attached, conjugated, linked or bound to, or associated with a compound such as an antibody or antibody fragment of the present invention and which may be used as a means of, for example, identifying, detecting and/or purifying the compound. Tags or labels include haemagglutinin tag, myc tag, poly-histidine tag, protein A, glutathione S transferase, Glu-Glu affinity tag, substance P, FLAG peptide, biotin and streptavidin binding peptide, enzyme, GFP, and rodamine. According to some embodiments, the label is a fluorescent label.

The term "moiety" as used herein refers to a part of a molecule, which lacks one or more atom(s) compared to the corresponding molecule. The term "moiety", as used herein, further relates to a part of a molecule that may include either whole functional groups or parts of functional groups as substructures.

According to some embodiments, the moiety is an active moiety. The term "active agent" and "active moiety" are used herein interchangeably and refer to an agent that has biological activity, pharmacologic effects and/or therapeutic utility.

According to some embodiments, the conjugate comprises the humanized mAb or fragment thereof and an active moiety. According to some embodiments, the active moiety is an anti-cancer active moiety. According to some embodiments, the active moiety is an anti-cancer moiety. The term "anti-cancer", "anti-neoplastic" and "anti-tumor" when referred to a compound, an agent or a moiety are used herein interchangeably and refer to a compound, drug, antagonist, inhibitor, or modulator such as immunomodulatory having anticancer properties or the ability to inhibit or prevent the growth, function or proliferation of and/or causing destruction of cells," and in particular tumor cells. Therapeutic agents suitable in an anti-neoplastic composition for treating cancer include, but not limited to, chemotherapeutic agents, radioactive isotopes, toxins, cytokines such as interferons, immunostimulating agents, immunomodulating agents and antagonistic agents targeting cytokines, cytokine receptors or antigens associated with tumor cells. In some embodiments, an anti-cancer agent is a chemotherapeutic. Thus according to some embodiments, the present invention provides a conjugate of the humanized mAb of the present invention or of a fragment thereof and an anti-cancer moiety such as chemotherapeutic agents, radioactive isotopes, toxins, cytokines such as interferons, immunostimulating agents, immunomodulating agents and antagonistic agents targeting cytokines, cytokine receptors or antigens associated with tumor cells. According to another embodiment, the present invention provides a conjugate of the fragment of the mAb of the present invention and the anti-cancer moiety.

According to any one of the above embodiments, the antibodies or the fragments thereof are isolated.

According to another aspect, the present invention provides a chimeric antigen receptor (CAR) comprising the humanized mAb or the fragment thereof of the present invention as described in any one of the above aspects and embodiments. All embodiments and definitions used in any one of the above aspects and embodiments apply and encompassed herein as well. According to some embodiments, the CAR comprises an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively. According to another embodiment, the CAR comprises an antigen binding domain comprising a heavy-chain variable domain (VH) and a light-chain variable domain (VL), wherein the VH comprises amino acid sequence selected from SEQ ID NO: 1 or 34 in which 10 or more amino acid residues in the framework regions are substituted and the VL comprises amino acid sequence SEQ ID NO: 2 in which 10 or more amino acid residues in the framework regions are substituted. According to some embodiments, the CAR comprises a scFv of the present invention. According to some embodiments, the CAR comprises a scFv comprising an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively. According to some embodiments, the present invention provides a CAR comprising an scFv wherein the VH comprises amino acid sequence selected from SEQ ID NO: 12 and 14, and the VL comprises amino acid sequence selected from SEQ ID NO: 13 and 15. According to one embodiment, the VH of the scFv comprises amino acid sequence SEQ ID NO: 12 and the VL comprises amino acid sequence SEQ ID NO: 13. According to yet another embodiment the VH of the scFv comprises amino acid sequence SEQ ID NO: 14 and the VL comprises amino acid sequence SEQ ID NO: 15. According to one embodiment, the CAR comprises a scFv comprising the amino acid sequence selected from SEQ ID NO: 22. According to another embodiment, the CAR comprises a scFv comprising the amino acid sequence selected from SEQ ID NO: 23. According to some embodiments, the present invention provides a CAR comprising an scFv wherein the VH consists of an amino acid sequence selected from SEQ ID NO: 12 and 14, and the VL consists of amino acid sequence selected from SEQ ID NO: 13 and 15. According to one embodiment, the VH of the scFv consists of amino acid sequence SEQ ID NO: 12 and the VL consists of amino acid sequence SEQ ID NO: 13. According to yet another embodiment the VH of the scFv consists of amino acid sequence SEQ ID NO: 14 and the VL consists of amino acid sequence SEQ ID NO: 15. According to one embodiment, the CAR comprises a scFv consisting of the amino acid sequence selected from SEQ ID NO: 22. According to another embodiment, the CAR comprises a scFv consisting of the amino acid sequence selected from SEQ ID NO: 23.

The terms "chimeric antigen receptor" or "CAR" are used herein interchangeably and refer to engineered recombinant polypeptide or receptor which are grafted onto cells and comprises at least (1) an extracellular domain comprising an antigen-binding region, e.g., a single chain variable fragment of an antibody or a whole antibody, (2) a transmembrane domain to anchor the CAR into a cell, and (3) one or more cytoplasmic signaling domains (also referred to herein as "an intracellular signaling domains"). The extracellular domain comprises an antigen binding domain (ABD) and optionally a spacer or hinge region. The antigen binding domain of the CAR targets a specific antigen. The targeting regions may comprise full length heavy chain, Fab fragments, or single chain variable fragment (scFvs).

The terms "antigen binding portion", "antigen binding domain" and "ABD" refer to one or more fragments of an antibody that retain the ability to specifically bind to an antigen. It has been shown that the antigen binding function of an antibody can be performed by fragments of a full-length antibody. Such ABD may also be bispecific, dual specific, or multi-specific formats; specifically binding to two or more different antigens. Examples of binding fragments encompassed within the term "antigen binding portion" include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb, which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). Such single chain antibodies are also intended to be encompassed within the term "antigen binding portion". In certain embodiments of the invention, scFv molecules are incorporated into a fusion protein. Other forms of single chain antibodies, such as diabodies are also encompassed. The antigen binding domain can be derived from the same species or a different species for or in which the CAR will be used. In one embodiment, the antigen binding domain is a scFv.

The term "transmembrane domain" refers to the region of the CAR, which crosses or bridges the plasma membrane. The transmembrane domain of the CAR of the invention is the transmembrane region of a transmembrane protein, an artificial hydrophobic sequence or a combination thereof. According to some embodiments, the term comprises also transmembrane domain together with extracellular spacer or hinge region.

The term "intracellular domain" refers to the intracellular part of the CAR and may be an intracellular domain of T cell receptor or of any other receptor (e.g., TNFR superfamily member) or portion thereof, such as an intracellular activation domain (e.g., an immunoreceptor tyrosine-based activation motif (ITAM)-containing T cell activating motif), an intracellular costimulatory domain, or both.

The CAR of the present invention comprises a transmembrane domain (TM domain), one or more costimulatory domains and an activation domain.

In one embodiment of the invention, the CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154 or an analog thereof. According to one embodiment, the TM domain is a TM domain of a receptor selected from CD28 and CD8, or an analog thereof having at least 85% amino acid identity to the original sequence.

In some embodiments of the invention, the CAR comprises a costimulatory domain, e.g., a costimulatory domain comprising a functional signaling domain of a protein selected from the group consisting of OX40, CD2, CD27, CD28, CD5, ICAM-1, LFA-1 (CD11a/CD18), ICOS (CD278), 4-1BB (CD137), an analog thereof and a combination thereof. According to one embodiment, the costimulatory domain is selected from a costimulatory domain of a protein selected from CD28, 4-1BB, OX40, a functional analog thereof having at least 85% amino acid identity to the original sequence, and any combination thereof. According to some embodiments, the CAR of the present invention comprises two or more costimulatory domains. According to one embodiment, the CAR comprises costimulatory domains of CD28 and 4-1BB.

According to one embodiment, the TM domain and the costimulatory domain of the CAR are both derived from CD28.

According to some embodiments, the antigen binding domain is linked to the TM domain via a spacer.

According to any one of the above embodiments, the CAR comprises an activation domain. According to some embodiments, the activation domain is selected from FcRγ (gamma) and CD3-ζ (CD3-zetta) activation domains, or any other sequence that contains an intracellular tyrosine activating motif (ITAM). Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d. According to one embodiment, the activation domain is FcRγ domain.

According to some embodiments, the CAR of the present invention comprises a scFv according to any one of the above embodiments, a TM domain of a receptor selected from CD28 and CD8, a costimulatory domain selected from the domain of CD28, 4-1BB, OX40 and a combination thereof, and an activation domain is selected from FcRγ and CD3-ζ activation domains. According to some embodiments, the CAR of the present invention comprises a scFv having an amino acid sequence SEQ ID NO: 22, a TM domain of a receptor selected from CD28 and CD8, a costimulatory domain selected from the domain of CD28, 4-1BB, OX40 and a combination thereof, and an activation domain is selected from FcRγ and CD3-ζ activation domains. According to some embodiments, the CAR of the present invention comprises a scFv having an amino acid sequence SEQ ID NO: 23, a TM domain of a receptor selected from CD28 and CD8, a costimulatory domain selected from the domain of CD28, 4-1BB, OX40 and a combination thereof, and an activation domain is selected from FcRγ and CD3-ζ activation domains.

The term "CD28" refers to cluster of differentiation 28 protein. In some embodiments, the CD28 is a human CD28.

The term "CD8" refers to cluster of differentiation 8 protein being a transmembrane glycoprotein and serving as a co-receptor for the T cell receptor. According to one embodiment, the CD8 is a human CD8.

The terms "ICOS" and "Inducible T-cell COStimulator" refer to CD278 which is a CD28-superfamily costimulatory molecule. According to one embodiment, the ICOS is a human ICOS.

The term "4-1BB" refers to a CD137 protein which is a member of the tumor necrosis factor receptor family and has costimulatory activity for activated T cells. According to one embodiment, 4-1BB is a human 4-1BB.

The terms "CD3ζ" and "CD3-zetta" refer to a ζ (zetta) chain of CD3 (cluster of differentiation 3) T cell co-receptor participating in activation of both the cytotoxic and helper T cells. According to one embodiment, CD3ζ comprises an immunoreceptor tyrosine-based activation motif (ITAM). According to one embodiment, the CD3ζ is human CD3ζ. CD3ζ is sometimes also referred as CD247.

The term "FcRγ" refers to Fc gamma receptors, which generate signals within their cells through ITAM. These are immunoglobulin superfamily receptors that are found on various innate as well as adoptive immune cells, where the extracellular part binds IgGs the activation signal is transduced through two ITAMs located on its cytoplasmic tail.

According to any one of the above embodiments, the CAR further comprises a leading peptide. According to one embodiment, the leading peptide is located N-terminally to the ABD.

The terms "leader peptide", "leading peptide", "lead peptide", "signaling peptide" and "signal peptide" are used herein interchangeable and refer to a peptide that translocates or prompts translocation of the target protein to cellular membrane.

According to any one of the above embodiments, the CAR of the present invention further comprises a tag sequence. According to some embodiments, the tag is selected haemagglutinin tag, myc tag, poly-histidine tag, protein A, glutathione S transferase, Glu-Glu affinity tag, substance P, FLAG peptide, streptavidin (strep) binding peptide and human FC tag. According to some embodiments, the tags is a strep-tag.

According to another aspect, the present invention provides a nucleic acid molecule encoding at least one chain of the humanized monoclonal antibody or fragment thereof as described in any one of the above embodiments and aspects or the CAR of the present invention. All embodiments and definitions used in any one of the above aspects apply herein as well. According to some embodiments, the nucleic acid molecule encodes at least one chain of the humanized monoclonal antibody or fragment thereof. According to some embodiments the nucleic acid molecule encodes the CAR of the present invention. According to some embodiments, the nucleic acid encodes an amino acid sequence selected from SEQ ID NO: 12, 13, 14, 15, 22, 23, a combination of SEQ ID NO: 12 and SEQ ID NO: 13 or 15, and a combination of SEQ ID NO: 14 and SEQ ID NO: 13 or 15. According to some embodiments, the present invention provides a nucleic acid comprising nucleic acid sequence selected from SEQ ID NO: 16, 17, 18, 19, a combination of SEQ ID NO: 16 and SEQ ID NO 17 or 19, and a combination of SEQ ID NO: 18 and SEQ ID NO: 17 or 19, and a conservative variant thereof.

The term "nucleic acid molecule" refers to a single stranded or double stranded sequence (polymer) of deoxyribonucleotides or ribonucleotides. The terms "nucleic acid" and "polynucleotide" are used herein interchangeably. According to some embodiments, the nucleic acid molecule is an isolated nucleic acid molecule. The term "isolated nucleic acid" as used herein denotes that the nucleic acid is essentially free of other cellular components with which it is associated in the cell. It can be, for example, a homogeneous state and may be dry or in the state of a solution, such as aqueous solution. Purity and homogeneity are typically determined using analytical chemistry techniques such as polyacrylamide gel electrophoresis or high performance liquid chromatography. The term "encoding" refers to the ability of a nucleotide sequence to code for one or more amino acids. The term does not require a start or stop codon. An amino acid sequence can be encoded in any one of six different reading frames provided by a polynucleotide sequence and its complement.

The terms "homolog" "variant", "DNA variant", "sequence variant" and "polynucleotide variant" are used herein interchangeably and refer to a DNA polynucleotide having at least 70% sequence identity to the parent polynucleotide. The variant may include mutations such as deletion, addition or substitution such that the mutations do not change the open reading frame and the polynucleotide encodes a peptide or a protein having substantially similar structure and function as a peptide or a protein encoded by the parent polynucleotide. According to some embodiments, the variants are conservative variants. The term "conservative variants" as used herein refers to variants in which a change of one or more nucleotides in a given codon position results in no alteration in the amino acid encoded at that position. Thus, the peptide or the protein encoded by the conservative variants has 100% sequence identity to the peptide or the protein encoded by the parent polynucleotide. According to some embodiments, the variant is a non-conservative variant encoding to a peptide or a protein being a conservative analog of the peptide of the protein encoded by the parent polynucleotide. According to some embodiments, the variant has at least 75%, at least 80% at least 85%, at least 90%, at least 95%, at least 98% or at least 99% sequence identity to the original nucleic acid sequence. According to one embodiment, the variant is a conservative variant.

According to another aspect, the present invention provides a nucleic acid construct comprising the nucleic acid of the present invention, operably linked to a promoter.

The terms "operably linked", "operatively linked", "operably encodes", "operably bound" and "operably associated" are used herein interchangeably and refer to the functional linkage between a promoter and nucleic acid sequence, wherein the promoter initiates transcription of RNA corresponding to the DNA sequence. A heterologous DNA sequence is "operatively associated" with the promoter in a cell when RNA polymerase which binds the promoter sequence transcribes the coding sequence into mRNA which then, in turn, is translated into the protein encoded by the coding sequence.

The term "promoter" as used herein refers to a regulatory sequence that initiates transcription of a downstream nucleic acid. The term "promoter" refers to a DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible. A constitutive promoter is a promoter that is active under most environmental and developmental conditions. An inducible promoter is a promoter that is active under environmental or developmental regulation, e.g., upregulation in response to xylose availability. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

According to another aspect, the present invention provides a vector comprising the nucleic acid molecule or nucleic acid construct of the present invention. The terms “vector” and “expression vector” are used herein interchangeably and refer to any viral or non-viral vector such as plasmid, virus, retrovirus, bacteriophage, cosmid, artificial chromosome (bacterial or yeast), phage, binary vector in double or single stranded linear or circular form, or nucleic acid, the sequence which is able to transform host cells and optionally capable of replicating in a host cell. The vector may be integrated into the cellular genome or may exist extra-chromosomally (e.g., autonomous replicating plasmid with an origin of replication). The vector may contain an optional marker suitable for use in the identification of transformed cells, e.g., tetracycline resistance or ampicillin resistance. A cloning vector may or may not possess the features necessary for it to operate as an expression vector. Any vector known in the art is envisioned for use in the practice of this invention. According to other embodiments, the vector is a virus, e.g. a modified or engineered virus. The modification of a vector may include mutations, such as deletion or insertion mutation, gene deletion or gene inclusion. In particular, a mutation may be done in one or more regions of the viral genome. Such mutations may be introduced in a region related to internal structural proteins, replication, or reverse transcription function. Other examples of vector modification are deletion of certain genes constituting the native infectious vector such as genes related to the virus’ pathogenicity and/or to its ability to replicate. Any virus can be attenuated by the methods disclosed herein. According to some embodiments, the vector is a virus selected from lentivirus, adenovirus, modified adenovirus and retrovirus. In one particular embodiment, the vector is lentivirus. According to other embodiments, the vector is a plasmid.

According to another aspect, the present invention provides a cell comprising the humanized monoclonal antibody or the antibody fragment thereof, the CAR, the nucleic acid molecule, the nucleic acid construct or the vector of the present invention. According to some embodiments, the cell comprises the humanized monoclonal antibody. According to one embodiment, the cell comprises a fragment of the humanized monoclonal antibody of the present invention. According to other embodiments, the cell comprises or expresses the CAR or the present invention. According to yet another embodiment, the cell comprises the nucleic acid molecule, the nucleic acid construct or the vector of the present invention encoding the humanized monoclonal antibody or the antibody fragment thereof or the CAR of the present invention.

According to some embodiments, the cell is selected from bacterial, fungi such as yeast and mammalian cell. According to some embodiments, the cell is a mammalian cell. According to another embodiment, the cell is a human cell. According to some embodiments, the cell is a leukocyte. According to some embodiments, the cell is selected from T cell and a natural killer (NK) dell. According to some embodiments, the present invention provides a T-cell genetically modified to express the CAR of the present invention.

According to some embodiment, the cells are T cells. Thus, according to some embodiments, the present invention provides T-cells comprising the CAR of the present invention. According to some embodiments, the T-cells comprise a CAR comprising the humanized mAb or the fragment thereof as described in any one of the above aspects and embodiments. All embodiments and definitions used in any one of the above aspects apply and encompassed herein as well. According to some embodiments, the cell comprises the CAR comprising an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively. According to another embodiment, the CAR comprises an antigen binding domain comprising a heavy-chain variable domain (VH) and a light-chain variable domain (VL), wherein the VH comprises amino acid sequence selected from SEQ ID NO: 1 or 34 in which 10 or amino acid residues in the framework regions are substituted and the VL comprises amino acid sequence SEQ ID NO: 2 in which 10 or more amino acid residues in the framework regions are substituted According to some embodiments, the CAR comprises a scFv of the present invention. According to some embodiments, the CAR comprises a scFv comprising an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2 and 3 have amino acid sequences SEQ ID NO: 24, 25 and 26, respectively, the VH-FR4 has amino acid sequence selected from SEQ ID NO: 27 and 32, the VL-FR1 has amino acid sequence selected from SEQ ID NO: 28 and 33, and the VL-FR 2, 3 and 4 have amino acid sequences SEQ ID NO: 29, 30, and 31, respectively. According to some embodiments, the present invention provides an scFv wherein the VH comprises amino acid sequence selected from SEQ ID NO: 12 and 14, and the VL comprises amino acid sequence selected from SEQ ID NO: 13 and 15. According to one embodiment, the VH of the scFv comprises amino acid sequence SEQ ID NO: 12 and the VL comprises amino acid sequence SEQ ID NO: 13. According to yet another embodiment the VH of the scFv comprises amino acid sequence SEQ ID NO: 14 and the VL comprises amino acid sequence SEQ ID NO: 15. According to one embodiment, the CAR comprises a scFv comprising the amino acid sequence selected from SEQ ID NO: 22. According to, another embodiment, the CAR comprises a scFv comprising the amino acid sequence selected from SEQ ID NO: 23.

According to any one of the above embodiments, the present invention provide T-cells comprising a nucleic acid encoding the antibody or a fragment of the antibody of the present invention.

The term "T cell" refers to a type of white blood cell that can be distinguished from other white blood cells by the presence of a T cell receptor on the cell surface. There are several subsets of T cells, including, but not limited to, T helper cells (a.k.a. Tx cells or $CD4^+$ T cells) and subtypes, including $T_H1$, $T_H2$, $T_H3$, $T_H17$, $T_H9$, and $T_{FH}$ cells, cytotoxic T cells (i.e., Tc cells, $CD8^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including $CD4^+$ $FOXP3^+$ $T_{reg}$ cells, $CD4^+FOXP3^-$ $T_{reg}$ cells, Tr1 cells, Th3 cells, and $T_{reg}17$ cells, natural killer T cells (a.k.a. NK cells or NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention. According to some embodiments, the cells are T cells. According to some embodiments, the T-cells are selected from memory, regulatory, helper or natural killer T-cells. According to some embodiments, the T cell is selected are from $CD4^+$ T-cell and a $CD8^+$ T-cell. According to some embodiments, the T cell are $CD4^+$ T-cell and a $CD8^+$ T-cell. According to some embodiments, the cells are NK cells. According to some embodiments, the cells are NK T-cells.

According to some embodiments, the cells are capable of producing or expressing or produces or expresses the humanized monoclonal antibody or the antibody fragment of the present invention or the of the present invention. According to one embodiment, the cell is a Hybridoma cell.

According to some embodiments, the present invention provides T cells capable of expressing the CAR of the present invention. Such cells comprise nucleic acid(s) encoding said CAR.

According to any one of the above embodiments, the humanized mAb of the present invention or the functional fragment thereof is capable of activating T cells. According to one embodiment, the mAb of the present invention of the functional fragment thereof is capable of promoting T cells proliferation, generation and/or survival. According to some embodiments, the T-cells are selected from memory, regulatory, helper and natural killer T-cells. As used herein, the term "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. Activation results in clonal expansion of T cells, upregulation of activation markers on the cell surface, differentiation into effector cells, induction of cytotoxicity or cytokine secretion, induction of apoptosis, or a combination thereof. As used herein, "improving cell survival" and "promoting cell survival" refers to an increase in the number of cells that survive a given condition or period, as compared to a control, e.g., the number of cells that would survive the same conditions in the absence of treatment. Conditions can be in vitro, in vivo, ex vivo, or in situ. Improved cell survival can be expressed as a comparative value, e.g., twice as many cells survive if cell survival is improved two-fold. Improved cell survival can result from a reduction in apoptosis, an increase in the life-span of the cell, or an improvement of cellular function and condition.

According to another aspect, the present invention provides a composition comprising a plurality of humanized monoclonal antibody or antibody fragments or cells of the present invention, and a carrier. According to some embodiments, the present invention provides a composition comprising a plurality of cells expressing or capable of expressing the CAR of the present invention. According to some embodiments, the cells are T cells according to some embodiments, the CAR comprises scFv comprising SEQ ID NO: 12, 13, 14, 15, 22 or 23. The term "carrier" includes as a class any compound, solvent or composition useful in facilitating storage, stability, and use of the mAbs or fragments of the present invention.

According to some embodiments, the composition is a pharmaceutical composition and the carrier is a pharmaceutically acceptable carrier. Thus, according to some embodiments, the present invention provides a pharmaceutical composition comprising the humanized monoclonal antibody of the present invention, and a pharmaceutically acceptable carrier. According to one embodiment, the pharmaceutical composition of the present invention comprises a plurality of the antibody fragments of the present invention, and a pharmaceutically acceptable carrier. According to some embodiment, the pharmaceutical composition of the present invention comprises a plurality of the conjugates comprising the humanized monoclonal antibody or fragments thereof of the present invention, and a pharmaceutically acceptable carrier. According to another embodiment, the pharmaceutical composition of the present invention comprises a plurality of cells of the present invention, and a pharmaceutically acceptable carrier. According to another embodiment, the pharmaceutical composition of the present invention comprises a plurality of T-cells comprising the CAR of the present invention, and a pharmaceutically acceptable carrier. According to another embodiment, the pharmaceutical composition of the present invention comprises a plurality of T-cells comprising a nucleic acid encoding the CAR of the present invention, and a pharmaceutically acceptable carrier. All embodiments and definitions used in any one of the above aspects and embodiments apply herein as well.

The term "pharmaceutical composition" as used herein refers to a composition comprising at least one active agent as disclosed herein, e.g. CAR T-cells, formulated together with one or more pharmaceutically acceptable carriers.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules.

The pharmaceutical compositions of the present invention may be prepared by conventional techniques, e.g., as described in Remington: The Science and Practice of Pharmacy, 19th Ed., 1995. The compositions may be in solid, semisolid or liquid form and may further include pharmaceutically acceptable fillers, carriers or diluents, and other inert ingredients and excipients. The compositions can be administered by any suitable route, e.g., orally, intravenously, parenterally, rectally or transdermally, the oral route being preferred. The dosage will depend on the state of the patient, and will be determined as deemed appropriate by the practitioner.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions. solid carriers or excipients such as, for example, lactose, starch or talcum or liquid carriers such as, for example, water, fatty oils or liquid paraffins.

Solutions or suspensions used for parenteral, intradermal, or subcutaneous application typically include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose glass or plastic vials.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets. Such compositions preferably comprise a therapeutically effective amount of a compound of the invention and/or other therapeutic agent(s), together with a suitable amount of carrier so as to provide the form for proper administration to the subject.

According to one embodiment, the pharmaceutical composition comprises the humanized mAb or the fragment of the present invention that binds specifically to SLeA comprising VH domain comprising amino acid sequence selected from SEQ ID NO: 12 and 14, and the VL comprises amino acid sequence selected from SEQ ID NO: 13 and 15. According to some embodiments, the pharmaceutical composition comprises a plurality of T-cells expressing, configured to express or capable of expressing the CAR of the present invention comprising VH domain comprising amino acid sequence selected from SEQ ID NO: 12 and 14, and the VL comprises amino acid sequence selected from SEQ ID NO: 13 and 15. According to other embodiments, the pharmaceutical composition comprises a plurality of T-cell expressing, configured to express or capable of expressing the CAR of the present invention comprising amino acid sequence selected from SEQ ID NO: 22 and 23. According to other embodiments, the pharmaceutical composition comprises a plurality of T-cell expressing, configured to express or capable of expressing the CAR of the present invention comprising scFv consisting of amino acid sequence selected from SEQ ID NO: 22 and 23. According to one embodiment, the pharmaceutical composition comprises cells such as T-cells comprising the nucleic acid or nucleic acid construct of to the present invention.

According to some embodiments, the pharmaceutical composition is formulated for a parenteral administration. According to one embodiment, the composition is formulated for subcutaneous, intraperitoneal (IP), IM, IV or intratumor administration. According to other embodiments, the pharmaceutical composition is formulated as a solution such as a sterile solution for injection.

According to any one of the above embodiments, the pharmaceutical composition of the present invention is for use in treating cancer. According to some embodiments, the pharmaceutical composition comprising the humanized mAb, fragments thereof or conjugates thereof is for use in treating cancer. According to some embodiments, the pharmaceutical composition comprising T-cells comprising the CAR of the present invention is for use in treating cancer. According to some embodiments, the cancer is a cancer overexpressing SLeA glycan. According to one embodiment, the cancer is selected from hematological, breast, ovarian, pancreatic, colorectal, stomach, head and neck, liver, lung, oropharyngeal cancer, squamous cell carcinoma and gallbladder cancer. According to one embodiment, the cancer is a breast cancer. According to some embodiment, the cancer is a Her-2 negative breast carcinoma. According to another embodiment, the cancer is an ovarian cancer. According to a further embodiment, the cancer is a colon cancer. According to one embodiment, the cancer is colon adenocarcinoma. According to one embodiment, the cancer is a colorectal cancer. According to another embodiment, the cancer is a stomach cancer. According to one embodiment, the cancer is a pancreatic cancer. According to one embodiment, the cancer is carcinoma. According to one embodiment, the cancer is a hematological cancer overexpressing SLeA glycan. According to another embodiment, the cancer is a pancreatic adenocarcinoma. According to yet another embodiment, the cancer is lung cancer. According to one embodiment, the cancer is lung adenocarcinoma. According to some embodiments, the cancer is squamous cell carcinoma. According to another embodiment, the cancer is pharynx squamous cell carcinoma.

The term "treating" a condition or patient refers to taking steps to obtain beneficial or desired results, including clinical results. Beneficial or desired clinical results include, but are not limited to, or ameliorating abrogating, substantially inhibiting, slowing or reversing the progression of a disease, condition or disorder, substantially ameliorating or alleviating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s).

The term "treating cancer" as used herein should be understood to e.g. encompass treatment resulting in a decrease in tumor size; a decrease in rate of tumor growth; stasis of tumor size; a decrease in the number of metastases; a decrease in the number of additional metastasis; a decrease in invasiveness of the cancer; a decrease in the rate of progression of the tumor from one stage to the next; inhibition of tumor growth in a tissue of a mammal having a malignant cancer; control of establishment of metastases; inhibition of tumor metastases formation; regression of established tumors as well as decrease in the angiogenesis induced by the cancer, inhibition of growth and proliferation of cancer cells and so forth. The term "treating cancer" as used herein should also be understood to encompass prophylaxis such as prevention as cancer reoccurs after previous treatment (including surgical removal) and prevention of cancer in an individual prone (genetically, due to life style, chronic inflammation and so forth) to develop cancer. As used herein, "prevention of cancer" is thus to be understood to include prevention of metastases, for example after surgical procedures or after chemotherapy.

The use comprises administering the pharmaceutical composition of the present invention to the subject. According to any one of the above embodiments, the composition of the present invention is administered as known in the art. According to one embodiment, the composition is parenterally administered, e.g. IP, IV, IM, SC or intratumorally. According to some embodiments, the pharmaceutical composition of the present invention is administered via infusion, such as IV infusion. According to some embodiments, the composition is systemically administered. According to other embodiments, the composition is locally administered.

The terms "administering" or "administration of" a substance, a compound, the composition or an agent to a subject are used herein interchangeably and refer to an administration mode that can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. According to some embodiments, the composition is administered 1, 2, 3, 4, 5 or 6 times a day. According to other embodiments, the composition is administered 1, 2, 3, 4, 5 or 6 times a month. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. According to one embodiment, the pharmaceutical composition is parenterally administered. The term "parenteral" refers to subcutaneous, intracutaneous, intravenous, intramuscular, intraarticular, intraarterial, intrasynovial, intrasternal, intrathecal, intralesional, intraperitoneal and intracranial injection, as well as various infusion techniques.

According to some embodiments, the pharmaceutical composition of the present invention is co-administered with other anti-tumor therapy including but not limited to anti-cancer drugs, radiotherapy, immunotherapy and surgery. According to some embodiments, the therapeutic agents suitable for co-administration with the pharmaceutical composition of the present invention are selected from chemotherapeutic agents, radioactive isotopes, toxins, cytokines such as interferons, immunostimulating agents, immunomodulating agents and antagonistic agents targeting cytokines, cytokine receptors or antigens associated with tumor cells. In some embodiments, an anti-cancer agent is a chemotherapeutic.

According to another aspect, the present invention provides a method for treating cancer in a subject in need thereof comprising administering a therapeutically effective amount of the humanized mAb antibodies or functional fragments thereof of the present invention. According to another embodiment, the method comprises administering a pharmaceutical composition comprising the humanized mAb or fragments thereof to the subject. According to another embodiment, the method comprises administering conjugates of the humanized mAb or fragments thereof to the subject. According to another embodiment, the method comprises administering CAR of the present invention to the subject. According to one embodiment, the method comprises administering T-cells comprising the CAR of the present invention to the subject. According to yet another embodiment, the method comprises administering a pharmaceutical composition comprising cells or expressing the humanized mAb or the fragments thereof to the subject. According to some embodiments, the humanized mAb antibodies or functional fragments thereof are formulated with a delivery system such as liposomes.

According to yet another aspect, the present invention provides a use of the humanized mAb antibodies or functional fragments thereof of the CAR of the present invention for preparing a medicament for treating cancer.

The present invention further provides a method of detecting, determining, and/or quantifying the expression SLeA on cells. According to some embodiments, detecting, determining, and/or quantifying the expression of SLeA may be used in diagnosing conditions associated with expression of SLeA, such as cancer. Thus, the humanized mAb, the fragment of the present invention or the conjugates of the present invention are for use in cancer diagnosis, monitoring the progression of cancer, or monitoring and estimating the effectiveness of treatment of cancer. The term "monitoring cancer" encompasses the term monitoring the progression of cancer and monitoring the effectiveness of treatment of cancer. In some embodiments, the present invention provides a method of diagnosing, assessing the severity or staging of a proliferative disease such as cancer in a subject, the method comprises detecting the presence or expression of SLeA in a biological sample of the subject using at least one antibody or antibody fragment of the present invention or the composition comprising same. According to some embodiments, the antibody or fragment thereof is conjugated or labeled. According to some embodiments, the method comprises quantitatively comparing the level of expression of the SLeA glycan in a subject to a reference expression level of e.g. of healthy subjects. According to some embodiments, change in expression of SLeA in comparison to expression in healthy subjects indicates the presence of cancer. According to some embodiments, overexpression of the SLeA correlates with cancer. Thus, in some embodiments, detecting SLeA expression level above the reference value obtained from healthy subjects correlates with the presence of cancer. The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived therefrom and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilisation, or enrichment for certain components.

According to any one of the above embodiments, the method comprises detecting SLeA in the sample, e.g. biological sample. The method comprises contacting the biological sample with the antibody or the fragment of the present invention. According to some embodiments, the antibody or the fragment are marked, tagged or labeled. According to other embodiments, secondary antibodies may be used to determine the level of binging of the antibody of the present invention or the fragment to the biological sample of its components. According to some embodiments, any known methods for determining and quantifying binding of an antibody or a fragment thereof to its target may be used. According to some embodiments, detecting comprises quantifying the amount of the SLeA. According to some embodiment, the method comprises a comparison of the content of the SLeA in a biological sample obtained from a subject to the control, i.e. comparing to the content of SLeA in the comparable biological sample of healthy subjects. According to some embodiments, the monitoring method comprises comparing SLeA content in a sample obtained from a subject at different times and assessing the propagation (i.e. monitoring) of the disease and/or effectiveness of treatment. According to some embodiments, the present invention provides a method of detection of SLeA in a tissue culture, in a tissue or in a section obtained from a subject.

The methods of determining or quantifying the expression of the SLeA according to any one of the above embodiments comprises contacting a biological sample with an antibody or antibody fragment, and measuring the level of complex formation. Determining and quantifying methods may be performed in-vitro or ex-vivo. The antibodies according to the present invention may be also used to configure screening methods. For example, an enzyme-linked immunosorbent assay (ELISA), or a radioimmunoassay (RIA), as well as methods such as IHC or FACS, can be constructed for measuring levels of secreted or cell-associated SLeA glycan using the antibodies of the present invention and methods known in the art. According to some embodiments, the method for detecting or quantifying the presence of SLeA expressed on cells comprises the steps of:

incubating a biological sample with the humanized antibodies or antibody fragments of the present invention comprising at least an antigen-binding portion; and detecting the bound SLeA using a detectable probe.

According to some embodiments, the method further comprises the steps of:

comparing the amount of (ii) to a standard curve obtained from a reference sample containing a known amount of SLeA; and calculating the amount of the SLeA in the sample from the standard curve.

According to some particular embodiments, the sample is a body fluid.

According to some embodiments, the method is performed in-vitro or ex-vivo.

According to any one of the above embodiments, the method further comprises consulting or providing recommendations regarding the treatment of the disease or condition or providing the treatment of the disease, such as cancer.

According to another aspect, the present invention provides a kit for detecting cancer, wherein the kit comprises antibodies or antibody fragments of the present invention and means for detecting the amount of the antibodies or antibody fragments bound to cells of the biological sample. According to some embodiments, the kit is a diagnostic kit.

Sequence Table

| | SEQ ID | Sequence |
|---|---|---|
| mNative VH | 1 | EVKLEESGGG LVQPGGSMKL SCAASGFTES DAWMDWVRQS PEKGLEWVAE IGNKGNNHAT YYAESVKGRF TVSRDDSKSR VYLQMNSLRV EDTGTYYCTT RFAYWGQGTL VTVSA |
| mNative VL | 2 | DIKMTQSPSS MYASLGERVT ITCKASQDIN SYLSWFQQKP GKSPKTLIYR ANRLVDGVPS RFSGSGSGQD YSLTISSLEY EDMGIYYCLQ YDEFPRTEGG GTKLEIK |
| HuNative VH | 12 | EVQLVESGGGLVQPGGSLRLS CAASGFTFSDAWMDWVRQAPG KGLEWVAEIGNKGNNHATYYA ESVKGRFTISRDDSKNSLYLQ MNSLKTEDTAVYYCTTRFAYW GQGTLVTVSS |
| HuNative VL | 13 | DIQMTQSPSSLSASVGDRVTI TCKASQDINSYLSWFQQKPGK APKLLIYRANRLVDGVPSRFS GSGSGTDFTFTISSLQPEDIA TYYCLQYDEFPRTFGGGTKVE IK |
| HuRA9-23 VH | 14 | EVQLVESGGGLVQPGGSLRLS CAASGFTESDAWMDWVRQAPG KGLEWVAEIGNKGNNHATNYA ESVKGRFTISRDDSKNSLYLQ MNSLKTEDTAVYYCTTRFAYW GQGTPVTVPS |
| HuRA9-23 VL | 15 | DIQMTQSPSSLSASVGDRVTI PCKASQDINSYLSWFQQKPGK APKLLIYRANRLVDGVPSRFS GSGSGTDFTFTISSLQPEDIA TYYCLQYDEFPRTFGGGTKVE IK |
| scFv HuNative | 22 | EVQLVESGGGLVQPGGSLRLS CAASGFTFSDAWMDWVRQAPG KGLEWVAEIGNKGNNHATYYA ESVKGRFTISRDDSKNSLYLQ MNSLKTEDTAVYYCTTRFAYW GQGTLVTVSSGGGGSGGGGSG GGGSDIQMTQSPSSLSASVGD RVTITCKASQDINSYLSWFQQ |

-continued

Sequence Table

| | SEQ ID | Sequence |
|---|---|---|
| | | KPGKAPKLLIYRANRLVDGVP<br>SRFSGSGSGTDFTFTISSLQP<br>EDIATYYCLQYDEFPRTFGGG<br>TKVEIK |
| scFv HuRA9-23 | 23 | EVQLVESGGGLVQPGGSLRLS<br>CAASGFTFSDAWMDWVRQAPG<br>KGLEWVAEIGNKGNNHATNYA<br>ESVKGRFTISRDDSKNSLYLQ<br>MNSLKTEDTAVYYCTTRFAYW<br>GQGTPVTVPSGGGGSGGGGSG<br>GGGSDIQMTQSPSSLSASVGD<br>RVTIPCKASQDINSYLSWFQQ<br>KPGKAPKLLIYRANRLVDGVP<br>SRFSGSGSGTDFTFTISSLOP<br>EDIATYYCLQYDEFPRTFGGG<br>TKVEIK |

The term "consisting essentially of" means that the composition or component may include additional ingredients, but only if the additional ingredients do not materially alter the basic and novel characteristics of the claimed compositions or methods.

As used herein, the term "about", when referring to a measurable value such as an amount, a temporal duration, and the like, is meant to encompass variations of +/−10%, or +1-5%, +/−1%, or even +/−0.1% from the specified value.

Having now generally described the invention, the same will be more readily understood through reference to the following examples, which are provided by way of illustration and are not intended to be limiting of the present invention.

EXAMPLES

Methods

Random Mutagenesis and Library Generation

Native sequences of 1116NS19.9 VH and VL were obtained from IMGT database, accession number S65761 and S65921 respectively.

Native scFv with $(G_4S)_3$ linker (DNA seq: ggaggtggcggtagcggaggcggcggttctggaggtggcgggagc (SEQ ID NO: 21); Amino acids seq: GGGGSGGGGSGGGGS (SEQ ID NO: 20) was synthesized by Integrated DNA Technologies Inc.

Humanization of mNative and mRA9-23

The DNA sequences of the variable heavy (VH) and the variable light (VL) regions of the mouse-derived Native 1116NS19.9 antibody (mNative) and the clone mRA9-23 antibody were compared to human germline sequences in the human immunoglobulin database by the IgBlast tool, resulting in the best fit for VH to IGHV3-72*01 (>65.6% identity), and for VL to IGKV1-33*01 (>65.2% identity), that served as the basis for antibodies humanization. This germline sequences database does not cover the framework 4 (FR4) regions, therefore we screened the IGHJ sequences in IMGT database for common human VH FR4 with sequence similarity to the VH FR4 of mNative and mRA9-23 antibodies. Out of the three different alleles of the highest sequence similarity, IGHJ4*01 sequence was selected as the basis for VH FR4 humanization. For VL FR4 similarity analysis of mNative and mRA9-23 antibodies, IMGT database revealed two different alleles with the highest sequence similarity, IGKJ4*01 sequence was selected as the basis for VL FR4 humanization. For full antibody humanization, the FR sequences were then mutated based on the selected germline sequences, while the CDRs were mostly preserved based on the corresponding mNative and mRA9-23 antibodies to yield the humanized mNative (HuNative) and humanized RA9-23 (HuRA9-23) antibodies.

Expression of HuNative and HuRA9-23 Single-Chain Fv (scFv) Fragments on Yeast Cells To obtain yeast cells with surface expression of the humanized antibody clones, the single-chain Fv (scFv) fragments of HuNative and HuRA9-23 (comprising the HV and VL domains combined by a linker) were cloned into the YSD pETCON2-based system. Corresponding scFv fragments with flanking regions homologous to pETCON2 VH/VL plasmids were synthesized (Integrated DNA Technologies Inc.; IDT, Israel), then PCR amplified by mixing 2 µl (20 ng) scFv template, 1 µl (10 µM) of each primer, 25 µl of DreamTaq Green PCR Master Mix (2×) (Thermo Scientific) and 21 µl PCR grade water. PCR settings were 95° C. for 2 min, followed by 30 cycles of 95° C. for 30 s, 55° C. for 30 s, 72° C. for 60 s and final incubation of 72° C. for 5 min. Each amplified fragment was purified by Wizard SV Gel and PCR clean-up system. EBY100 yeast cells were transformed with scFv by LiAc/SS Carrier DNA/peg method, as described (Gietz and Schiestl, 2007), using 300 ng of NdeI and BamHI (Thermo Scientific) digested pETCON2 plasmid and 576-648 ng of gel-purified scFv. Following recovery, the yeast cells were plated on a synthetic defined media (SD) lacking Tryptophan (Trp) [SD-Trp plates; 2% glucose (Sigma), 0.67% yeast nitrogen base w/o amino acids (BD), 0.54% $Na_2HPO_4$ (Sigma), 0.86% $NaH_2PO_4$ (Sigma) and 0.192% yeast synthetic drop-out medium supplements without Trp (Sigma)], then incubated at 30° C. Two days later, single colonies were picked and cultured in SD-Trp liquid media, and plasmids were purified from yeast cells using Zymoprep Yeast Plasmid Miniprep II (Zymo Research) according to manufacturer's instructions. To validate the sequences, plasmids were electroporated into XL1 *Escherichia coli*, plasmids were purified by NucleoSpin Plasmid EasyPure (Macherey-Nagel) and sequences analyzed at Tel Aviv University core facility.

Apparent $K_D$ Calculations of Yeast Cells Expressing Surface-scFv scFv-HuNative and scFv-HuRA9-23 yeast variants were cultured in SD-Trp at 30° C., passaged 1:10 each day for three days, then scFv were triggered to be expressed by transfer to a synthetic galactose (SG) based media [SG-Trp media: 2% galactose (Sigma), 0.2% glucose, 0.67% yeast nitrogen base w/o amino acids, 0.54% $Na_2HPO_4$, 0.86% $NaH_2PO_4$, and 0.192% yeast synthetic drop-out medium supplements without Trp], then grown at 20° C. To calculate apparent $K_D$, $5\times10^6$ yeast cells were washed with 1 ml assay buffer (PBS, 0.5% ovalbumin), then incubated in ten serial dilutions of $SLe^a$-PAA-Biotin antigen ranging at 3333-0.16 nM together with 1:50 diluted mouse-anti-c-Myc (4 µg/ml) in assay buffer for 1 h at room temperature (RT) with rotation. Cells were washed with 1 ml ice cold assay buffer, then incubated for 40 min on ice with APC-streptavidin and Alexa-Fluor-488-goat-anti-mouse IgG1 diluted 1:50 (10 µg/ml) and 1:200 (10 µg/ml) respectively in assay buffer. Cells were then washed with 1 ml ice cold PBS and resuspended in 500 µl PBS. Cell fluorescence was measured by CytoFLEX flow cytometry (Beckman Coulter) and analyzed with Kaluza analysis software. scFv expressing cells were gated and the geometric mean of antigen binding was calculated. Geometric mean was plotted vs. antigen concentration and apparent $K_D$ was calculated according to non-linear fit with one-site specific binding using GraphPad Prism 8.0 as described (Amon et al., 2020, *Cancers* (*Basel*), 12(10): 2824).

Specificity Analysis of scFv-HuNative and scFv-HuRA9-23 scFv-HuNative and scFv-HuRA9-23 yeast variants were induced to express scFv as indicated (by transfer to SG-Trp media at 20° C.), then 5×10$^6$ yeast cells were washed with 1 ml assay buffer (PBS, 0.5% ovalbumin), incubated with 0.5 M SLe$^a$-PAA-Biotin or 0.5 μM Le$^a$-PAA-Biotin antigens together with 1:50 diluted mouse-anti-c-Myc (4 μg/ml) diluted in assay buffer for 1 h at RT with rotation. Cells were washed with 1 ml ice cold assay buffer, then incubated for 40 min on ice with APC-streptavidin and Alexa-Fluor-488-goat-anti-mouse IgG1 diluted 1:50 (10 μg/ml) and 1:200 (10 μg/ml) respectively in assay buffer. Cells were washed with 1 ml ice cold PBS, then resuspended in 500 μl PBS. Cell fluorescence was measured by CytoFLEX flow cytometry (Beckman Coulter) and analyzed with Kaluza analysis software.

Immunogenicity Analysis of scFv-HuNative and scFv-HuRA9-23

Immunogenicity of humanized antibody clones was evaluated by analysis of scFv recognition by pooled human IgG obtained from thousands of human donors (IVIg; Gamma Gard). For this purpose, IVIg was first pre-cleared from anti-yeast reactivity by serial incubations with yeast cells, then binding to scFv-expressing yeast cells was examined. Uninduced HuNative yeasts cells grown in SD-Trp at 30° C. were divided into 9 different Eppendorf tubes with 5×10$^6$ cells in each. Cells were washed twice with 1 ml PBS, then supernatant was removed. For anti-yeast adsorption, yeast cells in the first tube were resuspended in 1 ml of 68 mg/ml IVIg, followed by 10 min with rotation of 30 rpm at RT. Yeast-IVIg mixture was centrifuged at 10,000×g for 1 min, and supernatant with unbound antibodies was transferred into a fresh yeast pellet tube for a second cycle of antibody adsorption as described, and this was repeated for a total of nine incubations, thus decreasing the amount of anti-yeast antibodies in the IVIg resulting in a "yeast-purified IVIg" pooled human IgG. Subsequently, scFv-HuNative and scFv-HuRA9-23 yeast variants were induced to express scFv as indicated (by transfer to SG-Trp media at 20° C.), then 5×10$^6$ yeast cells were washed with 1 ml assay buffer (PBS, 0.5% ovalbumin), then incubated with 25, 50 or 100 ng/μl yeast-purified IVIg in assay buffer for 45 min at RT with rotation. Cells were washed with 1 ml ice cold assay buffer, then incubated for 45 min on ice with 1:50 diluted mouse-anti-c-Myc (4 μg/ml) in assay buffer. Cells were washed with 1 ml ice cold assay buffer, then incubated for 40 min with Cy3-anti-human IgG Fc specific and Alexa-Fluor-488-goat-anti-mouse IgG1 diluted 1:100 (15 μg/ml) and 1:200 (10 μg/ml) respectively in assay buffer. Cells were washed with 1 ml ice cold PBS, then resuspended in 500 μl PBS for flow cytometry analysis.

Gibson Assembly of Full Length HuNative and HuRA9-23 Antibodies Expression Plasmids Variable heavy and variable light fragments of HuNative and HuRA9-23 were amplified by PCR. Reaction was made in Q5 reaction buffer, with 1 μl of plasmid DNA template purified from *E. coli*, 200 μM each dNTP, 1 U Q5 hot start high fidelity DNA polymerase (New England Biolabs), 500 nM each primer complete volume to 50 μl with PCR grade water. PCR conditions were 95° C. for 2 min followed by 30 cycles of 95° C. for 30 s, 61° C. for 60 s, 72° C. for 60 s, and final incubation of 72° C. for 5 min. To remove template segments, the PCR product was supplemented with 6 μl of 10× FastDigest Green Buffer, 1 μl FastDigest DpnI (Thermo Scientific), and completed the volume to 60 μl with PCR grade water, then incubated at 37° C. for 1 h. PCR digested fragments were purified from agarose gel by Zymoclean Gel DNA Recovery Kit (Zymo Research). Heavy and light chain full IgG p3BNC expression plasmids were divided into three parts for PCR amplification, variable region, left arm and right arm. Left and right arms of heavy and light p3BNC plasmids were amplified, digested and purified as described for variable regions using primers. Of each fragment (variable region, right arm and left arm), 25 ng were taken for Gibson assembly. Reaction was made in isothermal reaction buffer containing 3.75% PEG 8000, 75 mM Tris-HCl pH 7.5, 7.5 mM MgCl2, 7.5 mM DTT, 0.15 mM of each dNTP and 0.75 mM NAD. To this buffer we added 0.04 U T5 exonuclease (NEB), 0.25 U Phusion polymerase (NEB) and 40 U Taq DNA ligase (NEB), and ligation was made at 50° C. for 1 h. Plasmids were electroporated into XL1 *Escherichia coli*, to validate the sequence and for production p3BNC expression plasmids.

Expression and Purification of Full-Length HuNative and HuRA9-23 IgG Antibodies

Human embryonic kidney 293A cells were used to produce whole antibodies clones from the p3BNC expression plasmids template transfected with polyethylenimine reagent (PEI; Polysciences), as described (Amon et al., 2018). Antibodies were purified using protein A (GE healthcare) and concentrations determined by BCA assay (Pierce).

Sialoglycan Microarray Nanoprinting

Arrays were fabricated with NanoPrint LM-60 Microarray Printer (Arrayit) on epoxide-derivatized slides (Corning 40044) with 16 sub-array blocks on each slide. Glycoconjugates were distributed into one 384-well source plates using 4 replicate wells per sample and 8 μL per well (Versions 13.0 and 13.1). Each glycoconjugate was prepared at 100 μM in an optimized print buffer (300 mM phosphate buffer, pH 8.4). To monitor printing quality, replicate-wells of human IgG (80, 40, 20, 10, 5, 0.25 ng/μL in PBS+10% glycerol) and AlexaFlour-555-Hydraside (Invitrogen A20501MP, at 1 ng/μL in 178 mM phosphate buffer, pH 5.5) were used for each printing run. The arrays were printed with four 946MP3 pins (5 μm tip, 0.25 μL sample channel, ~100 μm spot diameter; Arrayit). Each block (sub-array) has 20 spots/row, 20 columns with spot to spot spacing of 275 μm. The humidity level in the arraying chamber was maintained at about 70% during printing. Printed slides were left on arrayer deck over-night, allowing humidity to drop to ambient levels (40-45%). Next, slides were packed, vacuum-sealed and stored at RT until used. Table 1 shows the list of glycans printed on sialoglycan microarray.

TABLE 1

List of glycans fabricated on glycan microarrays.

| Glycan ID | Structure |
|---|---|
| 1 | Neu5,9Ac$_2$α3Galβ4GlcNAcβO(CH$_2$)$_2$CH$_2$NH$_2$ |
| 2 | Neu5Gc9Acα3Galβ4GlcNAcβO(CH$_2$)$_2$CH$_2$NH$_2$ |
| 3 | Neu5,9Ac$_2$α6Galβ4GlcNAcβO(CH$_2$)$_2$CH$_2$NH$_2$ |
| 4 | Neu5Gc9Acα6Galβ4GlcNAcβO(CH$_2$)$_2$CH$_2$NH$_2$ |

TABLE 1-continued

List of glycans fabricated on glycan microarrays.

| Glycan ID | Structure |
|---|---|
| 5 | Neu5Acα6GalNAcαO$(CH_2)_2CH_2NH_2$ |
| 6 | Neu5Gcα6GalNAcαO$(CH_2)_2CH_2NH_2$ |
| 7 | Neu5,9$Ac_2$α3Galβ3GlcNAcβO$(CH_2)_2CH_2NH_2$ |
| 8 | Neu5Gc9Acα3Galβ3GlcNAcβO$(CH_2)_2CH_2NH_2$ |
| 9 | Neu5,9$Ac_2$α3Gal3β3GalNAcαO$(CH_2)_2CH_2NH_2$ |
| 10 | Neu5Gc9Acα3Galβ3GalNAcαO$(CH_2)_2CH_2NH_2$ |
| 11 | Neu5Acα3Galβ4GlcNAcβO$(CH_2)_2CH_2NH_2$ |
| 12 | Neu5Gcα3Galβ4GlcNAcβO$(CH_2)_2CH_2NH_2$ |
| 13 | Neu5Acα3Galβ3GlcNAcβO$(CH_2)_2CH_2NH_2$ |
| 14 | Neu5Gcα3Galβ3GlcNAcβO$(CH_2)_2CH_2NH_2$ |
| 15 | Neu5Acα3Galβ3GalNAcαO$(CH_2)_2CH_2NH_2$ |
| 16 | Neu5Gcα3Galβ3GalNAcαO$(CH_2)_2CH_2NH_2$ |
| 17 | Neu5Acα6Galβ4GlcNAcβO$(CH_2)_2CH_2NH_2$ |
| 18 | Neu5Gcα6Galβ4GlcNAcβO$(CH_2)_2CH_2NH_2$ |
| 19 | Neu5Acα6Galβ4GlcβO$(CH_2)_2CH_2NH_2$ |
| 20 | Neu5Gcα6Galβ4GlcβO$(CH_2)_2CH_2NH_2$ |
| 21 | Neu5Acα3Galβ4GlcβO$(CH_2)_2CH_2NH_2$ |
| 22 | Neu5Gcα3Galβ4GlcβO$(CH_2)_2CH_2NH_2$ |
| 23 | Neu5,9$Ac_2$α6GalNAcαO$(CH_2)_2CH_2NH_2$ |
| 24 | Neu5Gc9Acα6GalNAcαO$(CH_2)_2CH_2NH_2$ |
| 25 | Neu5Acα3GalβO$(CH_2)_2CH_2NH_2$ |
| 26 | Neu5Gcα3GalβO$(CH_2)_2CH_2NH_2$ |
| 27 | Neu5Acα6GalβO$(CH_2)_2CH_2NH_2$ |
| 28 | Neu5Gcα6GalβO$(CH_2)_2CH_2NH_2$ |
| 29 | Neu5,9$Ac_2$α3GalβO$(CH_2)_2CH_2NH_2$ |
| 30 | Neu5Gc9Acα3GalβO$(CH_2)_2CH_2NH_2$ |
| 31 | Neu5,9$Ac_2$α6GalβO$(CH_2)_2CH_2NH_2$ |
| 32 | Neu5Gc9Acα6GalβO$(CH_2)_2CH_2NH_2$ |
| 33 | Neu5Acα3Galβ3GalNAcβO$(CH_2)_2CH_2NH_2$ |
| 34 | Neu5Gcα3Galβ3GalNAcβO$(CH_2)_2CH_2NH_2$ |
| 35 | Neu5,9$Ac_2$α3Galβ3GalNAcβO$(CH_2)_2CH_2NH_2$ |
| 36 | Neu5Gc9Acα3Galβ3GalNAcβO$(CH_2)_2CH_2NH_2$ |
| 37 | Neu5,9$Ac_2$α6Galβ4GlcβO$(CH_2)_2CH_2NH_2$ |
| 38 | Neu5Gc9Ac6Galβ4GlcβO$(CH_2)_2CH_2NH_2$ |
| 39 | Neu5,9$Ac_2$α3Galβ4GlcβO$(CH_2)_2CH_2NH_2$ |
| 40 | Neu5Gc9Ac3Galβ4GlcβO$(CH_2)_2CH_2NH_2$ |
| 41 | Neu5Acα8Neu5Acα3Galβ4GlcβO$(CH_2)_2CH_2NH_2$ |
| 42 | Neu5Acα8Neu5Acα8Neu5Acα3Galβ4GlcβO$(CH_2)_2CH_2NH_2$ |
| 43 | Galβ4GlcβO$(CH_2)_2CH_2NH_2$ |
| 44 | Galβ4Glcβ$NH_2$ |
| 45 | Galβ4GlcNAcβO$(CH_2)_2CH_2NH_2$ |
| 51 | Galβ3GalNAcβO$(CH_2)_2CH_2NH_2$ |
| 52 | Galβ3GalNAcαO$(CH_2)_2CH_2NH_2$ |
| 53 | Galβ3GlcNAcβO$(CH_2)_2CH_2NH_2$ |
| 54 | Galβ4GlcNAc6SβO$(CH_2)_2CH_2NH_2$ |
| 55 | Neu5Acα3Galβ4(Fucα3)GlcNAcβO$(CH_2)_2CH_2NH_2$ |
| 56 | Neu5Gcα3Galβ4(Fucα3)GlcNAcβO$(CH_2)_2CH_2NH_2$ |
| 57 | Neu5Acα3Galβ4(Fucα3)GlcNAc6SβO$(CH_2)_2CH_2NH_2$ |
| 58 | Neu5Gcα3Galβ4(Fucα3)GlcNAc6SβO$(CH_2)_2CH_2NH_2$ |
| 59 | Galβ3GlcNAcβ3Galβ4GlcβO$(CH_2)_2CH_2NH_2$ |
| 60 | Neu5Acα3Galβ3GlcNAcβ3Galβ4GlcβO$(CH_2)_2CH_2NH_2$ |
| 61 | Neu5Gcα3Galβ3GlcNAcβ3Galβ4GlcβO$(CH_2)_2CH_2NH_2$ |
| 62 | Neu5Acα3Galβ4GlcNAc6SβO$(CH_2)_2CH_2NH_2$ |
| 63 | Neu5Gcα3Galβ4GlcNAc6SβO$(CH_2)_2CH_2NH_2$ |
| 64 | Neu5Acα8Neu5Acα3Galβ4GlcβO$(CH_2)_3NHCOCH_2(OCH_2CH_2)_6NH_2$ |
| 65 | Neu5Acα8Neu5Acα8Neu5Acα3Galβ4GlcβO$(CH_2)_3NHCOCH_2(OCH_2CH_2)_6NH_2$ |
| 66 | Neu5Acα6(Neu5Acα3)Galβ4GlcβO$(CH_2)_2CH_2NH_2$ |
| 67 | Neu5Acα6(Neu5Gcα3)Galβ4GlcβO$(CH_2)_2CH_2NH_2$ |
| 68 | Neu5Acα6(Kdnα3)Galβ4GlcβO$(CH_2)_2CH_2NH_2$ |
| 69 | Neu5Gcα8Neu5Acα3Galβ4GlcβO$(CH_2)_2CH_2NH_2$ |
| 70 | Kdnα8Neu5Acα3Galβ4GlcβO$(CH_2)_2CH_2NH_2$ |
| 71 | Neu5Acα8Kdnα6Galβ4GlcβO$(CH_2)_2CH_2NH_2$ |
| 72 | Neu5Acα8Neu5Gcα3Galβ4GlcβO$(CH_2)_2CH_2NH_2$ |
| 73 | Neu5Acα8Neu5Gcα6Galβ4GlcβO$(CH_2)_2CH_2NH_2$ |
| 74 | KDNα8Neu5Gcα3Galβ4GlcβO$(CH_2)_2CH_2NH_2$ |
| 75 | Neu5Gcα8Neu5Gc-α3Galβ4GlcβO$(CH_2)_2CH_2NH_2$ |
| 76 | Neu5Acα8Neu5Acα6Galβ4GlcβO$(CH_2)_2CH_2NH_2$ |
| 77 | Neu5GcMeα8Neu5Acα3Galβ4GlcβO$(CH_2)_2CH_2NH_2$ |
| 78 | Galα3Galβ4GlcNAcβO$(CH_2)_2CH_2NH_2$ |
| 79 | Galβ3GalNAcαO$(CH_2)_2CH_2NH_2$ |
| 80 | Galβ4(Fucα3)GlcNAcβO$(CH_2)_2CH_2NH_2$ |
| 81 | Neu5Acα8Neu5Acα3Galβ4GlcO$(CH_2)_2CH_2NH_2$ |
| 82 | Neu5Acα8Neu5Acα3(GalNAcβ4)Galβ4GlcO$(CH_2)_2CH_2NH_2$ |
| 83 | Neu5Acα3Galβ3(Fucα4)GlcNAcβO$(CH_2)_2CH_2NH_2$ |
| 84 | Galβ3(Fucα4)GlcNAcβO$(CH_2)_2CH_2NH_2$ |

TABLE 1-continued

| List of glycans fabricated on glycan microarrays. | |
|---|---|
| Glycan ID | Structure |
| 85 | Fucα2Galβ3(Fucα4)GlcNAcβO$(CH_2)_2CH_2NH_2$ |
| 86 | Neu5Gcα3Gal3(Fucα4)GlcNAcβO$(CH_2)_2CH_2NH_2$ |
| 87 | Neu5,9Ac2α3Galβ3(Fucα4)GlcNAcβO$(CH_2)_2CH_2NH_2$ |
| 88 | Neu9Ac5Gcα3Galβ3(Fucα4)GlcNAcβO$(CH_2)_2CH_2NH_2$ |

Sialoglycan Microarray Binding Assay

Slides were developed and analyzed as previously described (Padler-Karavani et al., 2012, *J Biol Chem,* 287: 22593-22608) with some modifications. Slides were rehydrated with $dH_2O$ and incubated for 30 min in a staining dish with 50° C. pre-warmed ethanolamine (0.05 M) in Tris-HCl (0.1 M, pH 9.0) to block the remaining reactive epoxy groups on the slide surface, then washed with 50° C. pre-warmed $dH_2O$. Slides were centrifuged at 200×g for 5 min then fitted with ProPlate™ Multi-Array 16-well slide module (Invitrogen) to divide into the sub-arrays (blocks). Slides were washed with PBST (0.1% Tween 20), aspirated, and blocked with 200 μL/sub-array of blocking buffer (PBS/OVA, 1% w/v ovalbumin, in PBS, pH 7.3) for 1 h at RT with gentle shaking. Next, the blocking solution was aspirated and 100 μL/block of purified antibodies in $16.5\text{-}4.5\times10^{-4}$ μg/mL diluted in PBS/OVA were incubated with gentle shaking for 2 h at RT. Slides were washed four times with PBST, then with PBS for 2 min. Bound antibodies were detected by incubating with secondary detection diluted in PBS, 200 μL/block at RT for 1 h, Cy3-anti-human IgG 0.4 μg/mL (Jackson ImmunoResearch). Slides were washed four times with PBST then with PBS for 10 min followed by removal from ProPlate™ Multi-Array slide module and immediately dipping in a staining dish with $dH_2O$ for 10 min with shaking, then centrifuged at 200×g for 5 min. Dry slides immediately scanned.

Array Slide Processing and Apparent $K_D$ Calculations

Processed slides were scanned and analyzed as described at 10 m resolution with a GenePix 4000B microarray scanner (Molecular Devices) using 350 gain. Image analysis was carried out with GenePix Pro 6.0 analysis software (Molecular Devices). Spots were defined as circular features with a variable radius as determined by the GenePix scanning software. Local background subtraction was performed. Apparent $K_D$ was calculated according to non-linear fit with one-site specific binding using GraphPad Prism 8.0.

Binding of Full-Length HuNative and HuRA9-23 IgG Antibodies to Cancer Cells

WiDr colon cancer cells were obtained from American Type Culture collection (ATCC), cells were grown in Dulbecco's Modified Eagle Medium (DMEM; biological industries) supplemented with 10% heat inactivated fetal bovine serum (FBS), 2 mM L-glutamine, 100 units/ml penicillin and 0.1 mg/ml streptomycin. For binding assays, cells were collected from plates using 10 mM EDTA. $3\times10^5$ cells were incubated with 5 ng/μl of full-length HuNative and HuRA9-23 IgGs diluted in FACS buffer (PBS with 0.5% fish gelatin) for 1 h on ice, followed by incubation with Cy3-AffiniPure goat-anti-human IgG diluted 1:100 (15 g/ml) in FACS buffer for 40 min on ice. Fluorescence was measured by CytoFLEX flow cytometry. For sialidase FACS assay, WiDr cells were collected from plates using 10 mM EDTA. $2\times10^5$ cells were divided into Eppendorf tubes and incubated for four hours at 37° C. with either PBS, 100 mU active *Arthrobacter ureafaciens* Sialidase (AUS) (EY Laboratories, San Mateo, CA, USA) or 100 mU inactive AUS (pre-incubated in 90° C. for 30 min) in PBS. Then, cells were washed with FACS buffer, stained with 1 μg/ml HuNative or HuRA9-23 full-length hIgG antibodies, followed by washing, secondary antibody labeling and fluorescence measurement, as described above.

Antibody Specificity by ELISA

Binding of HuNative and HuRA9-23 full-length hIgG antibodies to various glycans was tested by ELISA inhibition assay. 96 well plate was coated with $SLe^a$-PAA-Biotin (GlycoTech) in triplicates at 0.25 μg/well overnight at 4° C. Wells were blocked with blocking buffer. HuNativehIgG or HuRA9-23-hIgG antibodies at 0.16 μg/mL was pre-incubated with either specific or non-specific target antigens ($SLe^a$-PAA-Biotin and $Le^a$-PAA-Biotin or $SLe^x$-PAA-Biotin glycans, respectively) at 300-0.3 nM in blocking buffer. Antibody-glycan mixtures were incubated at 4° C. for two hours. Blocking buffer was removed from plate and antibody-glycan mixtures were added to the respective wells at 100 μl/well in triplicates, then incubated for two hours at room temperature. The plates were washed three times with PBST (PBS pH 7.4, 0.1% Tween) and subsequently incubated for 1 h at room temperature with HRP-goat-anti-human IgG 0.11 μg/ml in PBS. After washing three times with PBST, wells were developed with 140 μl of O-phenylenediamine in 100 mM citrate-$PO_4$ buffer, pH 5.5, and the reaction stopped with 40 μl of $H_2SO_4$ (4 M). Absorbance was measured at 490 nm on SpectraMax M3 (Molecular Devices). Specific binding was defined by subtracting the background readings obtained with the secondary antibody only.

Statistical Analysis

Statistical analysis conducted with Prism 8 with the specific methods as indicated in the figure legends.

Example 1. Humanization of mNative or mRA9-23 Antibodies

To reduce immunogenicity of the mouse-derived native 1116NS19.9 antibody and its YSD-derived mutant clone RA9-23 (mNative and mRA9-23, respectively) mutations were introduced based on DNA sequence homology with human germline antibodies, to generate their humanized versions (HuNative and HuRA9-23, respectively). Initially, the FR and CDRs of mNative and mRA9-23 were identified according to Kabat and these were compared to the database of human germline antibodies sequences, and those of the highest homology were selected for design of antibody humanization. The VH and VL of the mNative antibody have amino acid sequences as defined in SEQ ID NO: 1 and 2, respectively, and the VH and VL of the mRA9-23 antibody have amino acid sequences as defined in SEQ ID NO: 3 and 4, respectively (see sequence also sequence Table).

Figure 1B:
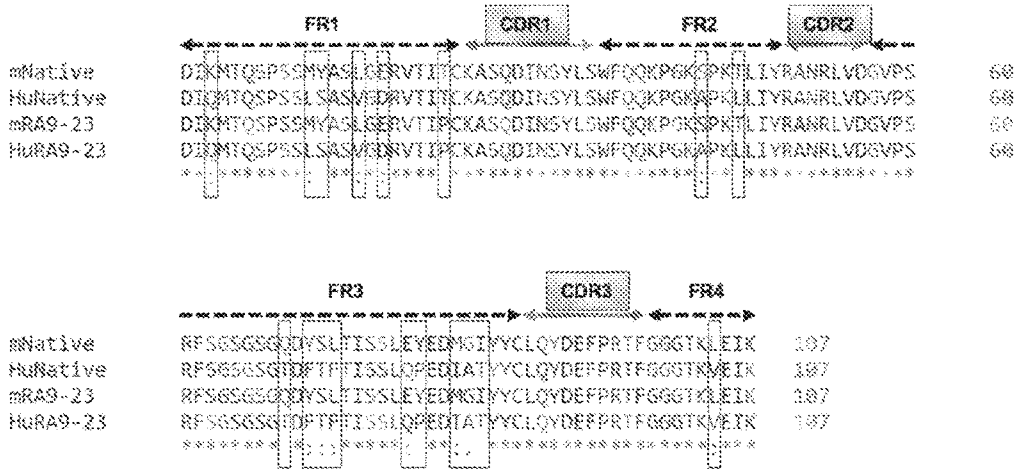

In the mNative antibody a total of 32 mutations were introduced to get the humanized HuNative antibody clone, including 15 mutation in VH region and 17 mutations in the VL region. The VH and VL of the HuNative antibody have amino acid sequences as defined in SEQ ID NO: 12 and 13, respectively. In the mRA9-23 antibody a total of 33 mutations were introduced to get the humanized HuRA9-23 antibody clone, including 16 mutations in VH region and 17 mutations in the VL region. The VH and VL of the mRA9-23 antibody have amino acid sequences as defined in SEQ ID NO: 14 and 15, respectively. Multiple sequence analysis of the relevant sequences is provided in FIG. 1. These mutations were introduced particularly in the FR regions while maintaining the CDRs sequences unchanged. To allow stabilization of the CDRs, in some cases, the FR amino acids closest to the CDRs in the mouse-derived clones were preserved also in the humanized antibodies, despite the fact that these were different in the homologous germline sequences (VH: FR2 'A' alanine that precedes CDR2; VH: FR3 'TT' two threonine that precedes CDR3; VL: FR2 'WF' tryptophan-phenylalanine that are found right after CDR1). Of note, the mRA9-23 clone differs from mNative by a total of 5 mutations (4 in VH, and 1 in VL), however in the humanized version HuRA9-23 the mutation in the first amino acid of VH was reverted back to that found in the mNative (VH 'K' lysine to VH 'E' glutamate).

Example 2. Characterization of HuNative and HuRA9-23 Antibodies

Figure 2:
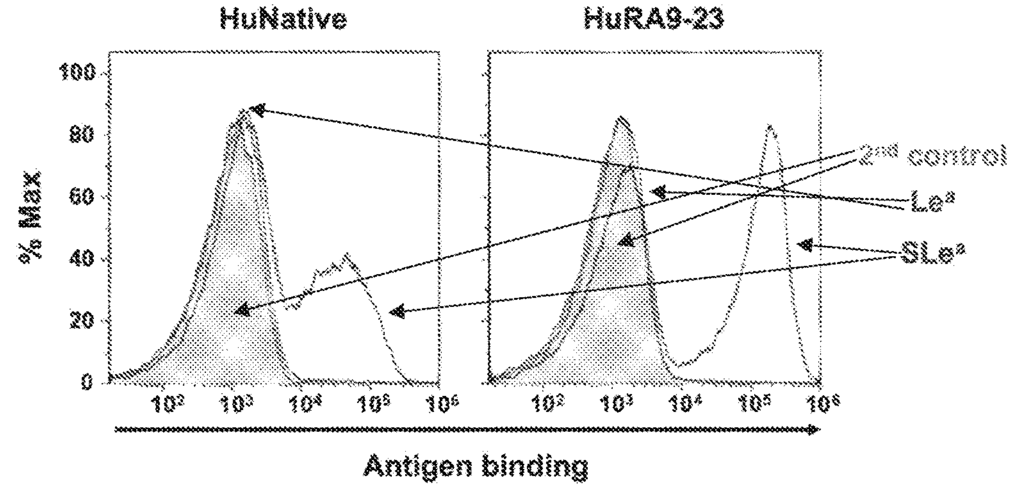
FIG. 2 shows binding of HuNative or HuRA9-23 to their specific antigen ($SLe^a$) or to their non-specific antigen ($Le^a$), as examined by FACS. For this purpose, yeast cells with surface expression of scFv fragments of HuNative or HuRA9-23 were incubated with either 0.5 μM $SLe^a$-PAA-Biotin, 0.5 μM $Le^a$-PAA-Biotin or FACS buffer for negative control, then antibody binding detected with secondary detection APC-streptavidin, and measured by CytoFLEX flow cytometry.
Figure 3:
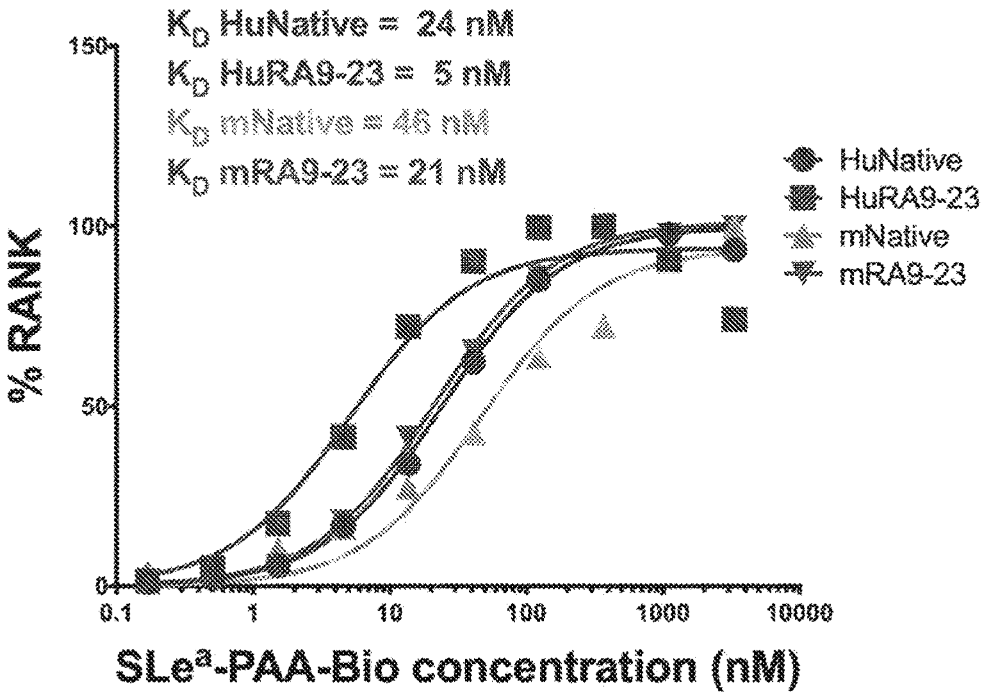
FIG. 3 shows the binding capacity and calculated affinities of mouse-derived and humanized scFv fragments (mNative, mRA9-23, HuNative and HuRA9-23) as expressed on yeast cell. Binding of scFv clones to antigen was examined at 10 serial dilutions of $SLe^a$-PAA-Biotin (3333-0.16 nM).

To characterize the properties of the humanized antibodies, the scFv fragments of both HuNative (having amino acid sequence SED ID NO: 22) and HuRA9-23 (having amino acid sequence SED ID NO: 23, see also Sequence Table) were each cloned into yeast surface display system (YSD), followed by induction of their expression on the surface of these yeast cells, then binding to antigens examined by FACS. Both scFv-HuNative and scFv-HuRA9-23 yeast variants showed strong binding to the specific antigen SLe$^a$ antigen, while no binding at all to the non-specific Le$^a$ antigen that lacks terminal sialic acid similar to the negative control staining (FIG. 2). To further evaluate the affinity of humanized scFvs, their binding was examined by FACS against serially diluted antigen concentrations. Affinity of scFv expressed on yeast cells was then calculated from binding over the range of antigen titration and apparent $K_D$ (affinity) was calculated from saturation curves (FIG. 3), according to non-linear fit with one-site-specific binding using GraphPad Prism 8.0 and presented in Table 2. It can be seen that humanized (HuNative) antibody has 2 times lower $K_D$ than the mNative antibody, whereas the $K_D$ of HuRA9-23 is about 1 order of magnitude lower than the $K_D$ of the mNative antibody and about 4 times lower than the $K_D$ of mRA9-23 clone.

TABLE 2

]$K_D$ of humanized scFvs

| | $K_D$ (nM) |
|---|---|
| mNative | 46 |
| HuNative | 24 |
| mRA9-23 | 21 |
| HuRA9-23 | 5 |

Figure 4:
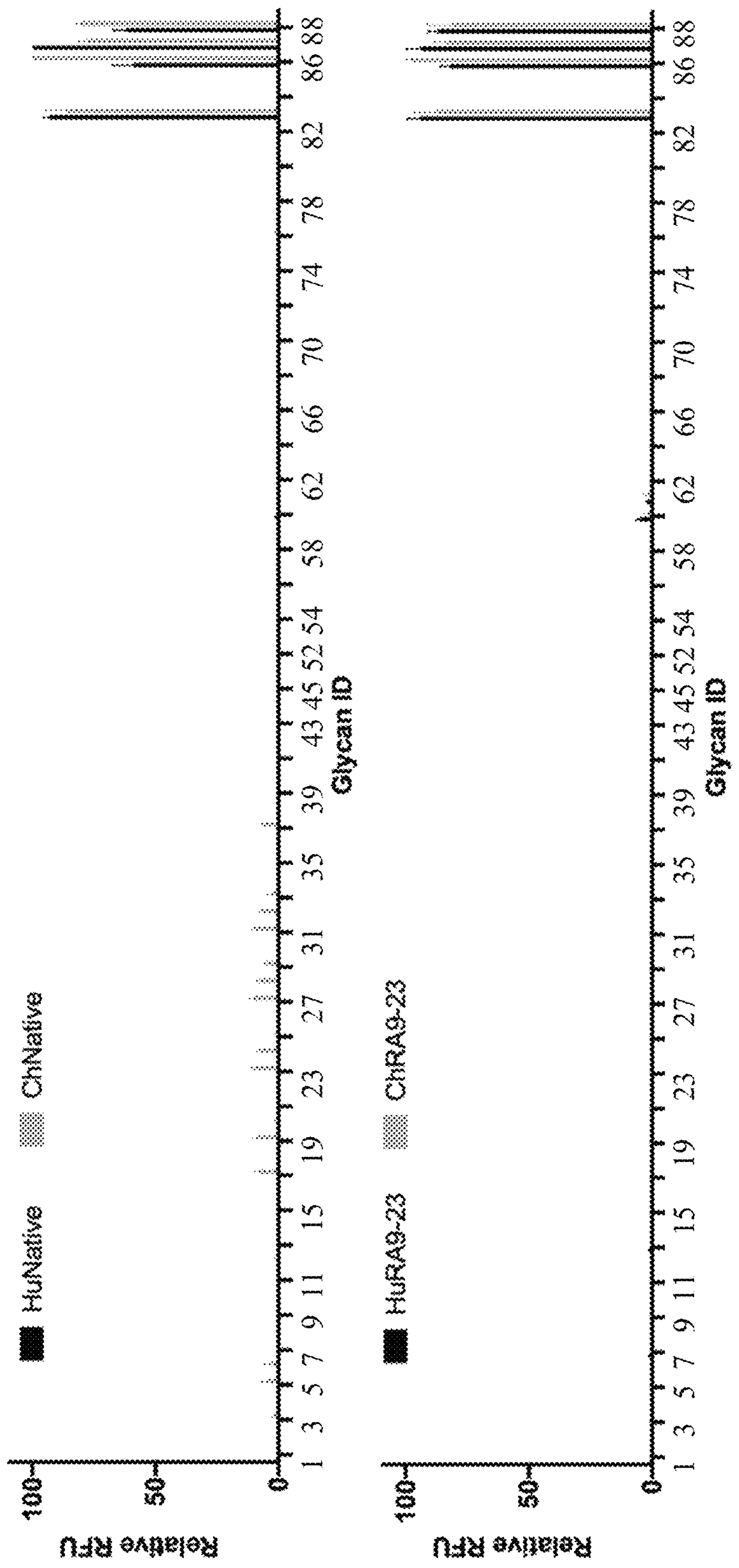
FIG. 4 shows the binding of full-length antibodies of the Native and RA9-23 humanized and chimeric IgGs against diverse glycans (HuNative-hIgG and HuRA9-23-hIgG labeled here as HuNative and HuRA9-23, respectively; mNative-hIgG and mRA9-23-hIgG labeled here as ChNative and ChRA9-23, respectively). Binding was examined at three concentrations between 0.245-0.016 ng/pd by a sialoglycan microarray (List of glycans in Table 1).
Figure 5:
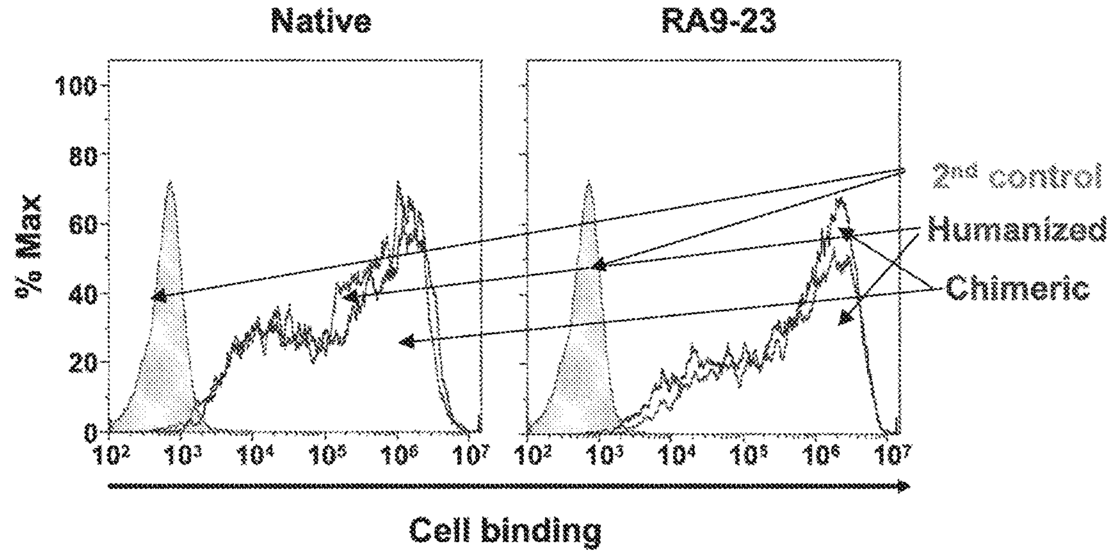
FIG. 5 shows the binding of humanized full-length antibodies to cancer cells. Binding of chimeric and humanized of Native (left panel) and RA9-23 (right panel) IgGs to SLea-expressing WiDr cancer cells was examined by FACS at 5 ng/L. Representative of three independent experiments.

To further characterize the humanized variants, VH and VL sequences were clone into full length human IgG p3BNC expression vectors by Gibson assembly (HuNative-hIgG and HuRA9-23-hIgG). Similarly, VH and VL sequences of the mouse-derived antibodies were cloned into same expression vectors to form chimeric antibodies (mNative-hIgG and mRA9-23-hIgG; also referred as ChNative and ChRA9-23, respectively). Full length antibodies were produced by transfection of HEK-293A cells by polyethylenimine (PEI). Antibodies were purified by protein A and subjected to specificity and affinity measurements by high-throughput glycan microarray. Specificity assay against a variety of glycans emphasized the high selectivity of these antibodies which are highly specific to SLea related structures. The four highly bound glycans are SLe$^a$ with either Neu5Ac (AcSLe$^a$) or Neu5Gc (GcSLe$^a$) as the terminal sialic acid (glycan #83 and #86, respectively) and the 9-O-acetylated versions 9-O-AcSLe$^a$ (glycan #87), 9-O-GcSLe$^a$ (glycan #88). Glycans without sialic acid, as Le$^a$ (glycan #84) or Fucose Neu5Ac/NeuGc-α-2-3-Gal-β1-3-GlcNAc-β1-3-Lac-β (glycan #60/61) were bound in a much lower manner or were not bound at all (FIG. 4). Apparent $K_D$ analysis showed that both humanized variants have similar affinities to glycans #83 and #86-88, with a small advantage to HuRA9-23 (Table 3). In addition, the humanized antibodies showed similar ability as the an antibody having human Fc (chimeric antibody) to bind SLe$^a$-positive WiDr colon cancer cell line by FACS staining (FIG. 5).

TABLE 3

Apparent $K_D$ measured on full length antibodies in glycan microarray.

| | $K_D$ (nM) | | | |
|---|---|---|---|---|
| Glycan ID | 83 | 86 | 87 | 88 |
| HuNative | 0.42 | 0.77 | 0.38 | 0.83 |
| HuRA9-23 | 0.10 | 0.12 | 0.10 | 0.12 |

Figure 6A:
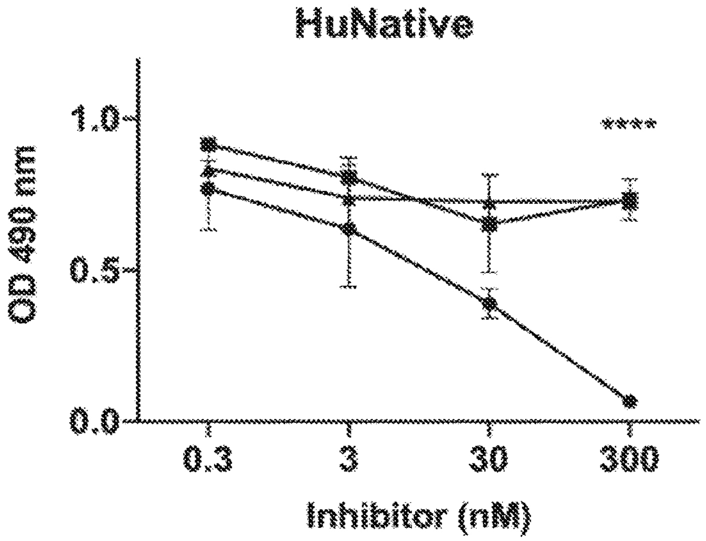
FIG. 6A-6B shows the specificity of the full-length HuNative (FIG. 6A) and HuRA9-23 (FIG. 6B) IgGs examined by ELISA inhibition assay against coated $SLe^a$-PAA-biotin, after pre-incubation of the antibody with specific ($SLe^a$) or non-specific glycans ($SLe^x$ and $Le^a$). ****$p<0.0001$.
Figure 6B:
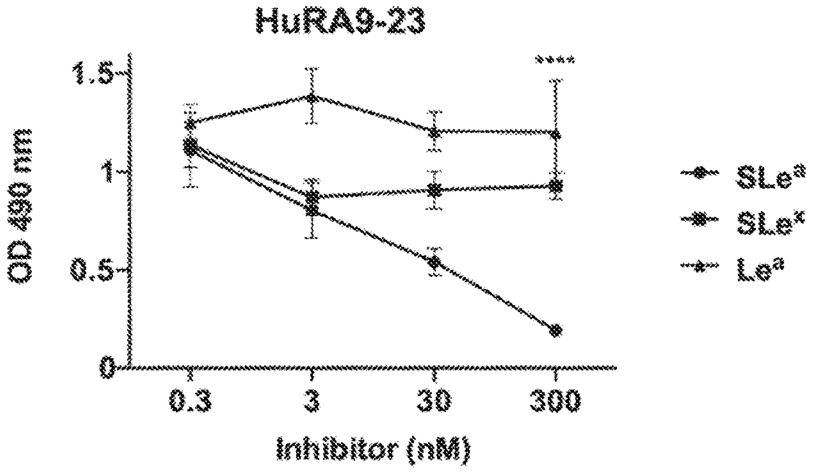
Figure 7A:
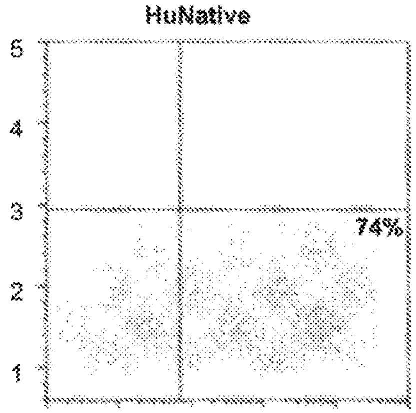
FIG. 7A-7G shows antibodies cancer cell binding specificity as demonstrated by treatment of cells with *Arthrobacter ureafaciens* Sialidase (AUS) that abrogated binding of HuNative (FIG. 7C—with active AUS) and HuRA9-23 (FIG. 7F—with active AUS) IgGs to $SLe^a$-expressing WiDr cells, in comparison to direct binding of the antibody (FIG. 7A—HuNative and FIG. 7D—HuRA9-23) or their binding to cells treated with heat-inactivated AUS (FIG. 7B—HuNative, FIG. 7E—HuRA9-23); control—FIG. 7G.
Figure 7B:
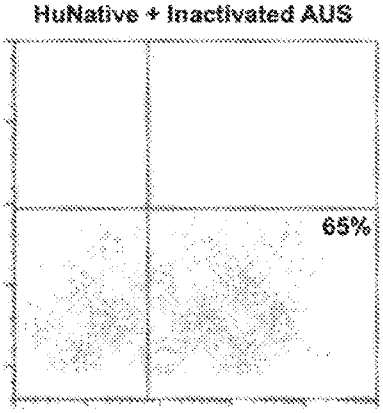
Figure 7C:
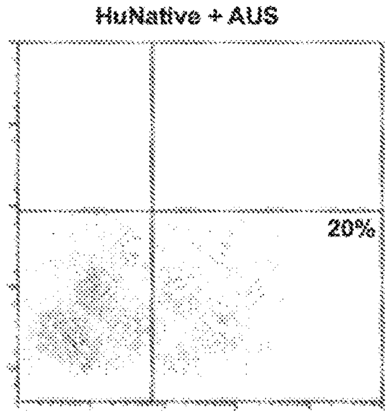
Figure 7D:
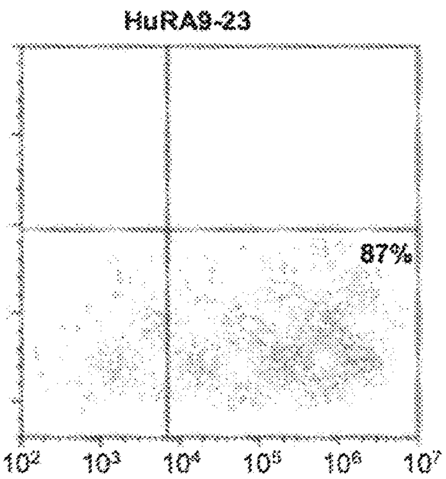
Figure 7E:
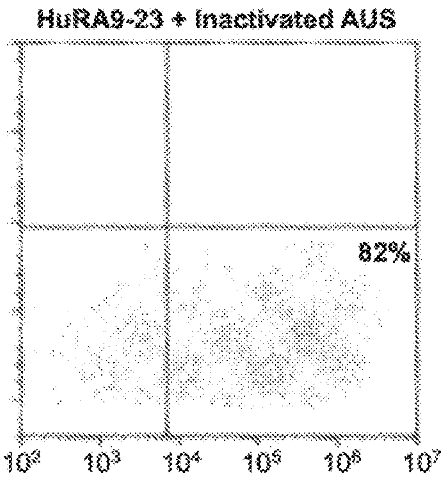
Figure 7F:
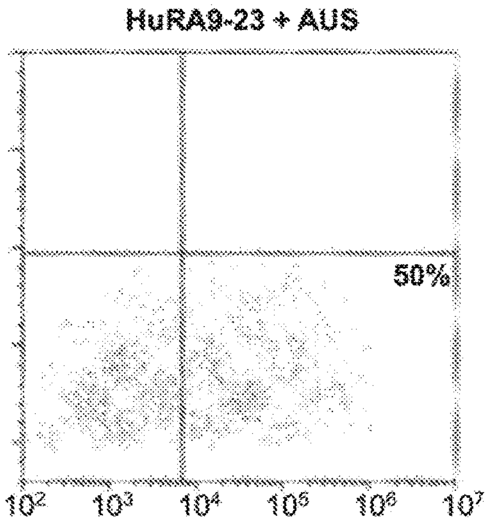
Figure 7G:
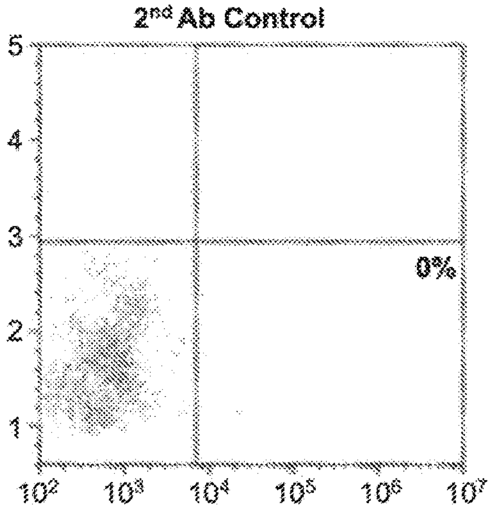

Specificity of the full-length humanized antibodies was further demonstrated by ELISA inhibition assay, in which binding of HuNative-hIgG or HuRA9-23-hIgG to SLe$^a$ was inhibited only with the specific glycan SLe$^a$, but not with the closely-related glycans SLeX or Le$^a$ (FIGS. 6 and 9). Removal of sialic acids from the cell surface by a sialidase treatment dramatically reduced the binding of humanized antibodies to WiDr cells, thus showing the importance of sialic acid for the antibodies recognition (FIG. 7). Altogether, these data indicate that humanized antibodies maintain high specificity, affinity and cell recognition characteristics as the original mouse-derived antibodies, or greater.

Example 3. Reduced Immunogenicity of Humanized Antibody Clones

Immunogenicity of humanized antibody clones was evaluated by analysis of scFv recognition by pooled human IgG obtained from thousands of human donors (IVIg; Gamma Gard). For this purpose, IVIg was first pre-cleared from anti-yeast reactivity by serial incubations with yeast cells, then binding to scFv-expressing yeast cells was examined by FACS. Expression of scFv on yeast (Native-YSD and RA9-23-YSD) was examined by mouse-anti-c-Myc and pooled human IgG binding detected with anti-human IgG, and double positive labeling of scFv-expressing yeast cells was examined. The results are presented in FIG. 8. The ratio of positive/negative IVIg labeling indicate that that IVIg had reduced binding to the HuNative and HuRA9-23 compared to the mouse variants mNative and mRA9-23 (FIG. 8). In each clone, the percentage ratio of (% IVIg-positive cells/% IVIg-negative cells) calculated for the three IVIg concentrations (25, 50 and 100 ng/μl) was averaged and normalized to mNative as the maximal signal.

Figure 8A:
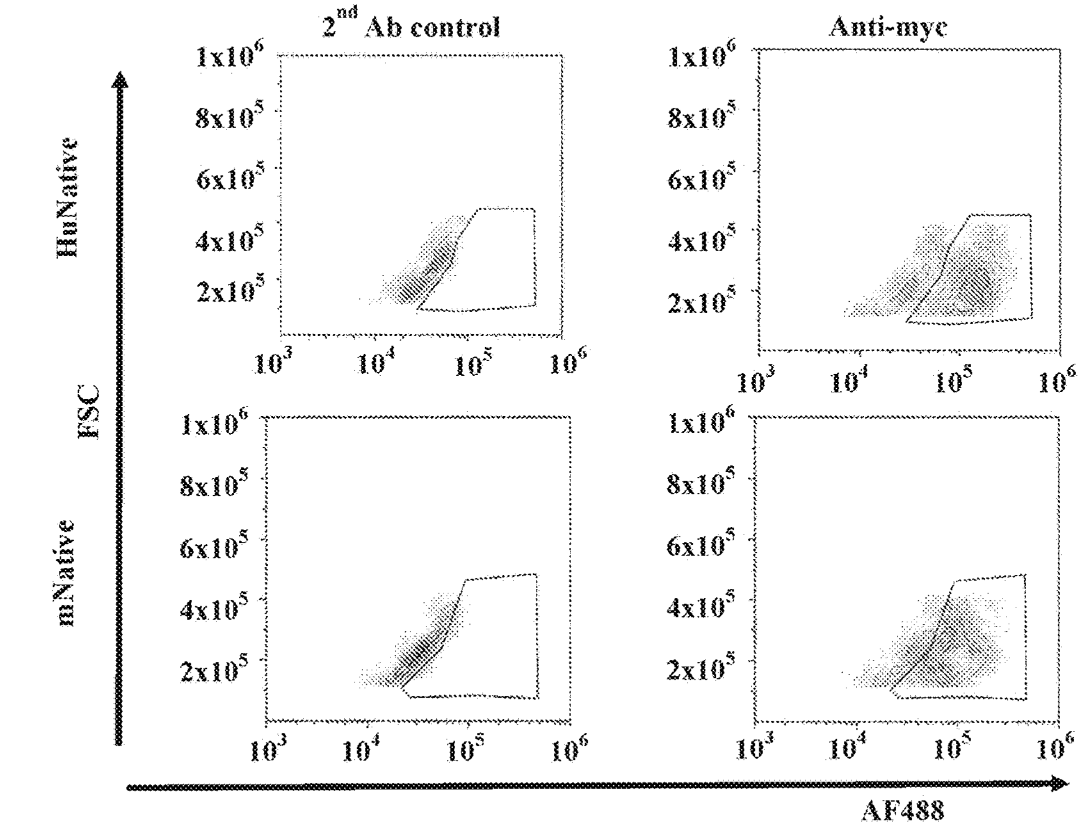
FIG. 8A-8F shows reduced immunogenicity of humanized antibodies. Binding of pooled human IgG (pre-cleared of anti-yeast reactivity; yeast-purified IVIg) at 25 ng/μl, 50 ng/μl and 100 ng/μl to scFv-HuNative and scFv-HuRA9-23 yeast cells compared to scFv-mNative and scFv-mRA9-23 yeast cells. Cells were first gated for scFv presenting cells by the AF488 fluorescence (stained by mouse-anti-c-Myc followed by Alexa-Fluor-488-goat-anti-mouse IgG1) (FIG. 8A and FIG. 8C). Positive IVIg binding on the gated scFv presenting cells was then determined by double positive signal of scFv presentation by c-myc labeling (AF488) and by binding of IVIg (Cy3; IVIg followed by Cy3-anti-human IgG Fe specific) (FIG. 8B and FIG. 8D). Then, IVIg-positive cells and IVIg-negative cells were separately gated (FIG. 8E; exemplified gating for mNative cells labeled with IVIg at 25 ng/μl), and in each IVIg concentration the percent of IVIg-positive cells was divided by the percent of IVIg-negative cells. In each clone, the percentage ratio of (% IVIg-positive cells/% IVIg-negative cells) calculated for the three IVIg concentrations (25, 50 and 100 ng/μl) was averaged. This analysis revealed that the percentage ratio was highest in mNative and it was reduced in the humanized clones: mNative (42.1±2.1%), mRA9-23 (28.8±2.7%), HuNative (11.8±1.4%), HuRA9-23 (7.2±1.5%). Then, the ratios were normalized to mNative yeast cells IVIg percent ratio, that was referred as the maximal signal (100%) (FIG. 8F). These data show a reduced immunogenicity of about 35% of mRA9-23 scFv in comparison to mNative, reduction of about 74% in immunogenicity of HuNative compared with mNative, and reduction of about 78% of HuRA9-23 compared with mRA9-23 (FIG. 8F). Representative of two independent experiments. One way ANOVA, Tukey,  $p<0.01$, * $p<0.001$, ****$p<0.0001$.
Figure 8B:
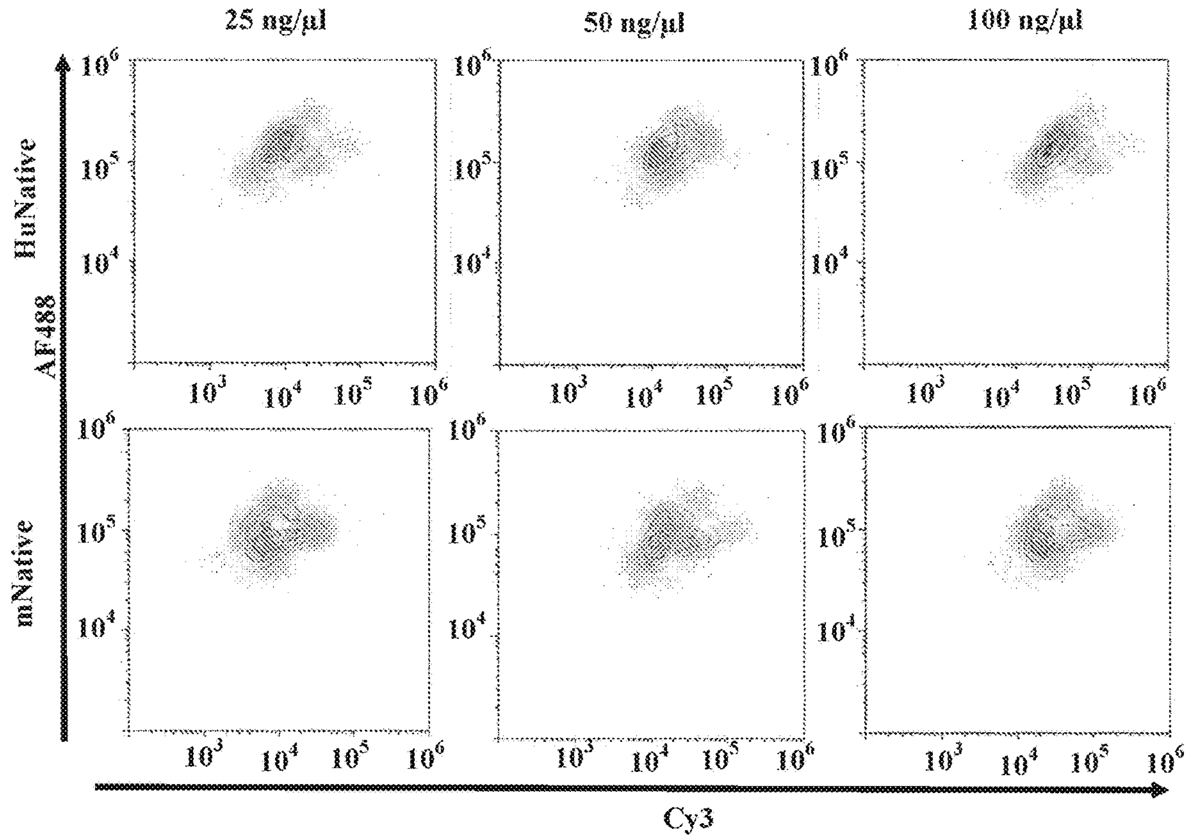
Figure 8C:
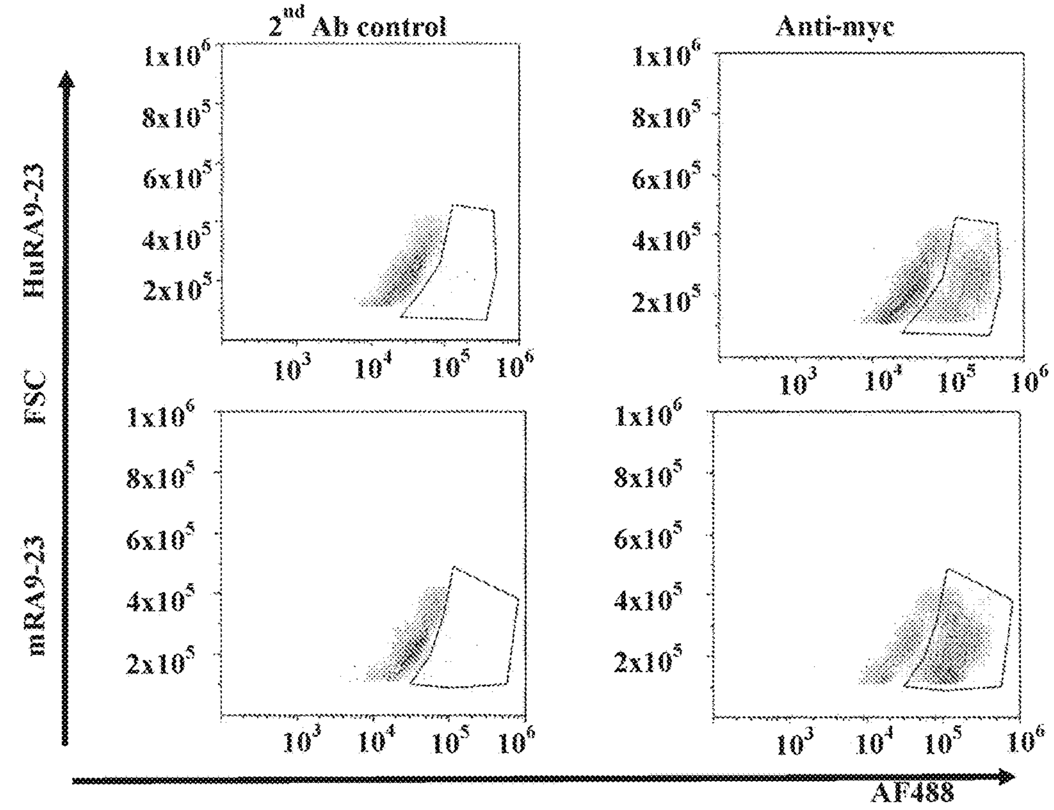
Figure 8D:
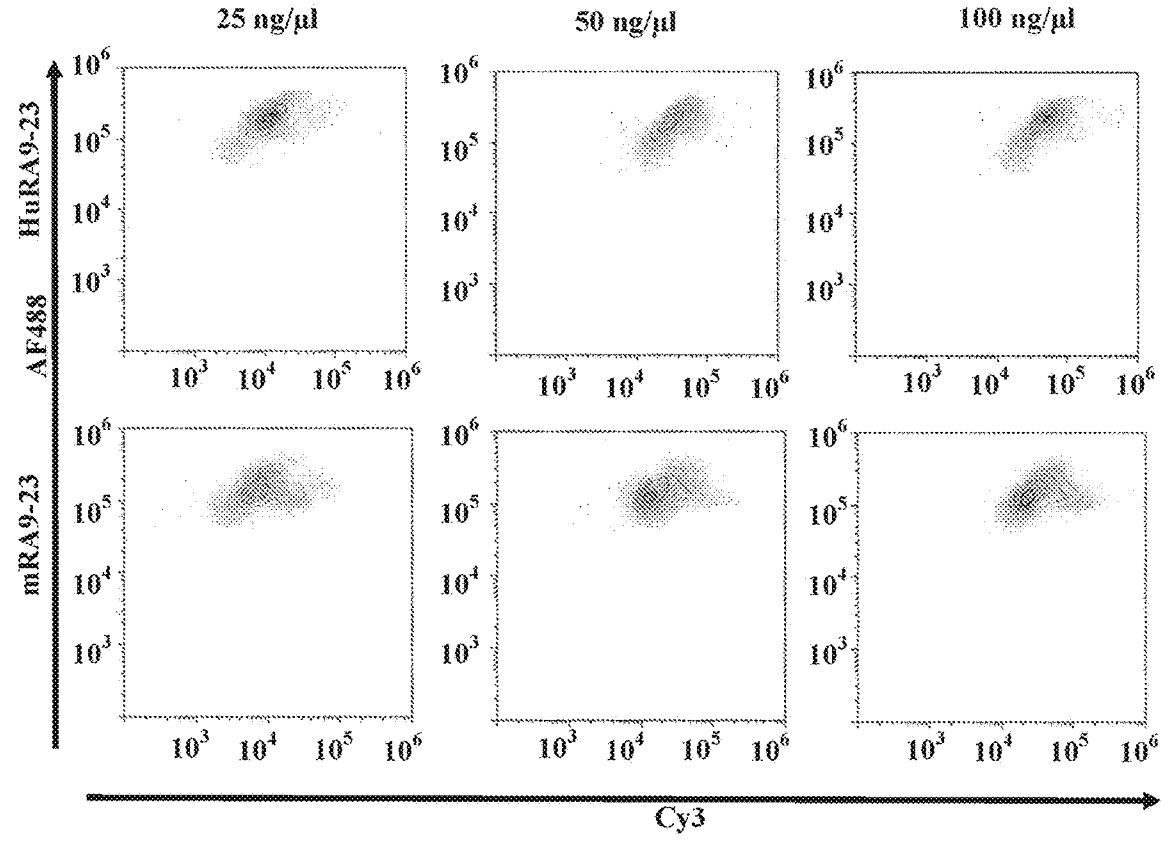
Figure 8E:
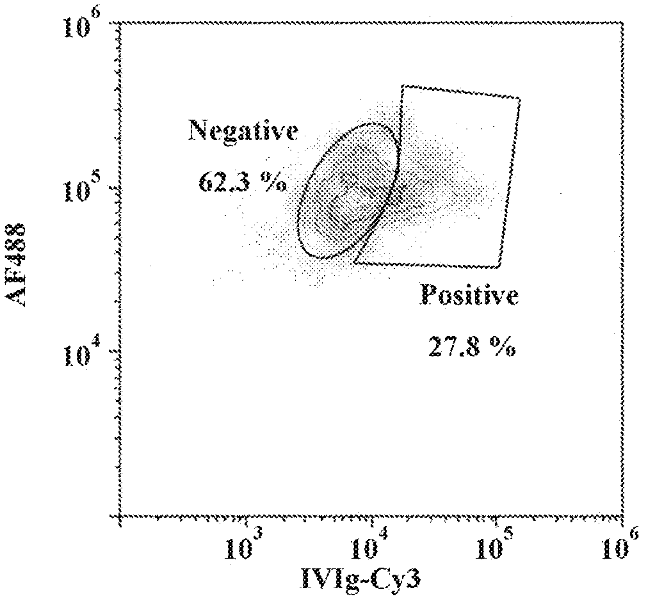
Figure 8F:
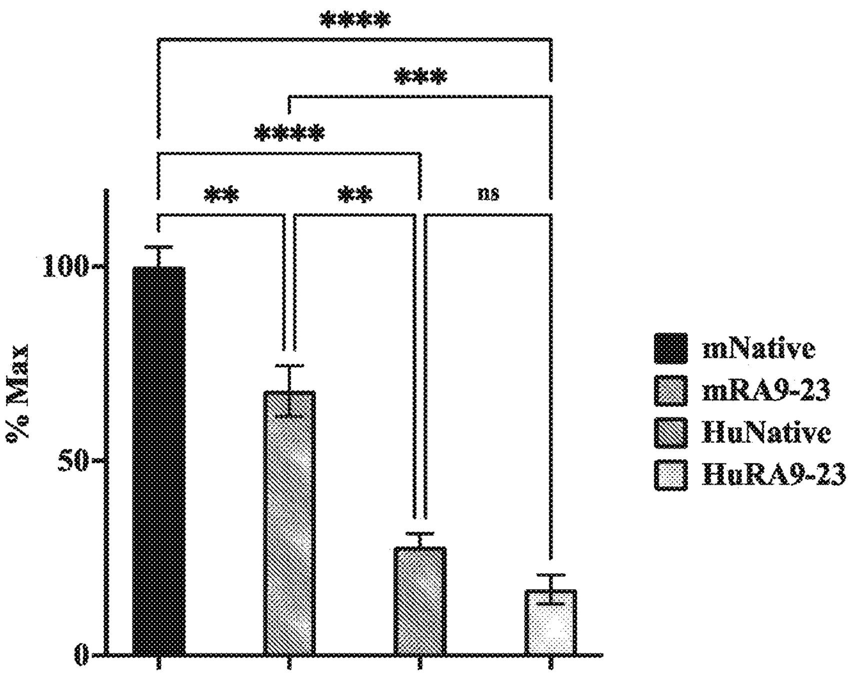
Figure 9A:
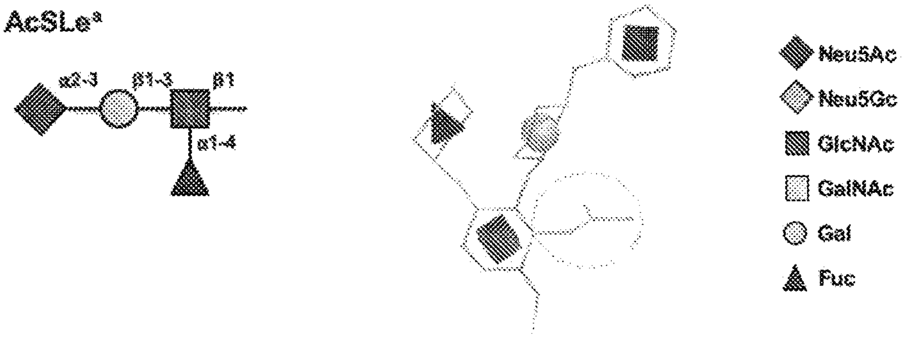
FIG. 9A-9I shows the structures of AcSLeA (FIG. 9A) and closely related glycans.
Figure 9B:
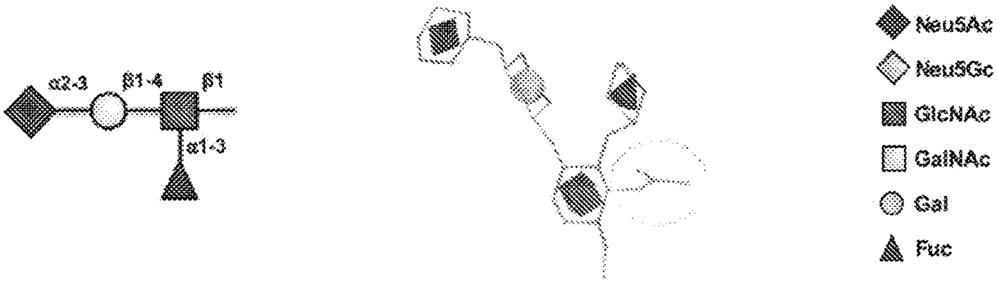
Figure 9C:
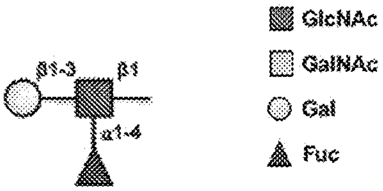
Figure 9D:
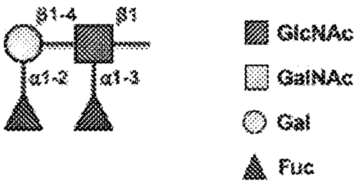
Figure 9E:
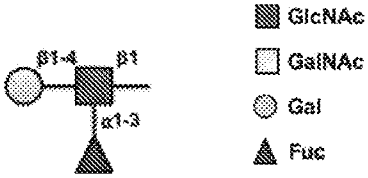
Figure 9F:
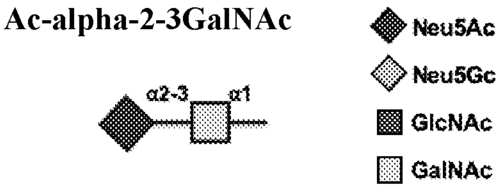
Figure 9G:
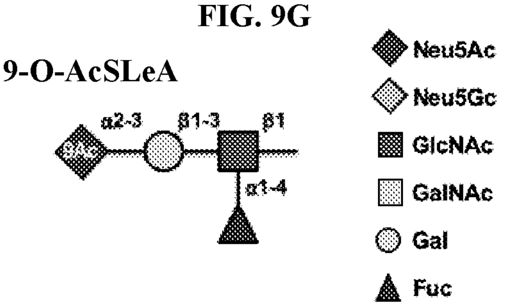
Figure 9H:
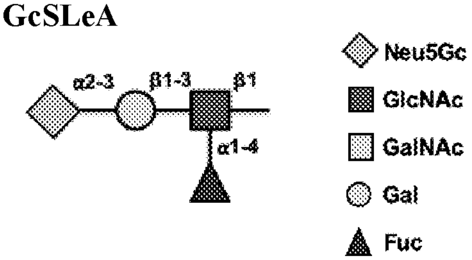
Figure 9I:
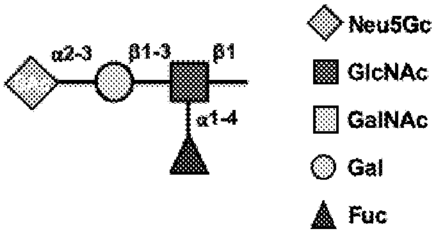

Summarizing the results it can be seen that the HuNative IVIg binding is 3.5 fold lower compared to mNative IVIg binding. Similarly, the HuRA9-23 IVIg binding is 4 fold lower compared to mRA9-23 IVIg binding (FIG. 8 HuNative has up to 74% reduced immunogenicity as compared with mNative, and HuRA9-23 has a up to 78% reduced immunogenicity as compared with mRA9-23 (FIG. 8F). Interestingly, mRA9-23 has up to 35%, reduced immunogenicity compared with mNative. In addition, the shape of the IVIg-positive mouse-derived clones seems to bulge out to the right clearly showing a separate population of the IVIg bound antibodies on the yeast cells (FIG. 8). Together, these data imply that the humanization process had decreased recognition of the antibody fragments with a large collection of pooled human IgG. In addition, it also suggests that engineered chimeric antigen receptor T cells (CAR T), in which the targeting moiety is actually expressed as scFv fragments would potentially have reduced recognition by human patient antibodies. This reduced immunogenicity of scFv is likely to support more stable CAR clones with potentially reduced risk of cytokine storm or other immunological events. Therefore, the humanized antibodies has a great potential as a therapeutic and diagnostic agents, with high specificity and affinity and less side effects of immune response against mouse-derived clones.

Although the present invention has been described herein above by way of preferred embodiments thereof, it can be modified, without departing from the spirit and nature of the subject invention as defined in the appended claims.

The invention claimed is:

1. A humanized monoclonal antibody (mAb) that binds specifically to sialyl Lewis A glycan (SLeA), a fragment of the humanized mAb or a conjugate thereof, comprising an antigen binding domain comprising a heavy-chain variable domain (VH) and a light-chain variable domain (VL), wherein the VH and the VL each comprises three complementarity determining regions (CDRs) and four framework regions (FR), wherein the VH-CDRs 1 and 3 comprise amino acid sequences SEQ ID NOs: 5 and 7, respectively, the VH-CDR2 comprises an amino acid sequence selected from SEQ ID NOs: 6 and 11, the VL-CDRs 1, 2, and 3 comprise amino acid sequences SEQ ID NOs: 8, 9, and 10, respectively, the VH-FR 1, 2, and 3 comprise amino acid sequences SEQ ID NOs: 24, 25, and 26, respectively, the VH-FR4 comprises an amino acid sequence selected from SEQ ID NOs: 27 and 32, the VL-FR1 comprises an amino acid sequence selected from SEQ ID NOs: 28 and 33, and the VL-FR 2, 3, and 4 comprise amino acid sequences SEQ ID NOs: 29, 30, and 31, respectively.

2. The humanized mAb, fragment, or conjugate thereof according to claim 1, wherein (i) the VH comprises amino acid sequence SEQ ID NO: 12 and the VL comprises amino acid sequence SEQ ID NO: 13; (ii) the VH comprises amino acid sequence SEQ ID NO: 14 and the VL comprises amino acid sequence SEQ ID NO: 15; (iii) the VH comprises amino acid sequence SEQ ID NO: 12 and the VL comprises amino acid sequence SEQ ID NO: 15; (iv) the VL comprises amino acid sequence SEQ ID NO: 13 and the VH comprises amino acid sequence SEQ ID NO: 14, or (v) the VH comprises an amino acid sequence selected from SEQ ID NOs: 12 and 14, and the VL comprises an amino acid sequence selected from SEQ ID NOs: 13 and 15.

3. The humanized mAb, fragment, or conjugate thereof according claim 1, wherein said antibody or fragment is characterized by at least one of:

(i) binds SLeA glycan with an equilibrium dissociation constant ($K_D$) of from about 0.1 to about 30 nM according to a non-linear fit; or (ii) the fragment is a single chain variable fragment (scFv).

4. The fragment according to claim 3, wherein the scFv comprises an amino acid sequence selected from SEQ ID NOs: 22 and 23.

5. A chimeric antigen receptor (CAR) comprising the humanized mAb or fragment thereof according to claim 1.

6. The CAR according to claim 5, comprising the humanized mAb fragment and wherein the fragment is a single chain variable fragment (scFv).

7. The CAR according to claim 6, wherein: (i) the VH comprises amino acid sequence SEQ ID NO: 12 and the VL comprises amino acid sequence SEQ ID NO: 13; (ii) the VH comprises amino acid sequence SEQ ID NO: 14 and the VL comprises amino acid sequence SEQ ID NO: 15; (iii) the VH comprises amino acid sequence SEQ ID NO: 12 and the VL comprises amino acid sequence SEQ ID NO: 15; or (iv) the VL comprises amino acid sequence SEQ ID NO: 13 and the VH comprises amino acid sequence SEQ ID NO: 14.

8. The CAR according to claim 5, comprising an scFv having an amino acid sequence selected from SEQ ID NOs: 22 and 23.

9. The CAR according to claim 5, wherein the CAR comprises a transmembrane domain (TM domain), one or more costimulatory domains and an activation domain.

10. The CAR according to claim 9, wherein the TM domain is a TM domain of a receptor selected from CD28 and CD8, or an analog thereof.

11. The CAR according to claim 9, wherein the costimulatory domain is selected from a costimulatory domain of a protein selected from CD28, 4-1BB, OX40, iCOS, CD27, CD80, CD70, an analog thereof or any combination thereof.

12. The CAR according to claim 9, wherein the antigen binding domain is linked to the TM domain via a spacer.

13. The CAR according to claim 9, wherein the activation domain is selected from FcRγ and CD3-ζ activation domains.

14. The CAR according to claim 5, further comprising a leading peptide.

15. The CAR according to claim 5, comprising an scFv comprising an amino acid sequence selected from SEQ ID NOs: 22 and 23, a TM domain of a receptor selected from CD28 and CD8, a costimulatory domain selected from the domain of CD28, 4-1BB, OX40 or a combination thereof, and an activation domain selected from FcRγ and CD3-ζ activation domains.

16. A nucleic acid molecule encoding at least one chain of the humanized mAb or fragment thereof according to claim 1 or a CAR comprising the humanized monoclonal antibody or fragment thereof.

17. The nucleic acid molecule according to claim 16, (i) encoding an amino acid sequence selected from SEQ ID NOs: 12, 13, 14, 15, 22, 23, a combination of SEQ ID NO: 12 and SEQ ID NOs: 13 or 15, and a combination of SEQ ID NOs: 14 and SEQ ID NOs: 13 or 15; or (ii) comprising a nucleic acid sequence selected from SEQ ID NOs: 16, 17, 18, 19, a combination of SEQ ID NO: 16 and SEQ ID NOs: 17 or 19, a combination of SEQ ID NO: 18 and SEQ ID NOs: 17 or 19, and a conservative variant thereof.

18. A cell comprising the humanized mAb or fragment thereof according to claim 1, a CAR comprising the humanized mAb or fragment thereof, or a nucleic acid molecule encoding the humanized mAb or fragment thereof, or the CAR.

19. The cell according to claim 18, wherein the cell expresses or is capable of expressing the CAR.

20. The cell according to claim 18, wherein the cell is selected from a T cell and a natural killer (NK) cell.

21. A composition comprising a plurality of one or more of the humanized mAbs or fragments thereof, or conjugates thereof according to claim 1, a CAR comprising the mAb or fragments thereof, or a cell comprising the mAb or fragments thereof, or said CAR.

* * * * *

```
                    SEQUENCE LISTING


<160> NUMBER OF SEQ ID NOS: 38

<210> SEQ ID NO 1
<211> LENGTH: 115
<212> TYPE: PRT
<213> ORGANISM: Mus musculus

<400> SEQUENCE: 1

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Val Ser Arg Asp Asp Ser Lys Ser Arg
65                  70                  75                  80

Val Tyr Leu Gln Met Asn Ser Leu Arg Val Glu Asp Thr Gly Thr Tyr
                85                  90                  95

Tyr Cys Thr Thr Arg Phe Ala Tyr Trp Gly Gln Gly Thr Leu Val Thr
            100                 105                 110

Val Ser Ala
        115


<210> SEQ ID NO 2
<211> LENGTH: 107
<212> TYPE: PRT
<213> ORGANISM: Mus musculus

<400> SEQUENCE: 2

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80
```

```
Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105


<210> SEQ ID NO 3
<211> LENGTH: 115
<212> TYPE: PRT
<213> ORGANISM: Artificial Sequence
<220> FEATURE:
<223> OTHER INFORMATION: Synthesized Sequence

<400> SEQUENCE: 3

Lys Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Gly Asn Lys Gly Asn Asn His Ala Thr Asn Tyr Ala Glu
    50                  55                  60

Ser Val Lys Gly Arg Phe Thr Val Ser Arg Asp Asp Ser Lys Ser Arg
65                  70                  75                  80

Val Tyr Leu Gln Met Asn Ser Leu Arg Val Glu Asp Thr Gly Thr Tyr
                85                  90                  95

Tyr Cys Thr Thr Arg Phe Ala Tyr Trp Gly Gln Gly Thr Pro Val Thr
            100                 105                 110

Val Pro Ala
        115


<210> SEQ ID NO 4
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 4

Asp Ile Lys Met Thr Gln Ser Pro Ser Ser Met Tyr Ala Ser Leu Gly
1               5                   10                  15

Glu Arg Val Thr Ile Pro Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105


<210> SEQ ID NO 5
<211> LENGTH: 5
<212> TYPE: PRT
<213> ORGANISM: Artificial Sequence
<220> FEATURE:
<223> OTHER INFORMATION: Synthesized Sequence
```

<400> SEQUENCE: 5

```
Asp Ala Trp Met Asp
1               5
```

<210> SEQ ID NO 6
<211> LENGTH: 19
<212> TYPE: PRT
<213> ORGANISM: Artificial Sequence
<220> FEATURE:
<223> OTHER INFORMATION: Synthesized Sequence

<400> SEQUENCE: 6

```
Glu Ile Gly Asn Lys Gly Asn Asn His Ala Thr Tyr Tyr Ala Glu Ser
1               5                   10                  15

Val Lys Gly
```

<210> SEQ ID NO 7
<211> LENGTH: 4
<212> TYPE: PRT
<213> ORGANISM: Artificial Sequence
<220> FEATURE:
<223> OTHER INFORMATION: Synthesized Sequence

<400> SEQUENCE: 7

```
Arg Phe Ala Tyr
1
```

<210> SEQ ID NO 8
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 8

```
Lys Ala Ser Gln Asp Ile Asn Ser Tyr Leu Ser
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 9

```
Arg Ala Asn Arg Leu Val Asp
1               5
```

<210> SEQ ID NO 10
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 10

```
Leu Gln Tyr Asp Glu Phe Pro Arg Thr Phe
1               5                   10
```

<210> SEQ ID NO 11
<211> LENGTH: 19
<212> TYPE: PRT
<213> ORGANISM: Artificial Sequence
<220> FEATURE:
<223> OTHER INFORMATION: Synthesized Sequence

<400> SEQUENCE: 11

```
Glu Ile Gly Asn Lys Gly Asn Asn His Ala Thr Asn Tyr Ala Glu Ser
1               5                   10                  15

Val Lys Gly
```

<210> SEQ ID NO 12
<211> LENGTH: 115
<212> TYPE: PRT
<213> ORGANISM: Homo sapiens

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Thr Arg Phe Ala Tyr Trp Gly Gln Gly Thr Leu Val Thr
            100                 105                 110

Val Ser Ser
        115
```

<210> SEQ ID NO 13
<211> LENGTH: 107
<212> TYPE: PRT
<213> ORGANISM: Homo sapiens

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Arg
                85                  90                  95

Thr Phe Gly Gly Gly Thr Lys Val Glu Ile Lys
            100                 105
```

<210> SEQ ID NO 14
<211> LENGTH: 115
<212> TYPE: PRT
<213> ORGANISM: Artificial Sequence
<220> FEATURE:
<223> OTHER INFORMATION: Synthesized Sequence

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Gly Asn Lys Gly Asn Asn His Ala Thr Asn Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Thr Arg Phe Ala Tyr Trp Gly Gln Gly Thr Pro Val Thr
            100                 105                 110

Val Pro Ser
        115


<210> SEQ ID NO 15
<211> LENGTH: 107
<212> TYPE: PRT
<213> ORGANISM: Artificial Sequence
<220> FEATURE:
<223> OTHER INFORMATION: Synthesized Sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Pro Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Arg
                85                  90                  95

Thr Phe Gly Gly Gly Thr Lys Val Glu Ile Lys
            100                 105


<210> SEQ ID NO 16
<211> LENGTH: 345
<212> TYPE: DNA
<213> ORGANISM: Homo sapiens

<400> SEQUENCE: 16

gaggtgcagc tggtggagtc tgggggaggc ttggtccagc ctggagggtc cctgagactc     60

tcctgtgcag cctctggatt caccttcagt gatgcctgga tggattgggt ccgccaggct    120

ccagggaagg ggctggagtg ggttgccgaa attggtaaca agggcaataa tcacgccacg    180

tactatgccg agtctgtaaa aggaagattc accatctcaa gagatgattc aaagaactca    240

ctgtatctgc aaatgaacag cctgaaaacc gaggacacgg ccgtgtatta ctgtaccact    300

aggtttgcat attggggcca aggaaccctg gtcaccgtct cctca                    345


<210> SEQ ID NO 17
<211> LENGTH: 321
<212> TYPE: DNA
```

<213> ORGANISM: Homo sapiens

<400> SEQUENCE: 17
gacatccaga tgacccagtc tccatcctcc ctgtctgcat ctgtaggaga cagagtcacc 60
atcacttgca aggcatccca agatatcaac tcatacttga gttggttcca gcagaaacca 120
gggaaagccc ctaagctcct gatctaccgt gccaataggc ttgtggatgg ggtcccatca 180
aggttcagtg gaagtggatc tgggacagat tttactttca ccatcagcag cctgcagcct 240
gaagatattg caacatatta ctgtttacag tatgatgagt ttccacgtac ttttggcgga 300
gggaccaagg tggagatcaa a 321

<210> SEQ ID NO 18
<211> LENGTH: 345
<212> TYPE: DNA
<213> ORGANISM: Artificial Sequence
<220> FEATURE:
<223> OTHER INFORMATION: Synthesized Sequence

<400> SEQUENCE: 18
gaggtgcagc tggtggagtc tgggggaggc ttggtccagc ctggagggtc cctgagactc 60
tcctgtgcag cctctggatt caccttcagt gatgcctgga tggattgggt ccgccaggct 120
ccagggaagg ggctggagtg ggttgccgaa attggtaaca agggcaataa tcacgccacg 180
aactatgccg agtctgtaaa aggaagattc accatctcaa gagatgattc aaagaactca 240
ctgtatctgc aaatgaacag cctgaaaacc gaggacacgg ccgtgtatta ctgtaccact 300
aggtttgcat attggggcca aggaaccccg gtcaccgtcc cttca 345

<210> SEQ ID NO 19
<211> LENGTH: 321
<212> TYPE: DNA
<213> ORGANISM: Artificial Sequence
<220> FEATURE:
<223> OTHER INFORMATION: Synthesized Sequence

<400> SEQUENCE: 19
gacatccaga tgacccagtc tccatcctcc ctgtctgcat ctgtaggaga cagagtcacc 60
atcccttgca aggcatccca agatatcaac tcatacttga gttggttcca gcagaaacca 120
gggaaagccc ctaagctcct gatctaccgt gccaataggc ttgtggatgg ggtcccatca 180
aggttcagtg gaagtggatc tgggacagat tttactttca ccatcagcag cctgcagcct 240
gaagatattg caacatatta ctgtttacag tatgatgagt ttccacgtac ttttggcgga 300
gggaccaagg tggagatcaa a 321

<210> SEQ ID NO 20
<211> LENGTH: 15
<212> TYPE: PRT
<213> ORGANISM: Artificial Sequence
<220> FEATURE:
<223> OTHER INFORMATION: Synthesized Sequence

<400> SEQUENCE: 20

Gly Gly Gly Gly Ser Gly Gly Gly Gly Ser Gly Gly Gly Gly Ser
1 5 10 15

<210> SEQ ID NO 21
<211> LENGTH: 45
<212> TYPE: DNA
<213> ORGANISM: Artificial Sequence
<220> FEATURE:

<223> OTHER INFORMATION: Synthesized Sequence

<400> SEQUENCE: 21
ggaggtggcg gtagcggagg cggcggttct ggaggtggcg ggagc 45

<210> SEQ ID NO 22
<211> LENGTH: 237
<212> TYPE: PRT
<213> ORGANISM: Artificial Sequence
<220> FEATURE:
<223> OTHER INFORMATION: Synthesized Sequence

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Thr Arg Phe Ala Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Lys Ala Ser Gln Asp Ile Asn
145                 150                 155                 160

Ser Tyr Leu Ser Trp Phe Gln Gln Lys Pro Gly Lys Ala Pro Lys Leu
                165                 170                 175

Leu Ile Tyr Arg Ala Asn Arg Leu Val Asp Gly Val Pro Ser Arg Phe
            180                 185                 190

Ser Gly Ser Gly Ser Gly Thr Asp Phe Thr Phe Thr Ile Ser Ser Leu
        195                 200                 205

Gln Pro Glu Asp Ile Ala Thr Tyr Tyr Cys Leu Gln Tyr Asp Glu Phe
    210                 215                 220

Pro Arg Thr Phe Gly Gly Gly Thr Lys Val Glu Ile Lys
225                 230                 235
```

<210> SEQ ID NO 23
<211> LENGTH: 237
<212> TYPE: PRT
<213> ORGANISM: Artificial Sequence
<220> FEATURE:
<223> OTHER INFORMATION: Synthesized Sequence

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45
```

Ala Glu Ile Gly Asn Lys Gly Asn Asn His Ala Thr Asn Tyr Ala Glu
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Thr Thr Arg Phe Ala Tyr Trp Gly Gln Gly Thr Pro Val Thr
100 105 110

Val Pro Ser Gly Gly Gly Gly Ser Gly Gly Gly Gly Ser Gly Gly Gly
115 120 125

Gly Ser Asp Ile Gln Met Thr Gln Ser Pro Ser Ser Leu Ser Ala Ser
130 135 140

Val Gly Asp Arg Val Thr Ile Pro Cys Lys Ala Ser Gln Asp Ile Asn
145 150 155 160

Ser Tyr Leu Ser Trp Phe Gln Gln Lys Pro Gly Lys Ala Pro Lys Leu
165 170 175

Leu Ile Tyr Arg Ala Asn Arg Leu Val Asp Gly Val Pro Ser Arg Phe
180 185 190

Ser Gly Ser Gly Ser Gly Thr Asp Phe Thr Phe Thr Ile Ser Ser Leu
195 200 205

Gln Pro Glu Asp Ile Ala Thr Tyr Tyr Cys Leu Gln Tyr Asp Glu Phe
210 215 220

Pro Arg Thr Phe Gly Gly Gly Thr Lys Val Glu Ile Lys
225 230 235

<210> SEQ ID NO 24
<211> LENGTH: 30
<212> TYPE: PRT
<213> ORGANISM: Artificial Sequence
<220> FEATURE:
<223> OTHER INFORMATION: Synthesized Sequence

<400> SEQUENCE: 24

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 25
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 25

Trp Val Arg Gln Ala Pro Gly Lys Gly Leu Glu Trp Val Ala
1 5 10

<210> SEQ ID NO 26
<211> LENGTH: 32
<212> TYPE: PRT
<213> ORGANISM: Artificial Sequence
<220> FEATURE:
<223> OTHER INFORMATION: Synthesized Sequence

<400> SEQUENCE: 26

Arg Phe Thr Ile Ser Arg Asp Asp Ser Lys Asn Ser Leu Tyr Leu Gln
1 5 10 15

Met Asn Ser Leu Lys Thr Glu Asp Thr Ala Val Tyr Tyr Cys Thr Thr
20 25 30

<210> SEQ ID NO 27
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 27

Trp Gly Gln Gly Thr Leu Val Thr Val Ser Ser
1 5 10

<210> SEQ ID NO 28
<211> LENGTH: 23
<212> TYPE: PRT
<213> ORGANISM: Artificial Sequence
<220> FEATURE:
<223> OTHER INFORMATION: Synthesized Sequence

<400> SEQUENCE: 28

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 29
<211> LENGTH: 15
<212> TYPE: PRT
<213> ORGANISM: Artificial Sequence
<220> FEATURE:
<223> OTHER INFORMATION: Synthesized Sequence

<400> SEQUENCE: 29

Trp Phe Gln Gln Lys Pro Gly Lys Ala Pro Lys Leu Leu Ile Tyr
1 5 10 15

<210> SEQ ID NO 30
<211> LENGTH: 32
<212> TYPE: PRT
<213> ORGANISM: Artificial Sequence
<220> FEATURE:
<223> OTHER INFORMATION: Synthesized Sequence

<400> SEQUENCE: 30

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 31
<211> LENGTH: 9
<212> TYPE: PRT
<213> ORGANISM: Artificial Sequence
<220> FEATURE:
<223> OTHER INFORMATION: Synthesized Sequence

<400> SEQUENCE: 31

Gly Gly Gly Thr Lys Val Glu Ile Lys
1 5

<210> SEQ ID NO 32
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 32

Trp Gly Gln Gly Thr Pro Val Thr Val Pro Ser
1 5 10

<210> SEQ ID NO 33
<211> LENGTH: 23
<212> TYPE: PRT
<213> ORGANISM: Artificial Sequence
<220> FEATURE:
<223> OTHER INFORMATION: Synthesized Sequence

<400> SEQUENCE: 33

Asp Ile Gln Met Thr Gln Ser Pro Ser Ser Leu Ser Ala Ser Val Gly
1 5 10 15

Asp Arg Val Thr Ile Pro Cys
20

<210> SEQ ID NO 34
<211> LENGTH: 115
<212> TYPE: PRT
<213> ORGANISM: Artificial Sequence
<220> FEATURE:
<223> OTHER INFORMATION: Synthesized Sequence

<400> SEQUENCE: 34

Glu Val Lys Leu Glu Glu Ser Gly Gly Gly Leu Val Gln Pro Gly Gly
1 5 10 15

Ser Met Lys Leu Ser Cys Ala Ala Ser Gly Phe Thr Phe Ser Asp Ala
20 25 30

Trp Met Asp Trp Val Arg Gln Ser Pro Glu Lys Gly Leu Glu Trp Val
35 40 45

Ala Glu Ile Gly Asn Lys Gly Asn Asn His Ala Thr Asn Tyr Ala Glu
50 55 60

Ser Val Lys Gly Arg Phe Thr Val Ser Arg Asp Asp Ser Lys Ser Arg
65 70 75 80

Val Tyr Leu Gln Met Asn Ser Leu Arg Val Glu Asp Thr Gly Thr Tyr
85 90 95

Tyr Cys Thr Thr Arg Phe Ala Tyr Trp Gly Gln Gly Thr Leu Val Thr
100 105 110

Val Ser Ala
115

<210> SEQ ID NO 35
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 35

Gly Gly Gly Gly Ser
1 5

<210> SEQ ID NO 36
<211> LENGTH: 10
<212> TYPE: PRT
<213> ORGANISM: Artificial Sequence
<220> FEATURE:
<223> OTHER INFORMATION: Synthesized Sequence -continued

```
<400> SEQUENCE: 36

Gly Phe Thr Phe Ser Asp Ala Trp Met Asp
1               5                   10


<210> SEQ ID NO 37
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 37

Asn Lys Gly Asn Asn His Ala Thr Tyr Tyr Ala Glu Ser Val Lys Gly
1               5                   10                  15


<210> SEQ ID NO 38
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 38

Asn Lys Gly Asn Asn His Ala Thr Asn Tyr Ala Glu Ser Val Lys Gly
1               5                   10                  15
```